(12) United States Patent
DeLuca et al.

(10) Patent No.: US 8,114,393 B2
(45) Date of Patent: Feb. 14, 2012

(54) METHODS AND COMPOSITIONS FOR PHOSPHATE BINDING

(75) Inventors: Hector F. DeLuca, Deerfield, WI (US); Katarzyna M. Barycka, Madison, WI (US); Lori Plum, Arena, WI (US); Julia Zella, Horicon, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1147 days.

(21) Appl. No.: 11/974,254

(22) Filed: Oct. 12, 2007

(65) Prior Publication Data

US 2009/0004133 A1 Jan. 1, 2009

Related U.S. Application Data

(63) Continuation-in-part of application No. 11/520,389, filed on Sep. 13, 2006.

(60) Provisional application No. 60/717,072, filed on Sep. 14, 2005.

(51) Int. Cl.
*A61K 31/785* (2006.01)
(52) U.S. Cl. .................................................. 424/78.12
(58) Field of Classification Search ........................ None
See application file for complete search history.

(56) References Cited

U.S. PATENT DOCUMENTS

| | | | |
|---|---|---|---|
| 4,871,779 A | 10/1989 | Killat et al. | |
| 5,530,092 A | 6/1996 | Meijer et al. | |
| 5,610,268 A | 3/1997 | Meijer et al. | |
| 5,698,662 A | 12/1997 | Stoelwinder et al. | |
| 5,714,166 A * | 2/1998 | Tomalia et al. | 424/486 |
| 5,788,989 A | 8/1998 | Jansen et al. | |
| 2005/0019923 A1 | 1/2005 | Uchegbu et al. | |
| 2005/0119242 A1 | 6/2005 | DeLuca et al. | |
| 2005/0131138 A1 | 6/2005 | Connor et al. | |
| 2005/0147580 A1 | 7/2005 | Connor et al. | |
| 2005/0209423 A1 | 9/2005 | Chang et al. | |
| 2005/0239901 A1 | 10/2005 | Chang et al. | |
| 2007/0071715 A1 | 3/2007 | DeLuca et al. | |

FOREIGN PATENT DOCUMENTS

| | | |
|---|---|---|
| WO | WO/2004/092118 | 10/2004 |
| WO | WO 2006088958 A2 * | 8/2006 |
| WO | 2008/011047 A2 | 1/2008 |

OTHER PUBLICATIONS

Johan, F.G., "Journal of the American Chemical Society," Apr. 1995, vol. 117, No. 15, pp. 4417-4418.
Zimmer A et al: "Complex formation of Ni(II), Cu(II), Pd(II), and Co(III) with 1,2,3,4-tetraaminobutane." Chemistry 2001, vol. 7, 4:917-931, XP009076062.
Bachmann, F et al: "Synthesis of novel polyurethanes . . . " Macromolecular Chemistry and Physics, 202 (17), 3410-3419 coden: Mchpes; Issn: 1022-1352, 2001, Scheme 1.
Covassin, L et al: "Synthesis of spermidine . . . " Bioorganic & Medicinal Chemistry Letters, Oxford, GB, vol. 9, No. 12, Jun. 21, 1999, 1709-1714 XP004167745.

* cited by examiner

*Primary Examiner* — Michael G Hartley
*Assistant Examiner* — Paul Dickinson
(74) *Attorney, Agent, or Firm* — Quarles & Brady LLP

(57) ABSTRACT

The present invention provides improved methods and compositions for therapeutically controlling and/or reducing serum phosphate levels in animals and mammalian patients. The methods comprise administering to the patient an amount of a dendrimer composition effective to prevent absorption of substantial amounts of phosphate from the patient's GI tract. In a preferred version, a dose of between 2.5 and 15 grams per day is effective to prevent over 80% of phosphate present in the patient's GI tract from being absorbed. The dendrimer composition may comprise a hydrocitrate, hydrochloride, hydrobromide, hydroacetate or hydroanionic form.

8 Claims, 33 Drawing Sheets

DAB-AM-64 DENDRIMER GENERATION 5.0

HCl, CHCl₃ →

× 126 HCl

METHODS AND COMPOSITIONS FOR PHOSPHATE BINDING

CROSS-REFERENCE TO RELATED APPLICATIONS

This application is a Continuation-In-Part of U.S. patent application Ser. No. 11/520,389, filed on Sep. 13, 2006, which claims priority to U.S. Provisional Application No. 60/717,072 filed Sep. 14, 2005, which are hereby incorporated by reference herein.

STATEMENT REGARDING FEDERALLY SPONSORED RESEARCH OR DEVELOPMENT

Not Applicable.

FIELD OF THE INVENTION

The invention relates generally to methods and compositions for therapeutic phosphate binding in a mammalian patient, preferably by use of dendrimers, as defined below. Most preferably, the methods and compositions of the present invention are used with dialysis patients and others who have an inability to excrete phosphate.

BACKGROUND OF THE INVENTION

The kidney is essential not only for its ability to filter toxins and excess nutrients from the blood, but also for its ability to synthesize the active form of vitamin $D_3$, 1,25-dihydroxyvitamin $D_3$ [$1,25(OH)_2D_3$]. In patients with chronic kidney disease, both these functions are impaired. Consequently, levels of $1,25(OH)_2D_3$ decline, leading to hypocalcemia. Meanwhile, nutrients, particularly phosphorus, accumulate in the blood. Hypocalcemia and hyperphosphatemia are both potent stimulators of parathyroid hormone (PTH) secretion. Over time, hyperparathyroidism in the presence of even trace amounts of $1,25(OH)_2D_3$ cause excess bone resorption, leading to a condition known as renal osteodystrophy. (Brown A J et al., Vitamin D analogues for secondary hyperparathyroidism, *Nephrol Dial Transplant* 17 Suppl, 2002, 10:10-19). In addition to dialysis treatment, it is essential to suppress excessive PTH levels and reduce phosphorus in the blood to prevent this condition.

Vitamin D analogs, such as 1,25-dihydroxy-19-nor-vitamin $D_2$ (19-nor-$D_2$, Zemplar®, Abbott Laboratories, Abbott Park, Ill.) and 1α-hydroxyvitamin $D_2$ [1α-(OH)$D_2$, Hectorol®, Genzyme Corporation/Bone Care International, Middleton, Wis.] are administered to patients to suppress hyperparathyroidism. Although these analogs are effective at suppressing PTH levels, they still retain some ability to stimulate intestinal calcium and phosphate absorption, which may be problematic when the analogs are administered at high doses or in conjunction with calcium-based oral phosphate binders. (Brown A J et al.).

Reducing the absorption of phosphorus from foods is also a challenging task. The current Recommended Dietary Allowance (RDA) for phosphorus is 700 mg per day (Food and Nutrition Board, Institute of Medicine, 1997, Dietary reference intakes for calcium, phosphorus, magnesium, vitamin D, and fluoride, Washington, D.C.: *National Academy Press*.), but most Americans consume 1000-1600 mg of phosphorus each day. (Wardlaw G M et al., Perspectives in Nutrition, New York, N.Y.: *McGraw-Hill Higher Education*, 2002). Dietary phosphorus restriction is not very effective due to the richness of phosphorus in foods such as dairy products, meat, fish, eggs, nuts, grains, baked goods, and soft drinks. Moreover, it is estimated that 65-75% of consumed phosphorus is absorbed. (Tenenhouse H S, Regulation of phosphorus homeostasis by the Type IIa Na/phosphate cotransporter. *Annu Rev Nutr* 2005, 25:197-214). As a result, oral phosphate binders are often administered with meals to reduce the absorption of phosphorus.

In the 1970s, aluminum-based binders were extensively used to bind phosphate from foods, but the use was severely reduced after aluminum was shown to accumulate in patients causing toxic side-effects such as bone disease, encephalopathy, and anemia. (Goodman W G, Medical management of secondary hyperparathyroidism in chronic renal failure, *Nephrol Dial Transplant* 2003, 18 Suppl 3:1112-8). Calcium acetate (PhosLo, Nabi Pharmaceuticals, Boca Raton, Fla.) was then developed as an alternative to aluminum-based binders, but must be administered at high levels to be effective. Furthermore, when administered in conjunction with $1,25(OH)_2D_3$ or a vitamin D analog, the oral calcium may contribute to hypercalcemia. (Goodman W R). Recently, lanthanum carbonate (Fosrenol®, Shire US Incorporated, Wayne, Pa.) was approved by the FDA for use as an oral phosphate binder. Although effective, its low rate of absorption raises some speculation that toxicity issues may arise with long-term use. (Coladonato J A, Control of hyperphosphatemia among patients with ESRD, *J Am Soc Nephrol* 2005, 16 Suppl 2:S107-114).

Sevelamer hydrochloride (Renagel®, Genzyme Corporation, Cambridge, Mass.), a phosphate-binding polymer, has been successfully used to reduce absorption of dietary phosphorus with fewer side effects than aluminum or calcium. (Amin N, The impact of improved phosphorus control: use of sevelamer hydrochloride in patients with chronic renal failure, *Nephrol Dial Transplant* 2002, 17:340-345). Unfortunately, sevelamer hydrochloride is costly (average cost of $4400 per year in 2002) and must be taken in large quantities (average dose of 6.5 g per day) to be effective. (Cizman B, Hyperphosphataemia and treatment with sevelamer in haemodialysis patients, *Nephrol Dial Transplant* 2003, 18 Suppl 5:v47-49).

Dendrimers are well known therapeutic tools. Dendrimers have been used in applications including imaging agents, nano-scaffolds, antitumor drugs, gene transfection agents, nanoscale containers and biomimetic artificial proteins. (Svenson S et al., Dendrimers in biomedical applications-reflections on the field, *Advanced Drug Delivery Reviews* 2005, 57:2106-2129).

However, therapeutic dendrimer compositions that bind phosphate, thereby treating hypocalcemia, hyperphosphatemia and chronic kidney disease, are not known.

Thus, a need exists for dendrimeric compositions containing varying amounts of free amines that can bind phosphate and inhibit its absorption in vivo.

BRIEF SUMMARY OF THE INVENTION

The present invention provides an improved method of controlling serum phosphate levels in mammals comprising administering to the mammal an amount of a dendrimer composition effective to prevent absorption of substantial amounts of phosphate from the mammal's GI tract, wherein the mammal's serum phosphate level is controlled. A dose of between 2.5 and 15 grams per day is effective to prevent at least 50% of phosphate present in the mammal's GI tract from being absorbed. In a preferred version at least 80% of the phosphate is prevented from being absorbed. The dendrimer composition may comprise a hydrochloride, hydrobromide, hydroacetate, or some hydro anion form.

In a preferred version the dendrimer is selected from the group consisting of erythro-1,2,3,4-tetraminobutane tetrahydrochloride or diaminobutane. In a further preferred version the dendrimer composition comprises a dendrimer according to Structures 4, 5 or 6 (FIGS. 1D-1F).

In another version, the present invention provides a method of reducing intestinal phosphate absorption in animals by administering to the animal an amount of a dendrimer composition effective to prevent absorption of substantial amounts of phosphate from the animal's GI tract, wherein the animal's serum phosphate level is reduced. In a preferred version, a daily dose of between 2.5 and 15 grams per day is effective to prevent at least 50% of phosphate present in the animal's GI tract from being absorbed. In a preferred version at least 80% of the phosphate is prevented from being absorbed. The dendrimer composition may comprise a hydrochloride, hydrobromide or hydroacetate or other hydroanionic forms.

Another aspect of the invention is a compound comprising a dendrimer having the formula $C_{16-376}H_{40-880}N_{6-126}$, and, a quantity of a pharmaceutically suitable salt in the range of 1-126.

In an exemplary embodiment of the compound, the dendrimer has the formula $C_{16}H_{40}N_6$,

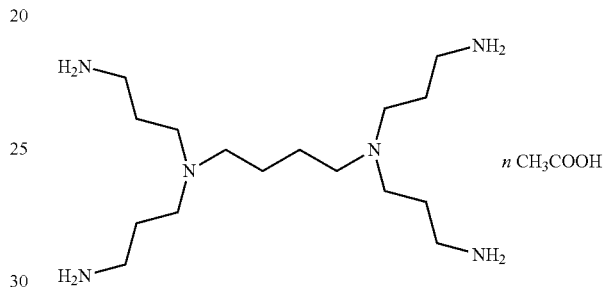

and, n=1-6 hydroacetates, and preferably 5-6 hydroacetates.

In another exemplary embodiment of the compound, the dendrimer has the formula $C_{40}H_{69}N_{14}$,

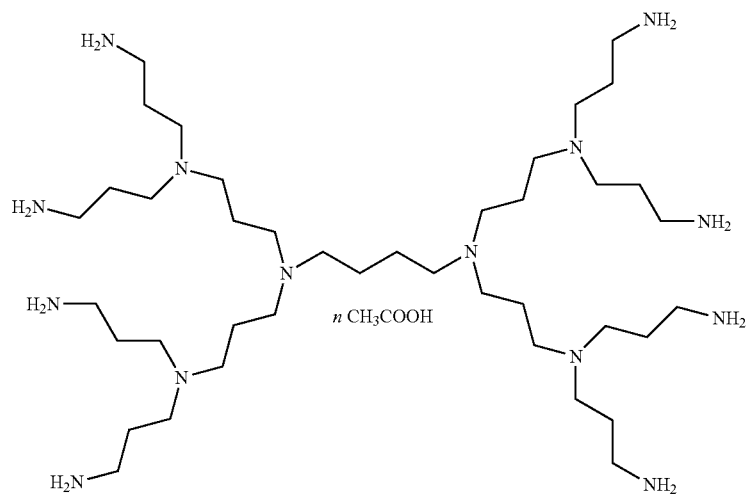

and, n=1-14 hydroacetates, and preferably 12-14 hydroacetates.
In another exemplary embodiment of the compound, the dendrimer has the formula $C_{88}H_{208}N_{30}$,
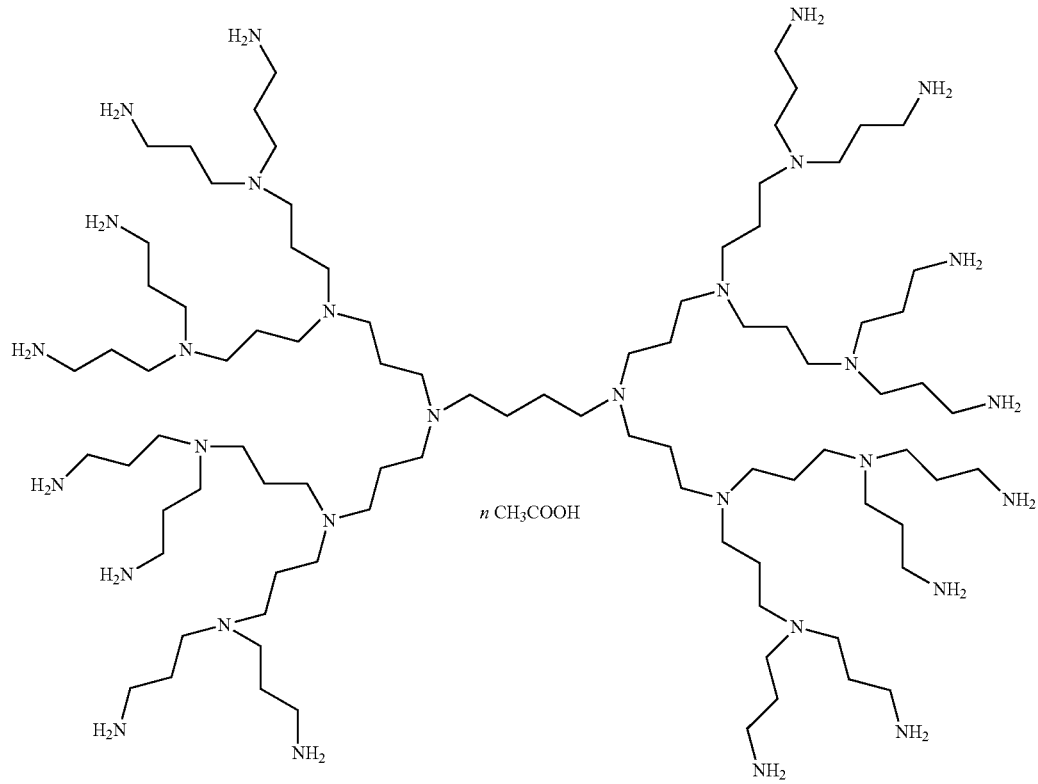
and, n=1-30 hydroacetates, and preferably 27-30 hydroacetates.
In another exemplary embodiment of the compound, the dendrimer has the formula $C_{376}H_{880}N_{126}$,
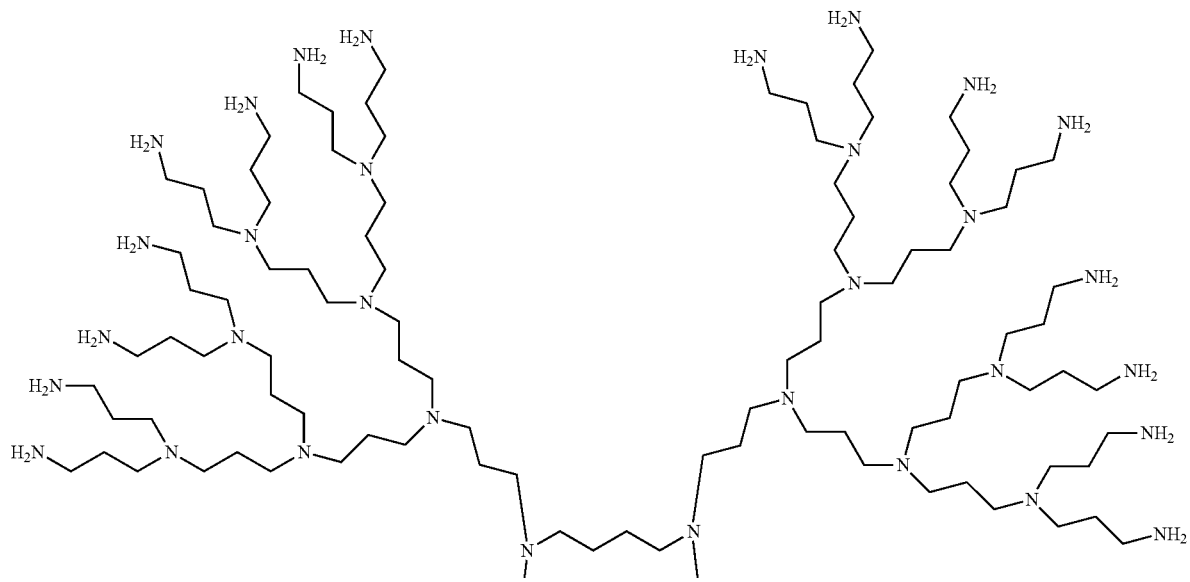

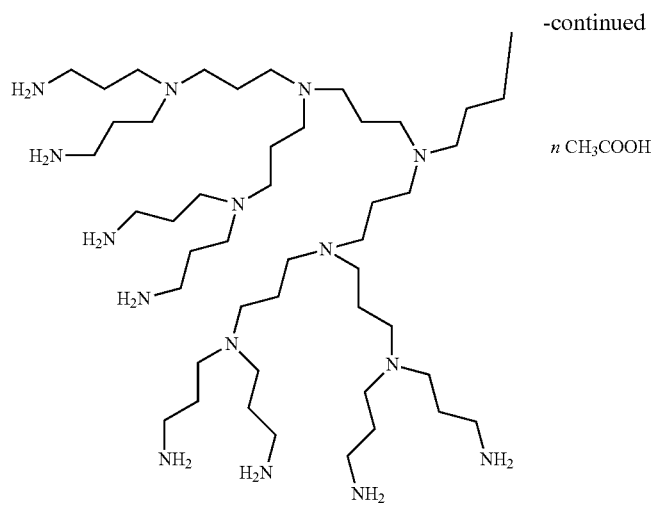
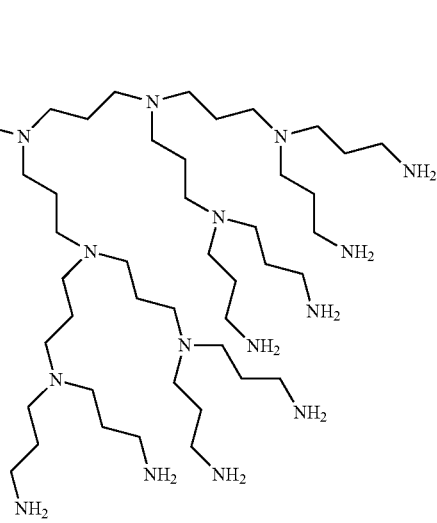
and, n=1-126 hydroacetates, and preferably 113-126 hydroacetates.
In another exemplary embodiment of the compound, the dendrimer has the formula $C_{16}H_{40}N_6$,
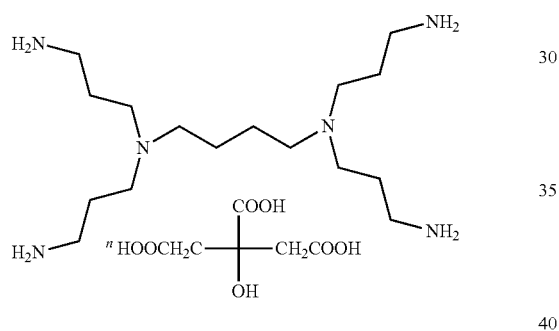
and, n=1-2 hydrocitrates, and preferably 2 hydrocitrates.
In another exemplary embodiment of the compound, the dendrimer has the formula $C_{40}H_{69}N_{14}$,
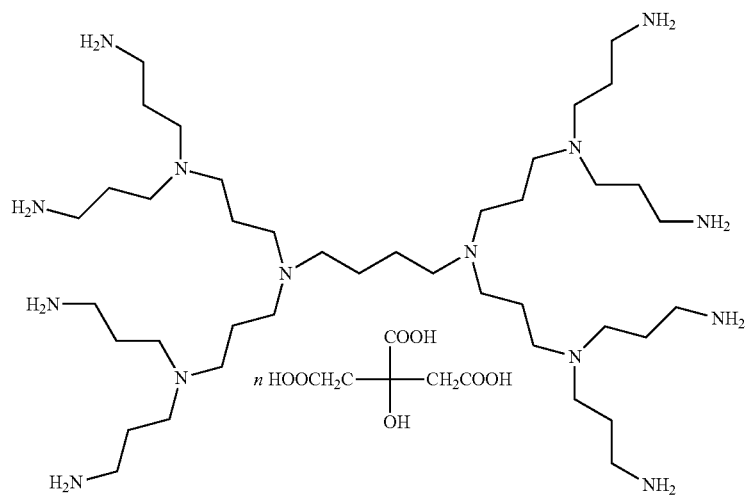
and, n=1-5 hydrocitrates, and preferably 4-5 hydrocitrates.

In another exemplary embodiment of the compound, the dendrimer has the formula $C_{88}H_{208}N_{30}$,
In another exemplary embodiment of the compound, the dendrimer has the formula $C_{376}H_{880}N_{126}$,
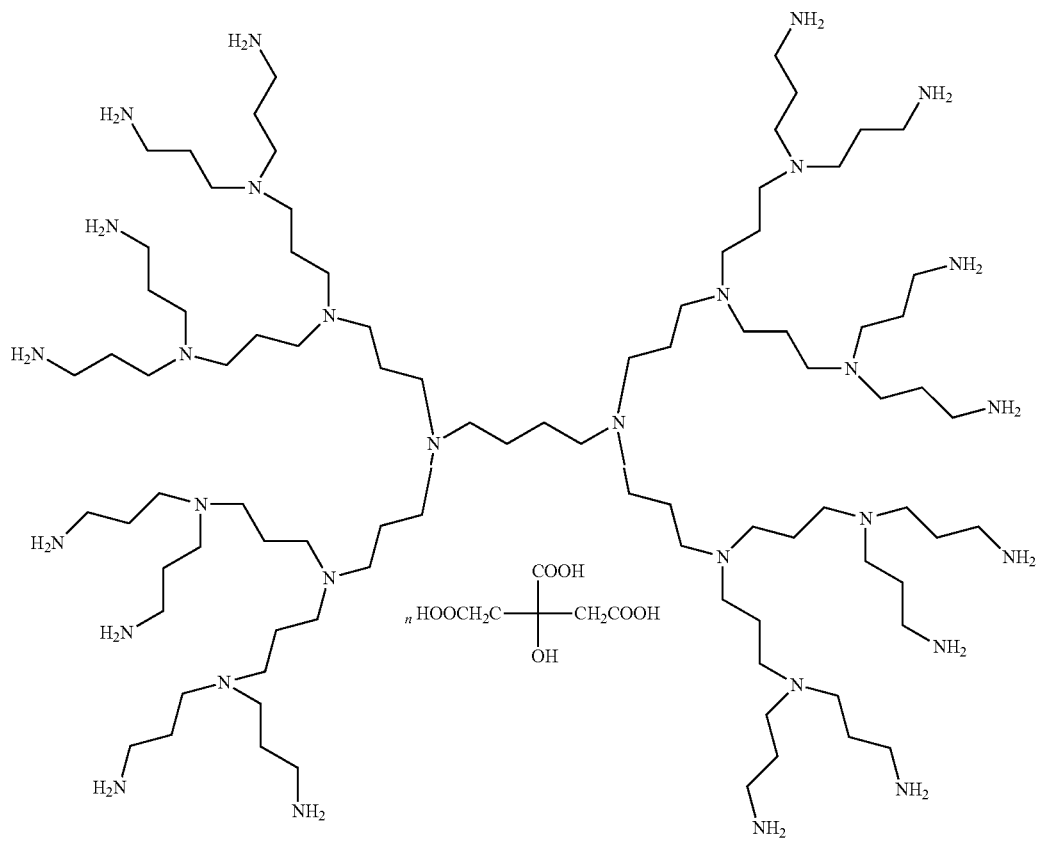
and, n=1-10 hydrocitrates, and preferably 9-10 hydrocitrates.
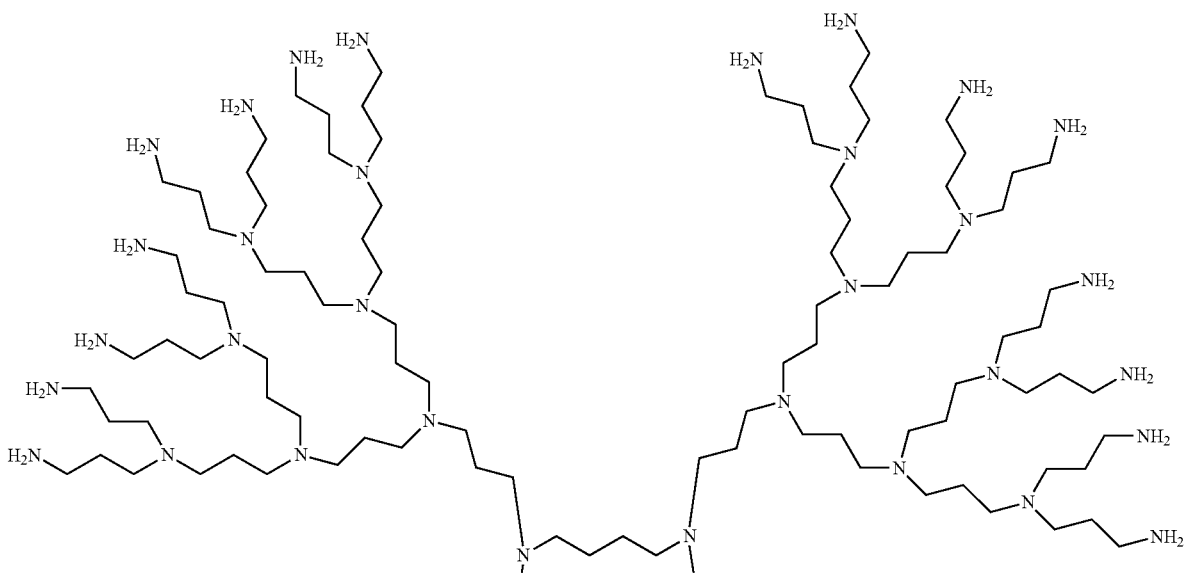

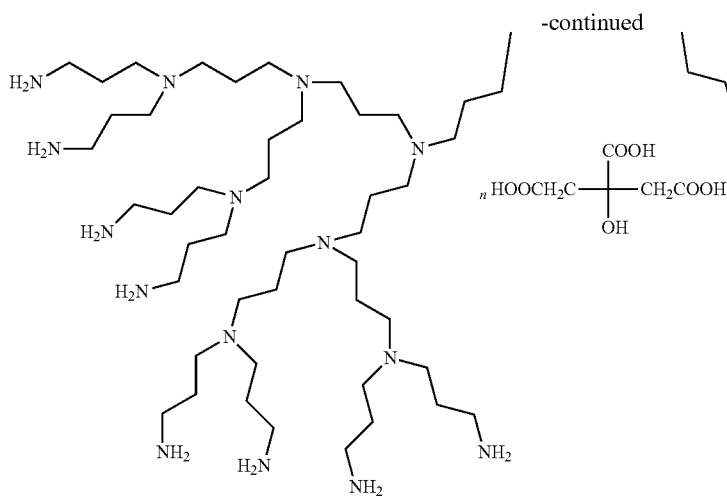
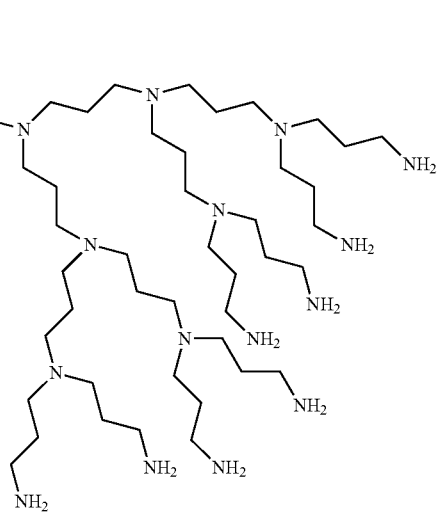

and, n=1-22 hydrocitrates, and preferably 18-22 hydrocitrates.

Another aspect of the invention is a method of treating the serum phosphate level in a human comprising orally administering to the human a therapeutic dose of any of the above dendrimer salt compounds, preferably in a suitable oral dosage form, such as a tablet, capsule, or suspension, whereby the salt may be dissolved in a hydrophillic solvent.

BRIEF DESCRIPTION OF THE FIGURES

FIG. 1 shows therapeutic phosphate binders of the present invention.

FIG. 2 shows that Calcium or Renagel® bind phosphate in vivo. Fasted rats were administered 0.5 mL water or 20 mg calcium (as calcium acetate) or 14.4 mg Renagel® dissolved in water via gastric gavage. Rats were immediately administered a dose of 3 μCi $^{33}$P in 0.5 mL buffer containing 10, 50, or 100 mM $KH_2PO_4$, and killed after 60 minutes.

FIG. 3 compares the novel oral phosphate binders disclosed herein. Fasted rats were administered 0.5 mL water via gastric gavage or 10 mg calcium (as calcium acetate), 14.4 mg Renagel®, or a novel phosphate binder (described in Table 1) dissolved in water. Rats were immediately administered a second dose of 3 μCi $^{33}$P in 0.5 mL buffer containing 10 mM $KH_2PO_4$, and killed after 60 minutes.

FIG. 4 illustrates the dose response to dendrimer compounds. Fasted rats were administered 0.5 mL water via gastric gavage or 14.4 mg Renagel® or a novel phosphate binder dissolved in water. Rats were immediately administered a dose of 3 μCi $^{33}$P in 0.5 mL buffer containing 10 mM $KH_2PO_4$, and killed after 60 minutes.

FIG. 5 illustrates the mechanism underlying the dendrimer's ability to bind phosphate. Fasted rats were administered 0.5 mL water or 14.4 mg Renagel® or a novel phosphate binder dissolved in water via gastric gavage. Rats were immediately administered a dose of 3 μCi $^{33}$P in 0.5 mL buffer containing 10 mM $KH_2PO_4$, and killed after 60 minutes.

DETAILED DESCRIPTION OF THE INVENTION

The present invention provides an improved method of therapeutic phosphate binding in an animal or mammalian patient, preferably by use of a dendrimer, as defined below. Most preferably, the method of present invention is used with dialysis patients and others who have an inability to excrete phosphate.

Figure 1A:
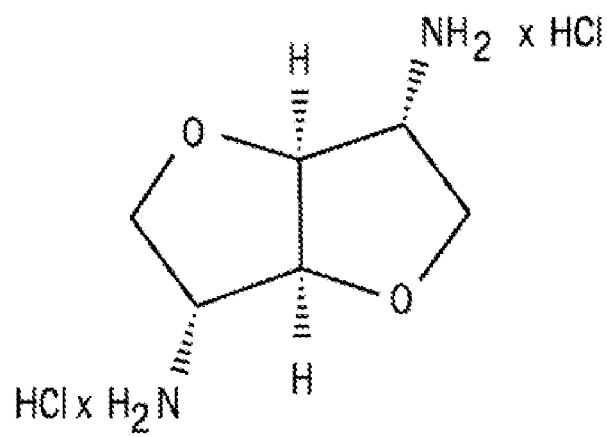
FIG. 1A) Structure 1: 1,4:3,6-Dianhydro-2,5-diamino-2,5-dideoxy-D-iditol dihydrochloride (FC).
Figure 1B:
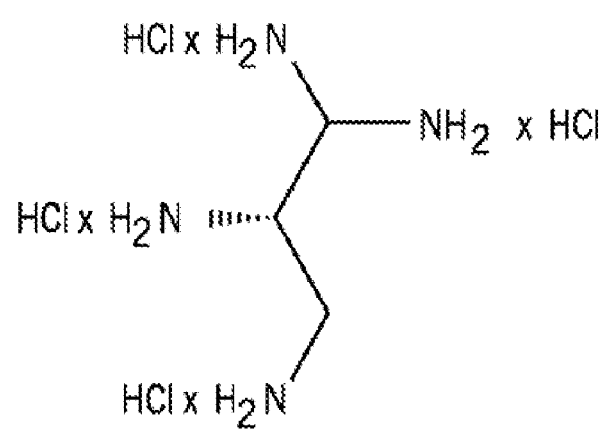
FIG. 1B) Structure 2: erythro-1,2,3,4-tetraminobutane tetrahydrochloride (KB-54).
Figure 1C:
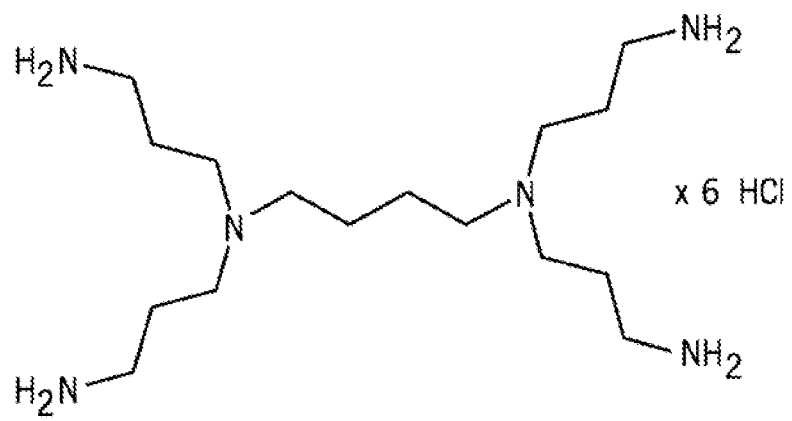
FIG. 1C) Structure 3: Diaminobutane dendrimer Generation 1 (DAB-4-Cl).
Figure 1D:
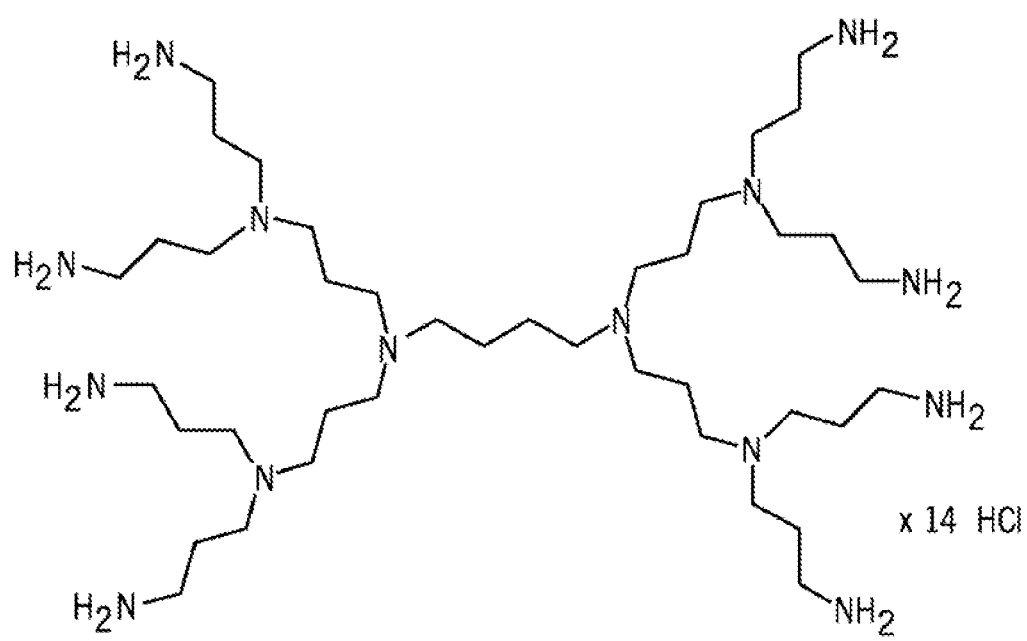
FIG. 1D) Structure 4: Diaminobutane dendrimer Generation 2 (DAB-8-Cl).
Figure 1E:
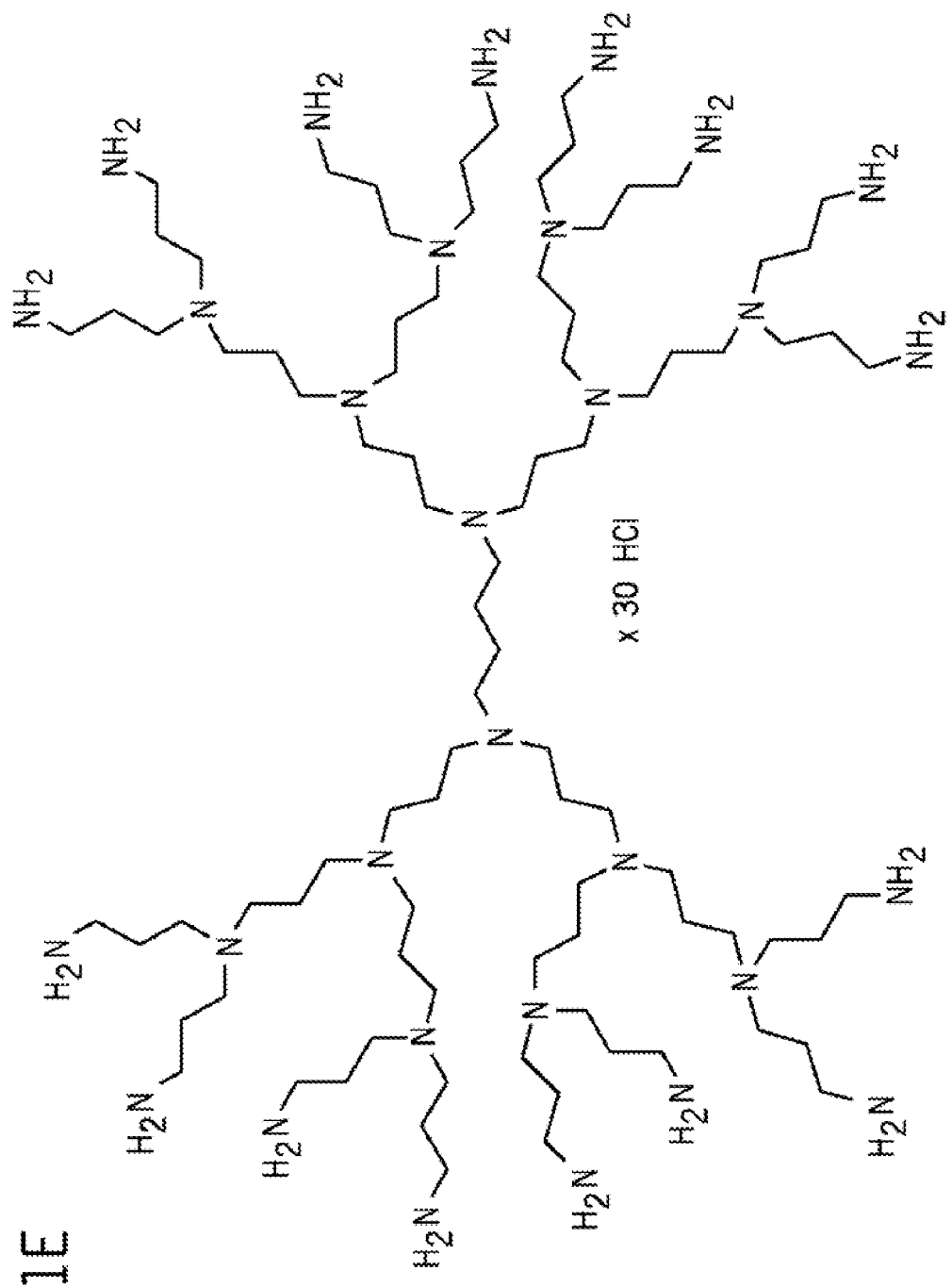
FIG. 1E) Structure 5: Diaminobutane dendrimer Generation 3 (DAB-16-Cl).
Figure 1F:
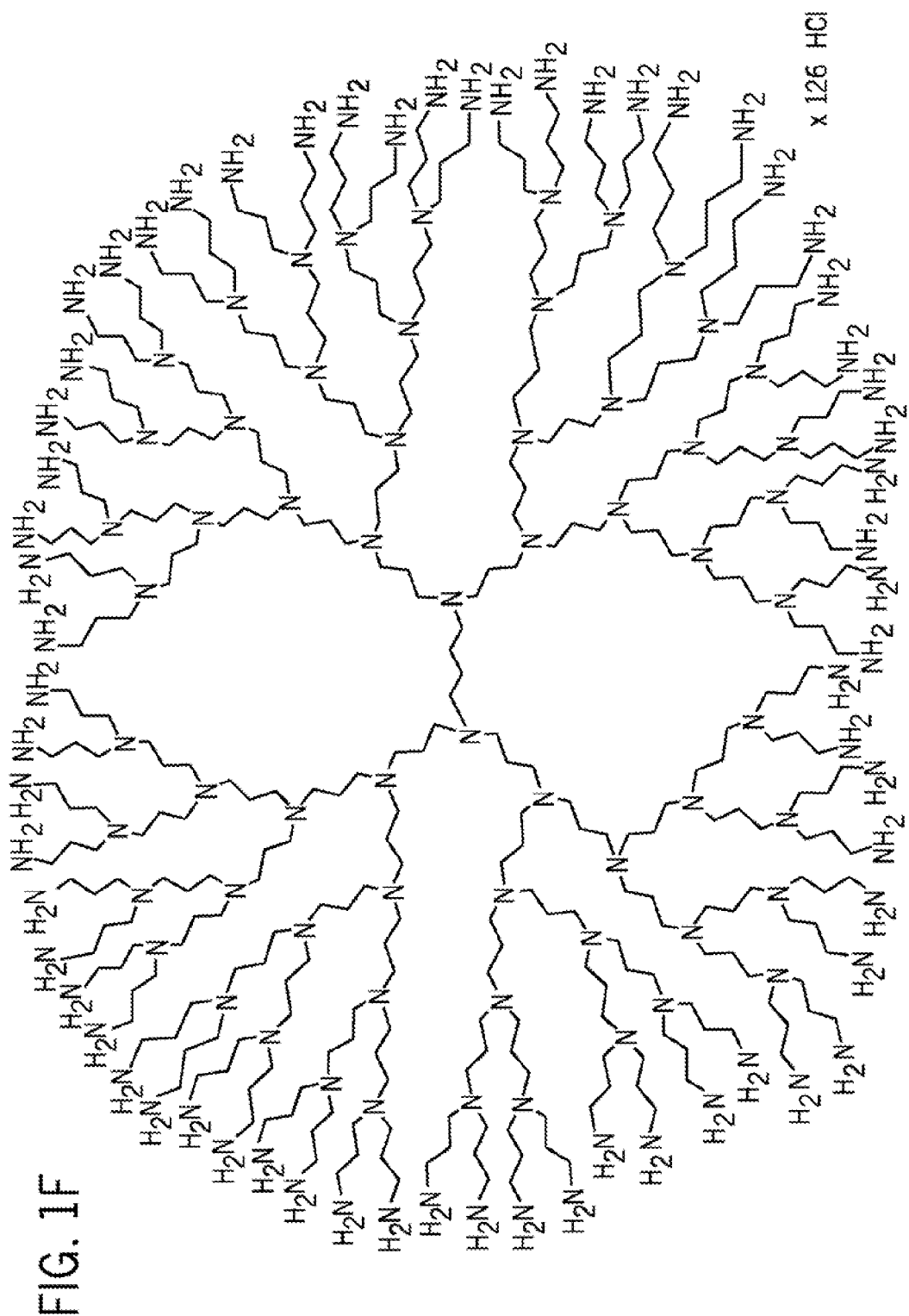
FIG. 1F) Structure 6: Diaminobutane dendrimer Generation 5 (DAB-64-Cl).
Figure 1G:
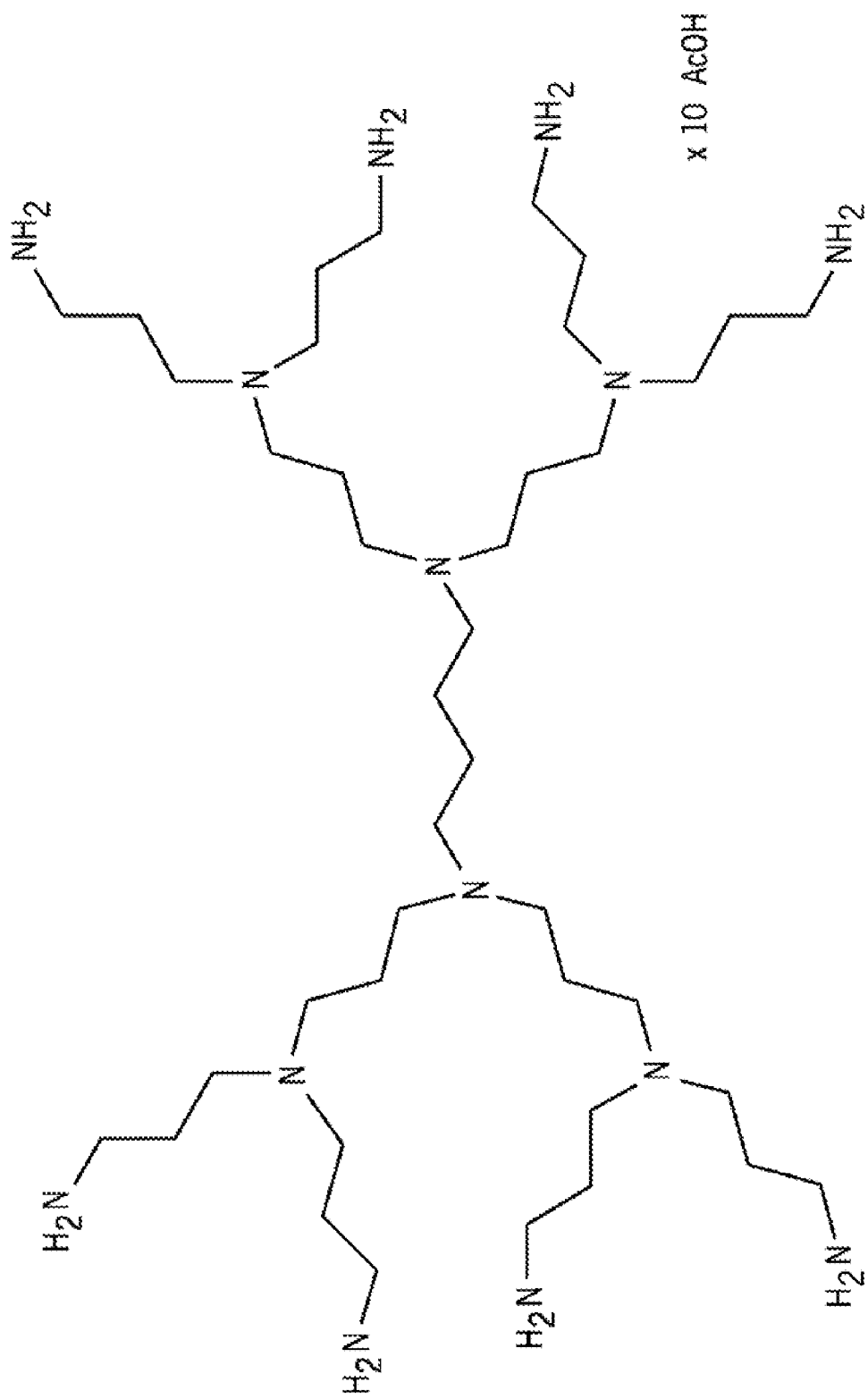
FIG. 1G) Structure 7: DAB-8-AcOH.

The present invention also provides therapeutic dendrimeric compositions. Preferably, the present invention is a hydrochloride, hydrobromide or hydroacetate form of dendrimers described in U.S. Pat. Nos. 5,530,092 and 5,610,268, incorporated herein. Most preferably, the present invention is the hydrochloride form of DAB-16 and DAB-64 (FIGS. 1E and 1F).

The present invention involves treating a patient with an amount of dendrimer composition effective to control serum phosphate levels in the patient. By "control," we mean increase and/or, more preferably, decrease the amount of phosphate absorbed by the patient's GI tract according to the dose and composition of the dendrimer administered to the patient. For instance, when a patient requires reduced levels of serum phosphate, the present invention prevents the absorption of substantial amounts of phosphate from the GI tract. By "substantial," we mean the present invention prevents at least 50% of phosphate from being absorbed in the GI tract. Most preferably, the present invention prevents at least 80% of the phosphate from being absorbed in the GI tract.

The effectiveness of this invention is determined by measuring the serum phosphate levels of the patient by any conventional test known to the art. The present invention is effective when the patient's serum phosphate levels are reduced by at least 10%, but more preferably, when the patient's serum phosphate levels are reduced by at least 20%.

The dendrimer is administered in an amount ranging between 2.5 and 15 grams per day. This dose is preferably equally divided among two or more meals. A preferable route of administration is in liquid form, such as a drink or a capsule. It is an advantage of the present invention that the dendrimer composition is soluble.

The invention also may include a pharmaceutical composition comprising a dendrimer composition combined with a pharmaceutically acceptable carrier intended to reduce and/or control serum phosphate levels in mammals. The composition may be administered to a mammal, a cell, or an isolated organ.

Examples of suitable pharmaceutical carriers are well known in the art and include phosphate buffered saline solutions, water, emulsions, such as oil/water emulsions, various types of wetting agents, sterile solutions and the like. Compositions comprising such carriers can be formulated by well known conventional methods. These pharmaceutical compositions can be administered to the mammal at a suitable dose.

Administration of the suitable compositions may be effected by different ways, e.g. by intravenous, intraperitoneal, subcutaneous, intramuscular, topical or intradermal injection, or by inhalation or intracranial injection.

By "dendrimer composition" we mean to include the molecules described in U.S. Pat. Nos. 5,530,092 and 5,610,268, incorporated by reference herein. These molecules include macromolecules comprising a core and branches emanating from the core, wherein the branches are based on vinyl cyanide and/or fumaryl dinitrile units. Most preferably, the dendrimer comprises a diaminobutane (DAB) dendrimer.

Figure 24:
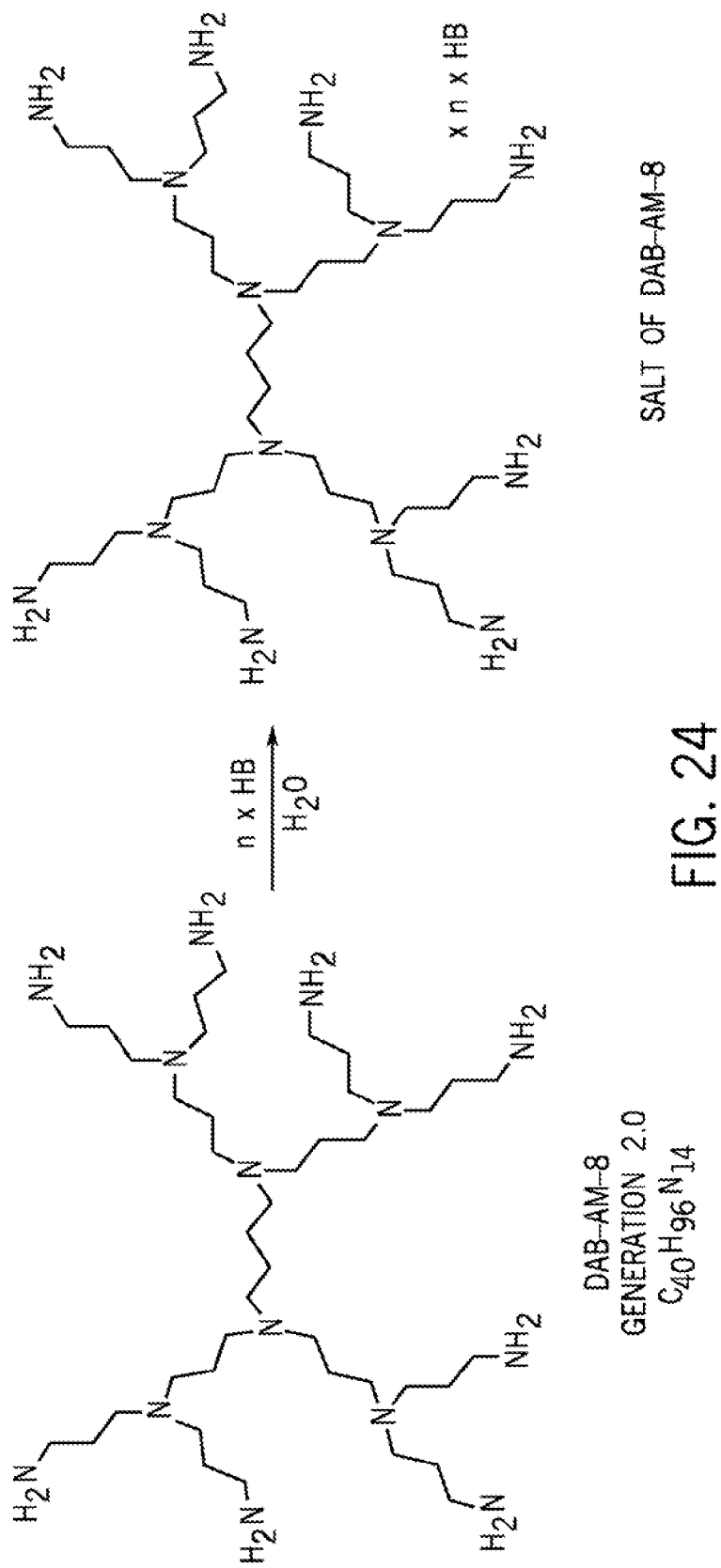
FIG. 24 illustrates the conversion of DAB-Am-8 Dendrimer (Generation 2.0) into its salt form.

By "dendrimer composition" we also mean to include neutralized versions of dendrimers described in the patents listed above. Most preferably, the diaminobutane dendrimer is in the hydrochloride form, as described below. Other preferable neutralized forms include the hydrocitrate, hydrobromide (or any halide or organic acid) form and the hydroacetate form. As depicted in FIG. 24 and Tables 3 and 4, the degree of neutralization of any one of the dendrimers may be varied by varying the titration.

Dendrimer compositions of this kind may be synthesized according to conventional techniques, including those described in U.S. Pat. Nos. 5,530,092 and 5,610,268, incorporated by reference herein, and Buhleier, "Cascade" and "Non-skid-Chain-Like" Synthesis of Molecular Cavity Topologies, Synthesis, 155-158 (February 1978).

EXAMPLES

The following examples set forth preferred aspects of the present invention. It is to be understood, however, that these examples are provided by way of illustration and nothing therein should be taken as a limitation upon the overall scope of the invention.

Materials and Methods

Animals. Male Sprague-Dawley rats (Harlan Sprague-Dawley, Madison, Wis.) weighing approximately 120 grams were used in all experiments.

In experiments to measure $^{33}$P absorption, the rats were fed a laboratory chow diet (Lab Diet 5012, Richmond, Ind.) containing 1% calcium and 0.7% phosphorus ad libitum for less than one week prior to the experiment.

In experiments to measure fecal calcium and phosphorus levels, rats were fed purified diet described previously for 9 days. (Suda T et al., Biological activity of 25-hydroxyergocalciferol in rats, *J Nutr* 1970, 100:1049-1052). This diet was mixed with egg white protein (Harlan Teklad, Madison, Wis.) and contained 0.20% inorganic phosphorus and 0.47% calcium. The purified diet was supplemented with 100 µL soybean oil (Wesson oil, ConAgra Foods, Irvine, Calif.) containing 500 µg α-tocopherol, 60 µg menadione, 40 µg β-carotene, and 1.875 µg cholecalciferol three times each week.

All rats were housed in hanging-wire cages under a 12-hour light/12-hour dark cycle and had free access to distilled water. All experimental methods were approved by the Research Animal Resources Center at the University of Wisconsin-Madison.

Intestinal Phosphate Absorption. Following an overnight fast, rats were administered 0.5 mL water or an oral phosphate binder dissolved in water via gastric gavage. A second dose of 0.5 mL containing 3 μCi $^{33}$P (as $H_3PO_4$, specific activity 155.8 Ci/mg, New England Nuclear/Perkin Elmer, Boston, Mass.) in a 10, 50, or 100 mM $KH_2PO_4$ buffer at pH 7.4 was immediately administered via gastric gavage. Rats were killed by $CO_2$ asphyxiation immediately or 60 minutes after the oral dose. The rats killed immediately (labeled "0 min control" in figures) were used to determine if the oral $^{33}$P dose was properly administered and completely recovered.

Blood was collected via heart puncture and centrifuged at 1500×g for 15 minutes at 22° C. to yield serum. A suture was tied to the cranial end of the esophagus to contain liquid inside the stomach. The entire digestive tract was then removed and allowed to dissolve for several days in concentrated $HNO_3$ (approximately 1 mL $HNO_3$ per gram tissue). The exact volume of the dissolved digestive tract was determined by diluting the dissolved tissues to equal volumes with water.

The amount of radioactivity in total body serum and total volume of dissolved tissue was determined following liquid scintillation counting of 50 μL aliquots in triplicate (Tri-Carb Liquid Scintillation Analyzer, Perkin-Elmer/Packard, Boston, Mass.). Total body serum was estimated to be 40 mL serum/kg body weight. (Hawk T et al., 1999, Formulary for laboratory animals, Ames, Iowa: Iowa State University Press.)

Fecal calcium and phosphorus measurements. Rats were fed the purified diet described above or the same diet with 1.2% calcium, 0.15% Renagel®, or 0.15% DAB-4, DAB-8, or DAB-16 for 7 days. Rats were then moved to metabolic cages and fecal matter was collected for 48 hours. Fecal samples were frozen, lyophilized, and heated to over 600° C. overnight in a muffle oven. Remaining ash was then dissolved overnight in 25 mL 6 N HCl. The calcium concentration of the acid was determined by flame atomic absorption spectroscopy (Model 3110, Perkin Elmer, Norwalk, Conn.) using an aliquot of the dissolved ash diluted 1:40 with 1 g/L $LaCl_3$. The phosphorus concentration of an aliquot of the dissolved ash was determined by a colorimetric assay described previously. (Itaya K et al., A new micromethod for the colorimetric determination of inorganic phosphate, *Clin Chim Acta* 1966, 14:361-366).

Statistical analysis. Data are presented as means±standard error of the means (SEM). Treatment groups were compared by a fully factorial analysis of variance (ANOVA) and means were subjected to Tukey, Scheffe, and Fisher's Least-Significant-Difference (LSD) tests (Systat 5.2.1, Systat Software, Inc., Point Richmond, Calif.). Differences were considered significant if at least two of the tests detected significance with a p-value <0.05, unless specified otherwise.

Figure 6:
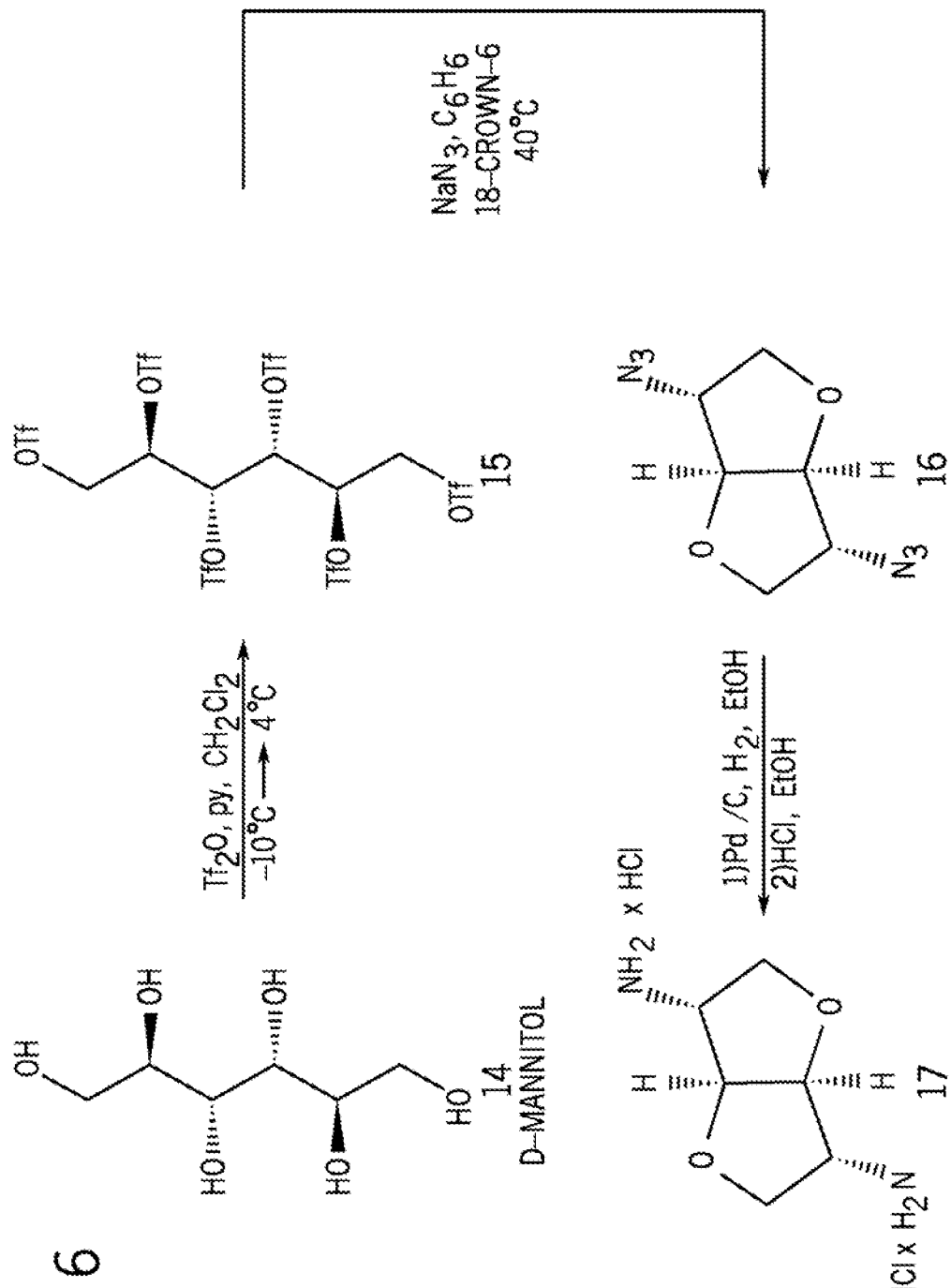
FIG. 6 illustrates the synthesis of Structure 1, FC.

Synthesis of Structure 1, FC. As seen in FIG. 6, the synthesis of Structure 1, FC (compound 17 in FIG. 6) is a three-step process. In step 1, a suspension of 174 mg (0.95 mmol) D-mannitol (compound 14) in 4 mL (49.4 mmol) dry pyridine was stirred under argon at room temperature for 0.5 h. Then, dry dichloromethane (14 mL) was added, the mixture was cooled down to −10° C. (salt-ice bath) and triflic anhydride (1.15 mL, 6.86 mmol) was added dropwise over a 0.5 h period. Stirring was continued at 4° C. (cold room) for 12 h. The solution was diluted with dichloromethane (20 mL) and washed with water (6×7 mL), saturated aqueous solution of $CuSO_4$ (7 mL), again water (3×7 mL) and dried over anhydrous $Na_2SO_4$, filtered. Evaporation of the solvents, then very fast column chromatography (30% hexane/ethyl acetate) afforded an unstable, creamy semisolid, compound 15 (139 mg, 0.14 mmol, 15% yield). $[\alpha]_D$+97.9 (c.1.0, $CHCl_3$); $^1$H NMR (400 MHz, $CDCl_3$): δ 4.15 (m, 2H), 4.77 (dd, 2H, J=4.1 Hz, J=8.1 Hz), 5.21 (dd, 2H, J=4.3 Hz, J=9.3 Hz); $^{13}$C NMR (100 MHz, $CDCl_3$): δ 70.9, 80.4, 80.45, 118.5 (q, $J_{C,F}$=318.98 Hz).

In step 2, 120 mg (0.123 mmol) compound 15 and 72 mg (1.107 mmol) NaN3 were dissolved in dry benzene (2 mL). The 18-crown-6 (0.956 g, 0.36 mmol) was added and the reaction mixture was stirred under argon at 40° C. for 3 h, then cooled down to room temperature, diluted with CH2CL2 (10 mL) and washed with water (6×4 mL). Organic layer was dried over anhydrous Na2SO4, filtered and very carefully concentrated under reduced pressure. The residue was purified by column chromatography (20% ethylacetate/hexane). After chromatography, solvents were removed under reduced pressure and finally by purging a stream of argon for 1 h to give compound 16 as a colorless oil (20 mg, 0.102 mmol, 83% yield). $^1$H NMR (400 MHz, $CDCl_3$): δ 3.89 (dd, 2H, J=4.0 Hz, J=10.2 Hz), 3.93 (dd, 2H, J=1.5 Hz, J=10.1 Hz), 4.6 (dd, 2H, J=1.2 Hz, J=3.8 Hz); $^{13}$C NMR (100 MHz, $CDCl_3$): δ 65.7, 71.9, 86.0.

In step 3, 20 mg (0.102 mmol) of compound 16 was dissolved in 2 mL ethanol and 10 mg of 10% Pd/.C was added. Air was removed by purging with argon for 15 min. The mixture was hydrogenated using a slow stream of hydrogen at room temperature for 3 h (TLC control, 20% ethyl acetate/hexane). After that, the mixture was filtered through celite. Flask and celite were washed with ethanol (10 mL). Filtrate containing crude 1,4:3,6-dianhydro-2,5-diamino-2,5-dideoxy-D-iditol was treated with a solution of HCl (aqueous HCl—37.3%: 35 μL, 0.432 mmol; ethanol: 1.2 mL) and stirred at room temperature for 2 h. Precipitate was then filtered off, washed with ethanol (15 mL), dried on air for 12 h and next in a vacuum oven at 60° C. for 48 h to give 13 mg (0.06 mmol, after two steps 59% yield) of compound 17 as a white crystal (m.p. above 270° C.; at 250° C. the compound turns dark grey. $[\alpha]_D$+55.2 (c.1.1, $H_2O$); $^1$H NMR (400 MHz, $D_2O$): δ 4.01-4.07 (m, 4H) 4.22 (dd, 2H, J=5.1 Hz, J=10.9 Hz), 5.01 (s, 2H); J=1.5 Hz, J=10.1 Hz), $^1$H NMR (400 MHz, DMSO-$d_6$): δ 3.68 (br s, 2H), 3.88 (dd, 2H, J=2.6 Hz, J=10.3 Hz), 3.98 (dd, 2H, J=5.2 Hz, J=10.4 Hz), 4.85 (s, 2H), 8.71 (br s, 6H); $^{13}$C NMR (100 MHz, $D_2O$): δ 55.9, 70.1, 84.6; $^{13}$C NMR (100 MHz, DMSO-$d_6$): δ 55.5, 70.2, 84.7; Elemental analysis calculated for $C_6H_{14}O_2N_2Cl_2$: C, 33.52%; H, 6.56%; N, 13.03%; Cl, 32.03%. found C, 33.24%; H, 6.43%; N, 12.72%; Cl, 33.98%.

Figure 7:
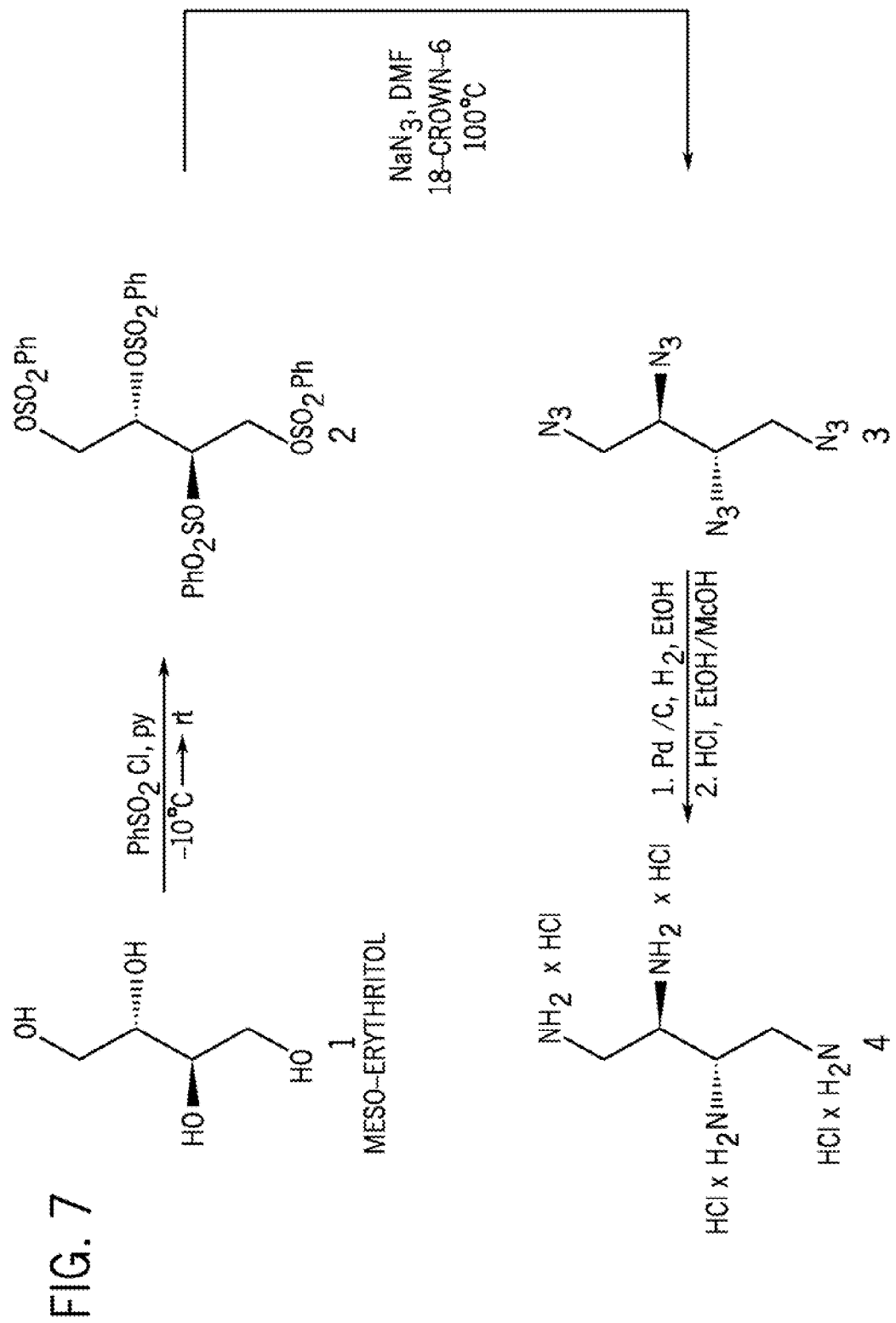
FIG. 7 illustrates the synthesis of Structure 2, KB-54.

Synthesis of Structure 2, KB-54. As seen in FIG. 7, the synthesis of Structure 2, KB-54 (compound 4 in FIG. 7) is a three-step process. Step 1 involves the synthesis of 1,2,3,4-Tetra-O-benzenesulfonyl-meso-erythritol (compound 2). Compound 3 is synthesized by dissolving 13 g (106 mmol) of meso-erythritol (compound 1) in dry pyridine (400 ml). The solution was cooled to −10° C. (salt ice bath) and benzenesulfonyl chloride (81.5 mL, 640 mmol) was added dropwise over a 1 h period. The cooling bath was removed and the mixture was stirred at room temperature for 5 h. The precipitate was collected and washed with ethyl acetate (250 ml), water (1L0 and again with ethyl acetate (200 ml). Then the product was dried with air for 12 h and then in vacuum oven at 50° C. for 30 h to yield 27 g (39 mmol, 37% yield) of white crystals (compound 2) (m.p. 184-186° C., lit. m.p. 184-185.5° C.-R. L. Willer, *J. Org. Chem.*, 1984, 49, 5150-5154). The organic filtrates were combined, concentrated to 200 mL and allowed to stand at room temperature to give the next portion of the crystalline product. Washing and drying procedures were repeated, yielding 30 g (44 mmol, 41% yield) of a second portion of compound 2 (m.p. 183-185° C.). Total yield was 57 g (83 mmol, 78% yield). $^1$H NMR (400 MHz, D$_2$O): δ 4.03 (dd, 2H, J=6.6 Hz, J=11.5 Hz), 4.31 (d, 2H, J=11.5 Hz), 5.03 (d, 2H, J=6.7 Hz), 7.60-7.81 (m, 20H); $^{13}$C NMR (100 MHz, DMSO-d$_6$): δ 66.7, 76.7, 127.56, 129.7, 129.8, 134.3, 134.6, 134.7, 134.8; MS (ESI) exact mass calculated for C$_{28}$H$_{26}$O$_{12}$S$_4$Na([M+Na]$^+$) 705.0205. found 705.175.

Step 2 involves the synthesis of erythro-1,2,3,4-tetraazidobutane (compound 3). This is accomplished by combining 27 g (39 mmol) of compound 2 with 17.17 g (264 mmol) NaN$_3$, 0.5 g (1.89 mmol) 18-crown-6 and 220 mL dry DMF in a flask equipped with a refluxing condenser. The reaction mixture was stirred at 100° C. for 48 h and then cooled to room temperature, diluted with water (0.5 L) and washed with CH$_2$Cl$_2$ (7×200 mL). Organic layers were combined, washed with water (8×100 mL) and saturated aqueous solution of NaCl (3×100 mL) dried over anhydrous Na$_2$SO$_4$, filtered and very carefully concentrated under reduced pressure. The dark brown residue (containing small amounts of DMF) was purified by column chromatograph (Hexane, 5-10% ethyl acetate/hexane) to give 6.36 g (0.028 mmol, 72% yield) of compound 3, a colorless liquid. Because of well known hazards of polyazido compounds, the product was partially concentrated under reduced pressure after chromatography and the residue of solvents was removed by purging a stream of argon for 2 h (R. L. Willer, J. Org. Chem., 1984, 49, 5150-5154). $^1$H NMR (400 MHz, CDCl$_3$): δ 3.52-3.8 (m, 4H) 3.67 (d, 2H, J=10.2 Hz); $^{13}$C NMR (100 MHz, CDCl$_3$): δ 52.0, 61.5.

In step 3, 5.93 g (26.7 mmol) compound 3 was dissolved in 130 mL ethanol and 1.5 g 10% Pd/C was added. Air was removed by purging with argon for 15 min. The mixture was hydrogenated using a slow stream of hydrogen at room temperature for 5 h (TLC control, 10% ethylacetate/hexane). After that the mixture was filtered through celite. Flask and celite were washed with methanol (12 mL). Filtrate containing crude erythro-1,2,3,4-tetraminobutane was treated with solution of HCl (aqueous HCl-36.3%: 9.73 ml, 117.4 mmol; methanol: 34 mL) and stirred at room temperature for 12 h. Pale pink precipitated was filtered off, washed with methanol (300 mL), dried on air for 12 h and then in vacuum oven at 60° C. for 48 h to give 4.84 g (8.3 mmol, after two steps, 68% yield) of compound 4 (m.p. 255° C.; at 150° C. compound 4 turns brown). $^1$H NMR (400 MHz, D$_2$O): δ 3.20 (dd, 2H, J=8.6 Hz, J=14.0 Hz), 3.35 (dd, 2H, J=3.0 Hz, J=14.0 Hz), 3.75 (br d, 2H, J=9.3 Hz); $^1$H NMR (400 MHz, DMSO-d$_6$): δ 3.31 (dd, 2H, J=7.2 Hz, J=14.2 Hz), 3.47 (dd, 2H, J=3.8 Hz, J=14.3 Hz), 4.08 (br d, 2H, J=8.9 Hz), 8.98 (br s, 12H); $^{13}$C NMR (100 MHz, D$_2$O): δ 39.0, 50.3; $^{13}$C NMR (100 MHz, DMSO-d$_6$): δ38.2, 49.9; Elemental analysis calculated for C$_4$H$_{18}$N$_4$Cl$_4$: C, 18.19%; H, 6.87%; N, 21.21%; Cl, 53.71%. found C, 18.37%; H, 7.01%, N, 21.29%; Cl, 53.46%.

Figure 8:
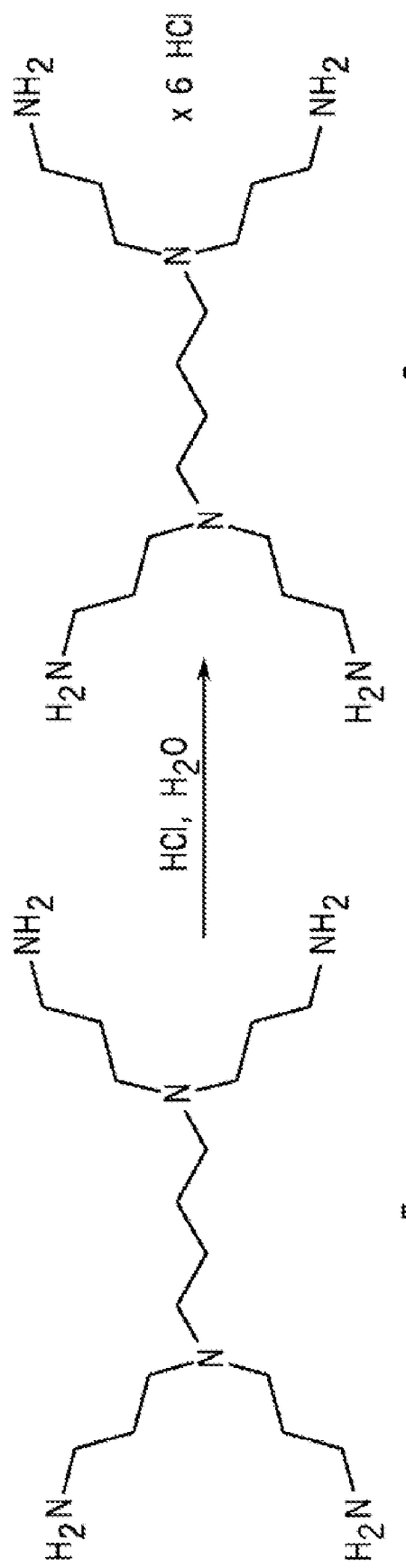
FIG. 8 illustrates the synthesis of Structure 3, DAB-4-Cl.

Synthesis of Structure 3, DAB-4-Cl. As seen in FIG. 8, the conversion of DAB-Am-4 dendrimer into hydrochloride (compound 6) is accomplished by dissolving 8.47 g (26.76 mmol) of DAB-Am-4, Polypropylenimine tetraamine Dendrimer, Generation 1.0 (DSM product) (compound 5) in deionized water (200 mL). Air was removed by purging with argon for 15 min and solution of HCl (aqueous HCl—37.0%: 15.85 mL, 193.02 mmol; deionized water: 30 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (48 h) and finally in vacuum oven at 60° C. for 2 days to yield 14.32 g (26.75 mmol, quantitative yield) of beige crystal (compound 6) (m.p. 242-245° C.). $^1$H NMR (400 MHz, D$_2$O): δ 1.89 (s, 4H), 2.14-2.24 (m, 8H), 3.15 (t, 8H, J=7.5 Hz), 3.36-3.40 (m, 12H); $^{13}$C NMR (100 MHz, D$_2$O): δ 20.5, 21.6, 36.4, 49.9, 52.3; Elemental analysis calculated for C$_{16}$H$_{46}$N$_6$Cl$_6$: C, 35.90%; H, 8.66%; N, 15.69%; Cl, 39.73%. found C, 35.88%; H, 8.73%; N, 15.28%; Cl, 39.25%.

Figure 9:
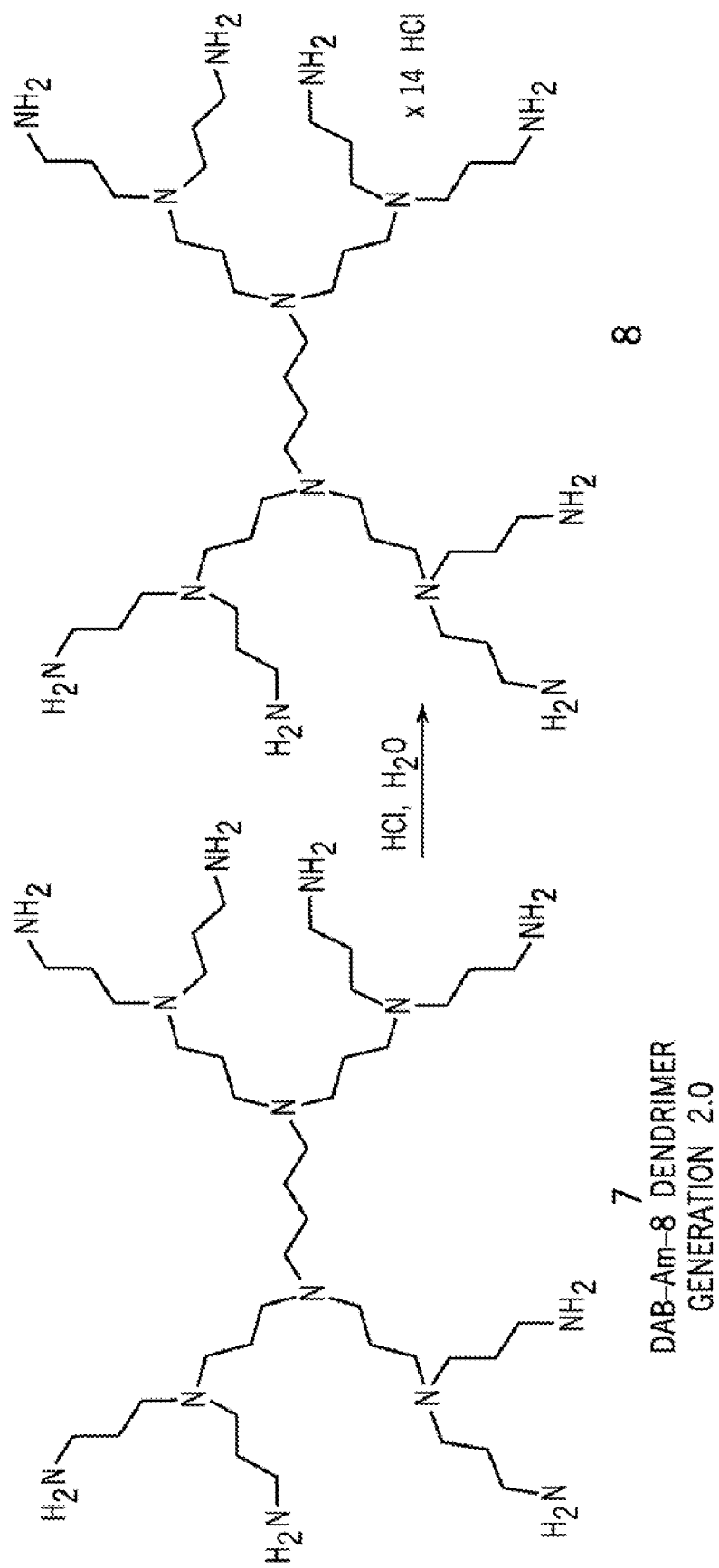
FIG. 9 illustrates the synthesis of Structure 4, DAB-8-Cl.

Synthesis of Structure 4, DAB-8-Cl. As seen in FIG. 9, the conversion of DAB-Am-8 Dendrimer, Generation 2.0 into hydrochloride (compound 8) is accomplished by dissolving (10 g, 12.93 mmol) of DAB-Am-8 Polypropylenimine octaamine Dendrimer, Generation 2.0 (DSM product) in deionized water (300 mL). Air was removed by purging with argon for 15 min and solution of HCl (aqueous HCl—37.0%: 19.3 mL, 235.44 mmol; deionized water: 40 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (24 h) and finally in vacuum oven at 60° C. for 3 days to yield 16.44 g (12.81 mmol, 99%) of white crystalline compound 8 (m.p. 153-155° C.). $^1$H NMR (400 MHz, D$_2$O): δ 1.94 (s, 4H), 2.18-2.23 (m, 16H), 2.26-2.34 (m, 8H), 3.16 (t, 16H, J=7.8 Hz), 3.41-3.43 (m, 36H); $^{13}$C NMR (100 MHz, D$_2$O): δ 19.0, 20.6, 21.6, 36.4, 49.8, 49.9, 50.0, 52.6; Elemental analysis calculated for C$_{40}$H$_{110}$N$_{14}$Cl$_{14}$: C, 37.42%; H, 8.63%; N, 15.27%; Cl, 38.66%. found C, 35.81%; H, 9.22%; N, 14.52%; Cl, 37.66%. Ratio of elements indicates full conversion of amino groups into hydrochlorides: calculated Cl/C, 1.03; Cl/N, 2.53; C/N, 2.45. found Cl/C, 1.05; Cl/N, 2.59; C/N, 2.46.

Figure 10:
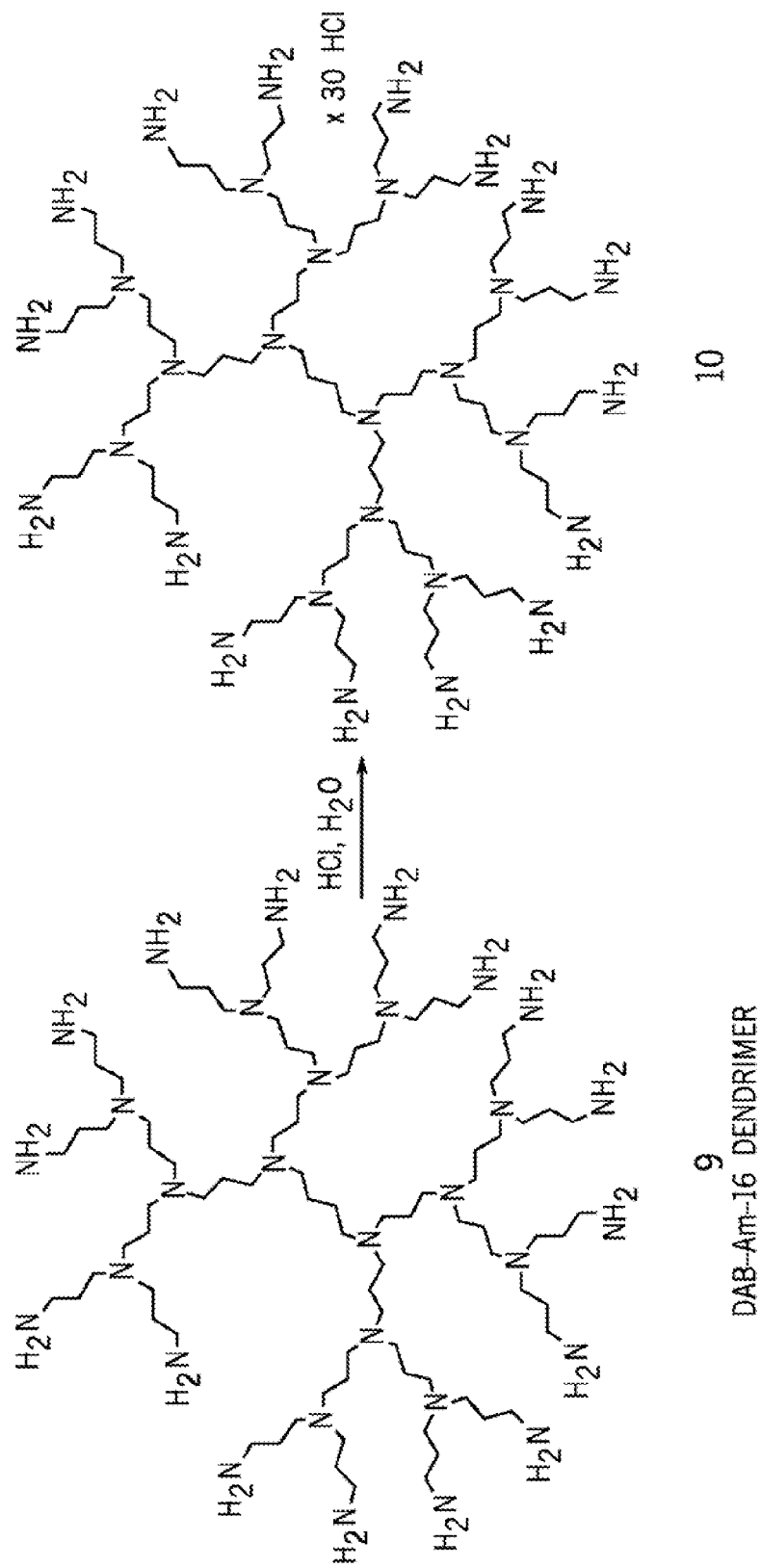
FIG. 10 illustrates the synthesis of Structure 5, DAB-16-Cl.

Synthesis of Structure 5, DAB-16-Cl. As seen in FIG. 10, the conversion of DAB-Am-16 dendrimer, Generation 3.0 into hydrochloride (10) is accomplished by dissolving 5 g (2.96 mmol) DAB-Am-16 dendrimer, polypropylenimine hexadecaamine dendrimer (9) in deionized water (150 mL). Air was removed by purging with argon for 15 min and HCl solution (aqueous HCl—37%: 9.5 mL, 115.56 mmol deionized water: 20 mL) was added dropwise. Reaction mixture was stirred at room temperature for 1 h and then solvents were removed under reduced pressure. Residue was dissolved in 150 mL deionized water and evaporated (procedure was repeated five times), dried on vacuum pump (24 h) and finally in vacuum oven at 60° C. for 3 days to yield 8.24 g (2.96 mmol, quantitative yield) of creamy crystalline compound (10) (m.p. 266° C.). $^1$H NMR (600 MHz, D$_2$O): δ 1.81 (s, 4H), 2.07-2.10 (m, 32H), 2.14-2.19 (m, 24H), 3.06 (t, 32H, J=7.7 Hz), 3.28-2.37 (m, 84H); $^{13}$C NMR (100 MHz, D$_2$O): δ 19.0, 19.1, 20.7, 21.6, 36.4, 49.8, 49.9, 50.1, 50.3, 52.9; Elemental analysis calculated for C$_{88}$H$_{238}$N$_{30}$Cl$_{30}$: C, 38.01%; H, 8.63%; N, 15.11%; Cl, 38.25%. found C, 38.25%; H, 9.13%; N, 15.11%; Cl, 38.25%. Ratio of elements indicates full conversion of amino groups into hydrochlorides: calculated Cl/C, 1.01; Cl/N, 2.53; C/N, 2.51. found Cl/C, 1.03; Cl/N, 2.60; C/N, 2.52.

Figure 11:
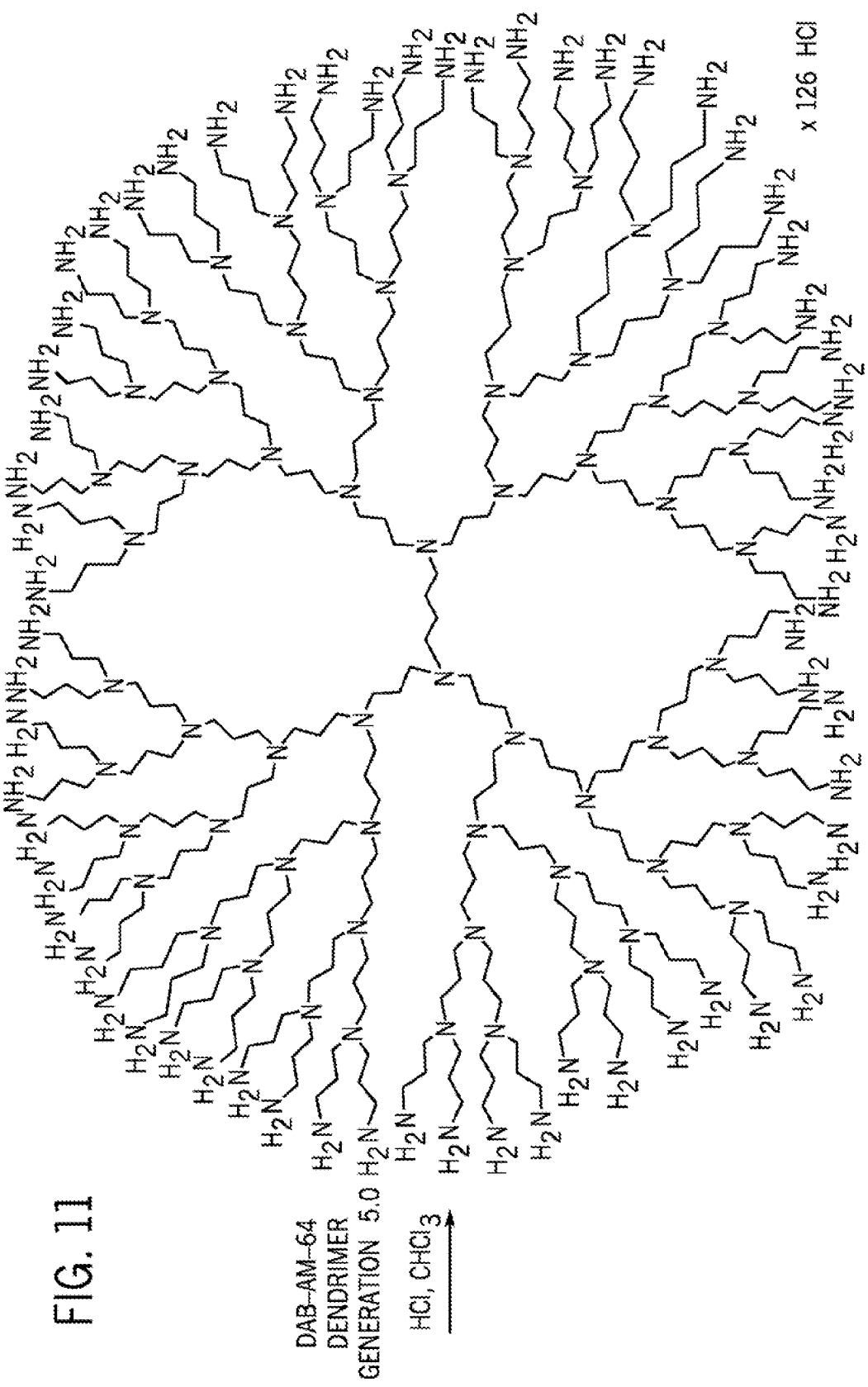
FIG. 11 illustrates the synthesis of Structure 6, DAB-64-Cl.

Synthesis of Structure 6, DAB-64-Cl. As seen in FIG. 11, the conversion of DAB-Am-64 dendrimer, Generation 5.0 into hydrochloride (12) is accomplished by dissolving 1.06 g (0.14 mmol) of DAB-Am-64, polypropylenimine tetrahexacontaamine dendrimers in CH$_3$Cl (25 mL). Air was removed by purging with argon for 15 min and concentrated solution of HCl (aqueous HCl—37.3%: 1.66 mL, 19.99 mmol) was added dropwise. Reaction mixture was stirred at room temperature for 1 h and then solvents were removed under reduced pressure. The residue was dissolved in 20 mL of deionized water and evaporated (procedure was repeated five times), dried on vacuum pump (5 h) and finally in vacuum oven at 60° C. for 3 days to yield 1.525 g (0.13 mmol, 95% yield) of yellow crystalline compound (12) (m.p. 274-276° C.). $^1$H NMR (600 MHz, $D_2O$): δ 1.793 (s, 4H), 2.11-2.19 and 2.23-2.34 (2×m, 248H), 3.09 (t, 128H, J=7.6 Hz), 2.32-2.47 (m, 372H); $^{13}$C NMR (100 MHz, $D_2O$)—only easy visible signals: δ 19.2, 19.3, 20.9, 21.8, 36.7, 49.3, 49.7, 49.9, 50.3, 51.0; Elemental analysis calculated for $C_{376}H_{1006}N_{126}Cl_{126}$: C, 38.39%; H, 8.62%; N, 15.00%; Cl, 37.97%. found C, 38.43%; H, 9.25%; N, 15.05%; Cl 38.35%. Ratio of elements indicates full conversion of amino groups into hydrochlorides: calculated Cl/C, 0.99; Cl/N, 2.53; C/N, 2.55. found Cl/C, 0.99; Cl/N, 2.54; C/N, 2.55.

Figure 12:
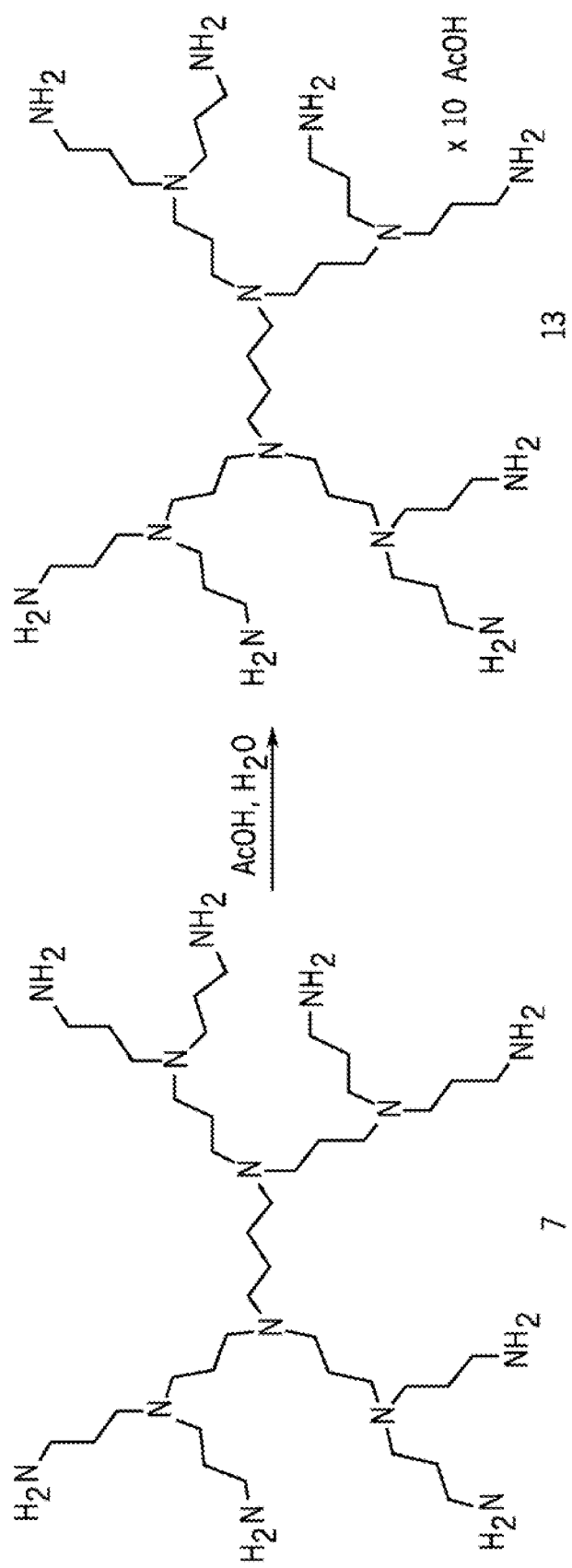
FIG. 12 illustrates the synthesis of Structure 7, DAB-8-AcOH.

Synthesis of Structure 7, DAB-8-AcOH. As seen in FIG. 12, the conversion of DAB-Am-8 dendrimer, Generation 2.0 into decahydroacetate is accomplished by dissolving 6.92 g (8.95 mmol) of DAB-Am-8, Polypropylenimine octaamine Dendrimer, Generation 2.0 (DSM product) 1 in deionized water (260 mL). Air was removed by purging with argon for 15 min and solution of AcOH (glacial AcOH: 8.0 mL, 137.86 mmol; deionized water: 160 mL) was added dropwise. Reaction mixture was stirred at room temperature for 12 h and then solvents were removed under reduced pressure. Residue was dissolved in 250 mL of deionized water and evaporated (procedure was repeated sixteen times). Finally sample was dissolved in 100 mL of deionized water, frozen and lyophilized (48 h) to yield 11.78 g (8.57 mmol, 96%) of compound 3 as the very sticky pale orange oil. $^1$H NMR (400 MHz, $D_2O$): δ 1.63 (s, 4H), 1.74-1.85 (m, 24H), 1.88 (s, 30H), 2.52-2.62 (m, 24H), 2.86-3.02 (m, 28H); $^{13}$C NMR (100 MHz, $D_2O$): δ 20.9, 21.7, 23.2, 23.4, 37.7, 49.7, 50.3, 50.8, 52.6, 181.3; Elemental analysis calculated for $C_{60}H_{136}N_{14}O_{20}$: C, 52.45%; H, 9.97%; N, 14.27%. found C, 52.05%; H, 10.28%; N, 14.43%.

Results

Calcium or Renagel® bind phosphate in vivo. In previous measurements of intestinal phosphate absorption, $^{33}$P was administered in a 0.5 mM $KH_2PO_4$ buffer. However, when 0.5 mM $KH_2PO_4$ was mixed with 100 mM $CaCl_2$, that concentration of phosphate did not precipitate. This suggests that a higher concentration of $KH_2PO_4$ is needed for calcium to bind phosphate. In fact, to detect precipitation of phosphate by excess calcium, the level of phosphate needed to be raised to 10 mM (data not shown). Thus, to determine optimal conditions for testing oral phosphate binders in vivo, water, 20 mg calcium (as calcium acetate), or 14.4 mg Renagel® were administered to fasted rats. Rats were immediately administered an oral dose of $^{33}$P in a buffer containing 10, 50, or 100 mM $KH_2PO_4$ and killed after 60 minutes.

Figure 2A:
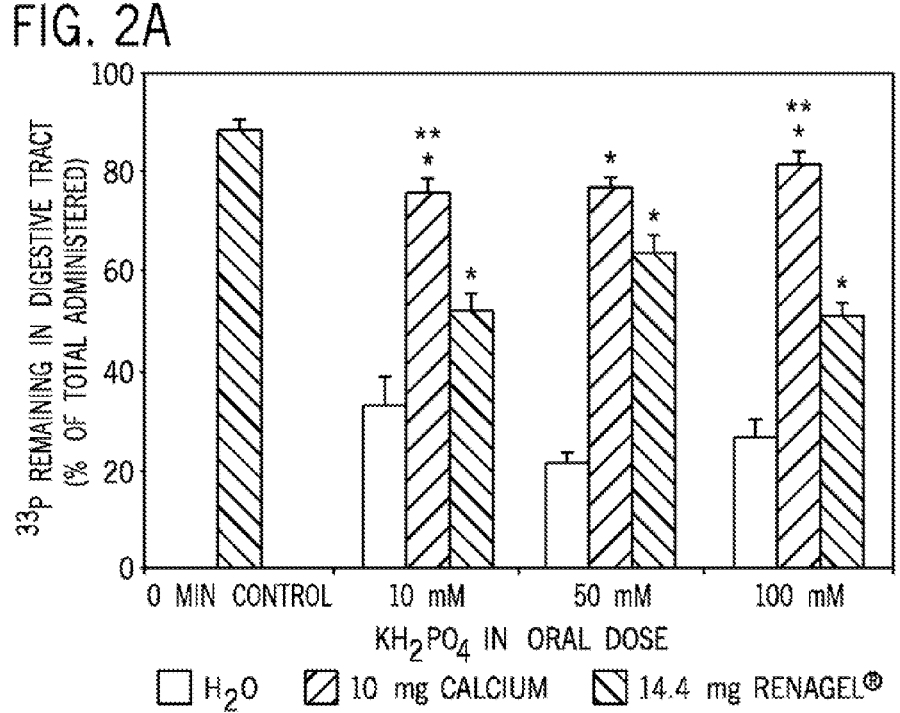
FIG. 2A) Percent of oral $^{33}$P dose remaining in the digestive tract. *Significantly different from rats administered water prior to $^{33}$P in same level of unlabeled phosphate ($p<0.05$). **Significantly different from rats administered 14.4 mg Renagel® prior to $^{33}$P in same level of unlabeled phosphate ($p<0.05$).
Figure 2B:
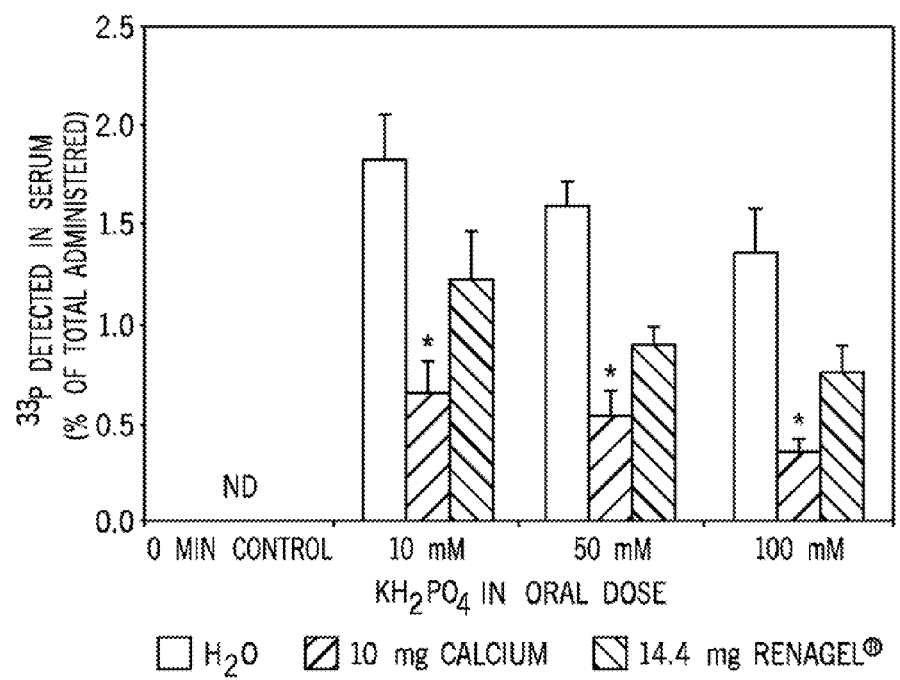
FIG. 2B) Percent of oral $^{33}$P dose detected in serum. *Significantly different from rats administered water prior to $^{33}$P in same level of unlabeled phosphate ($p<0.05$).
Figure 3A:
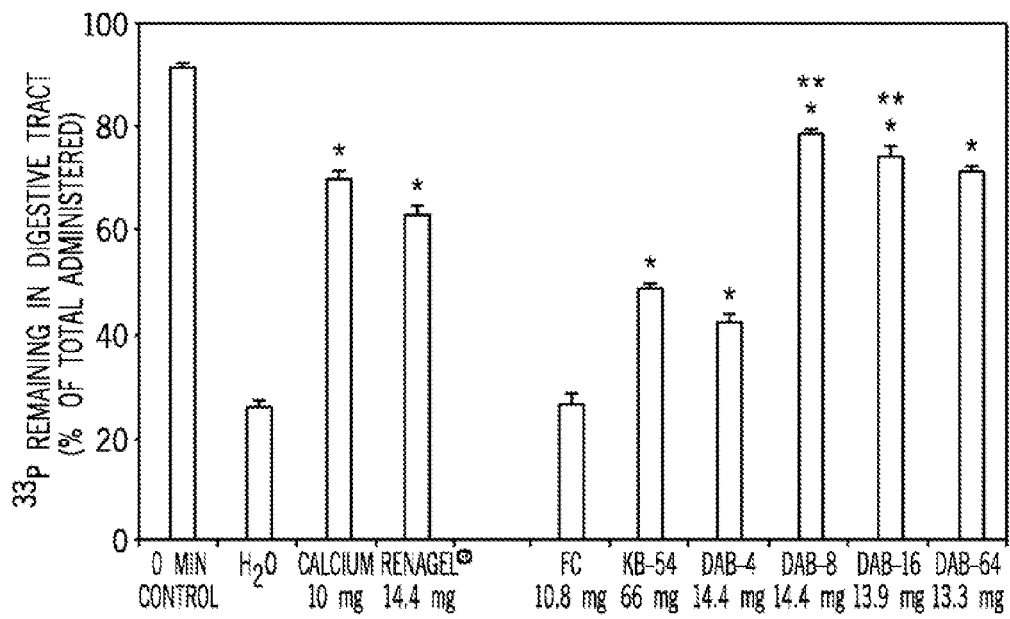
FIG. 3A) Percent of oral $^{33}$P dose remaining in the digestive tract.
Figure 3B:
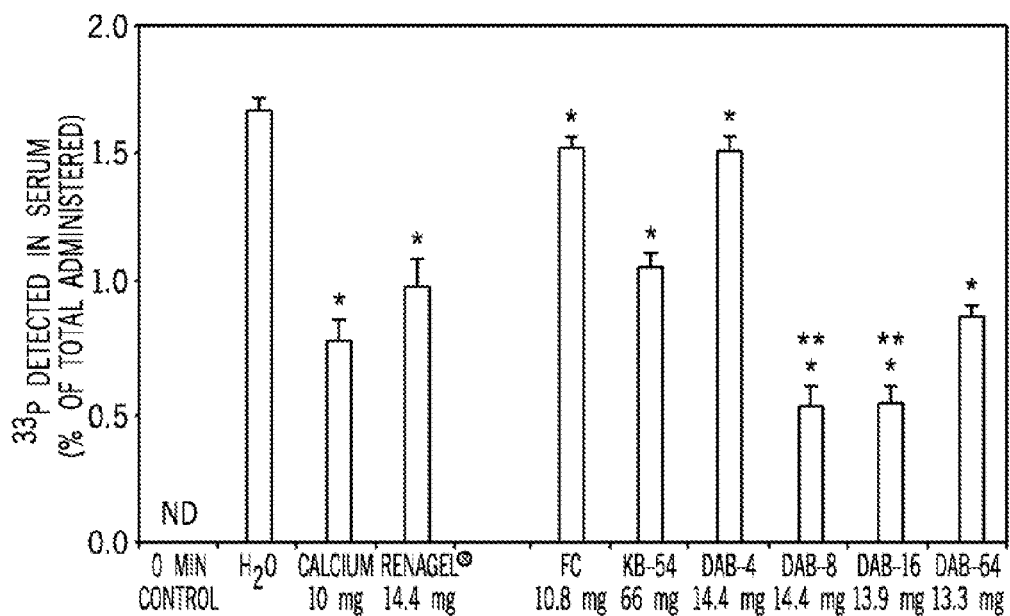
FIG. 3B) Percent of oral $^{33}$P dose detected in serum. *Significantly different from rats administered water prior to $^{33}$P ($p<0.05$). **Significantly different from rats administered Renagel® prior to $^{33}$P ($p<0.05$).

As shown in FIG. 2A, rats administered 20 mg calcium or 14.4 mg Renagel® prior to $^{33}$P had significantly more $^{33}$P remaining in the intestine after 60 minutes than rats administered water prior to $^{33}$P regardless of the level of unlabeled phosphate in the oral dose. Moreover, 20 mg calcium bound more $^{33}$P in the intestine than did 14.4 mg Renagel®, and this difference reached significance when $^{33}$P was administered in 10 or 100 mM phosphate. A significant decrease in serum $^{33}$P levels was also detected in rats dosed with 10 mg calcium, but the decrease in serum $^{33}$P levels observed in rats dosed with 14.4 mg Renagel® was not statistically significant (FIG. 2B).

Figure 4A:
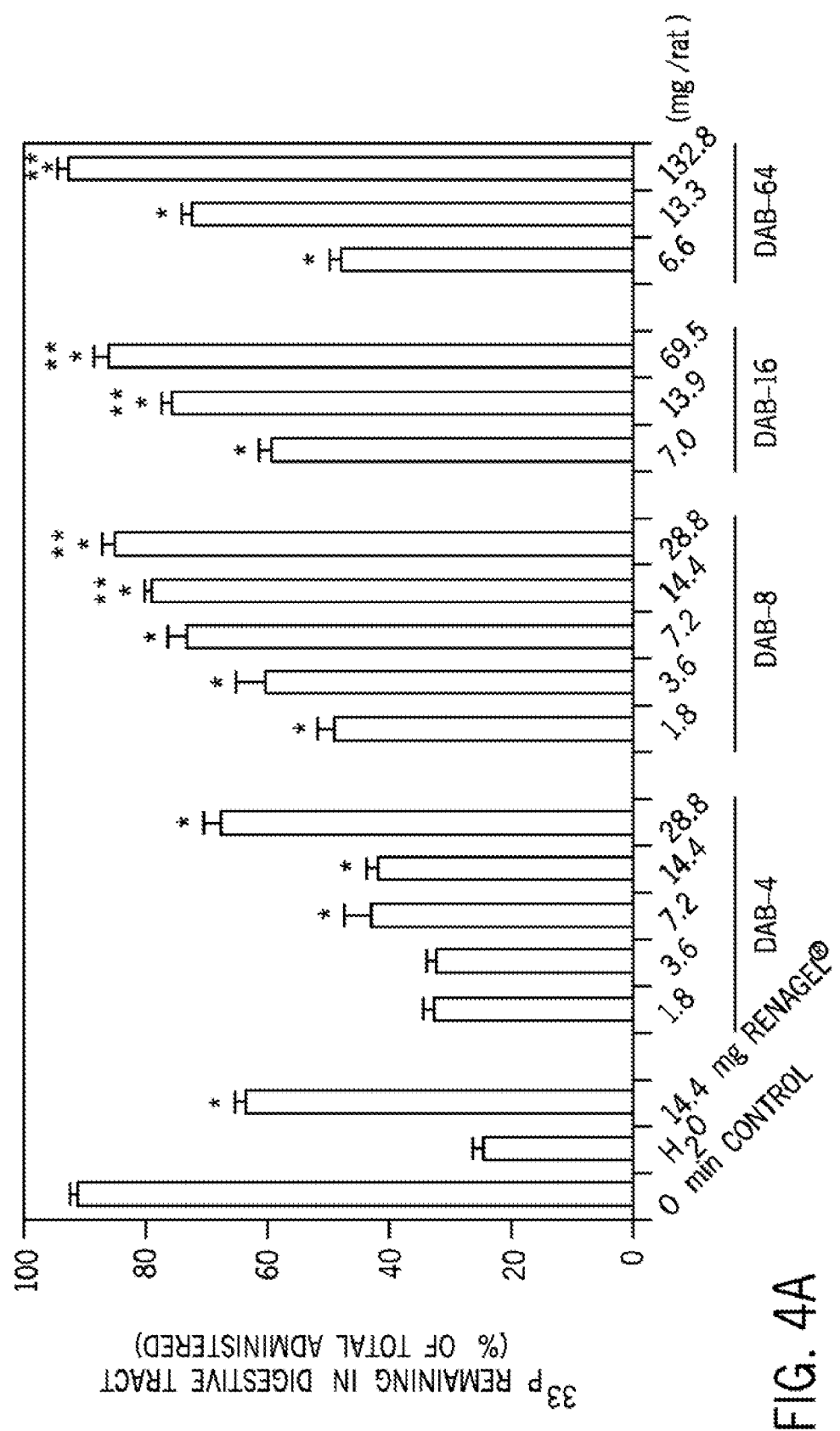
FIG. 4A) Percent of oral $^{33}$P dose remaining in the digestive tract.
Figure 4B:
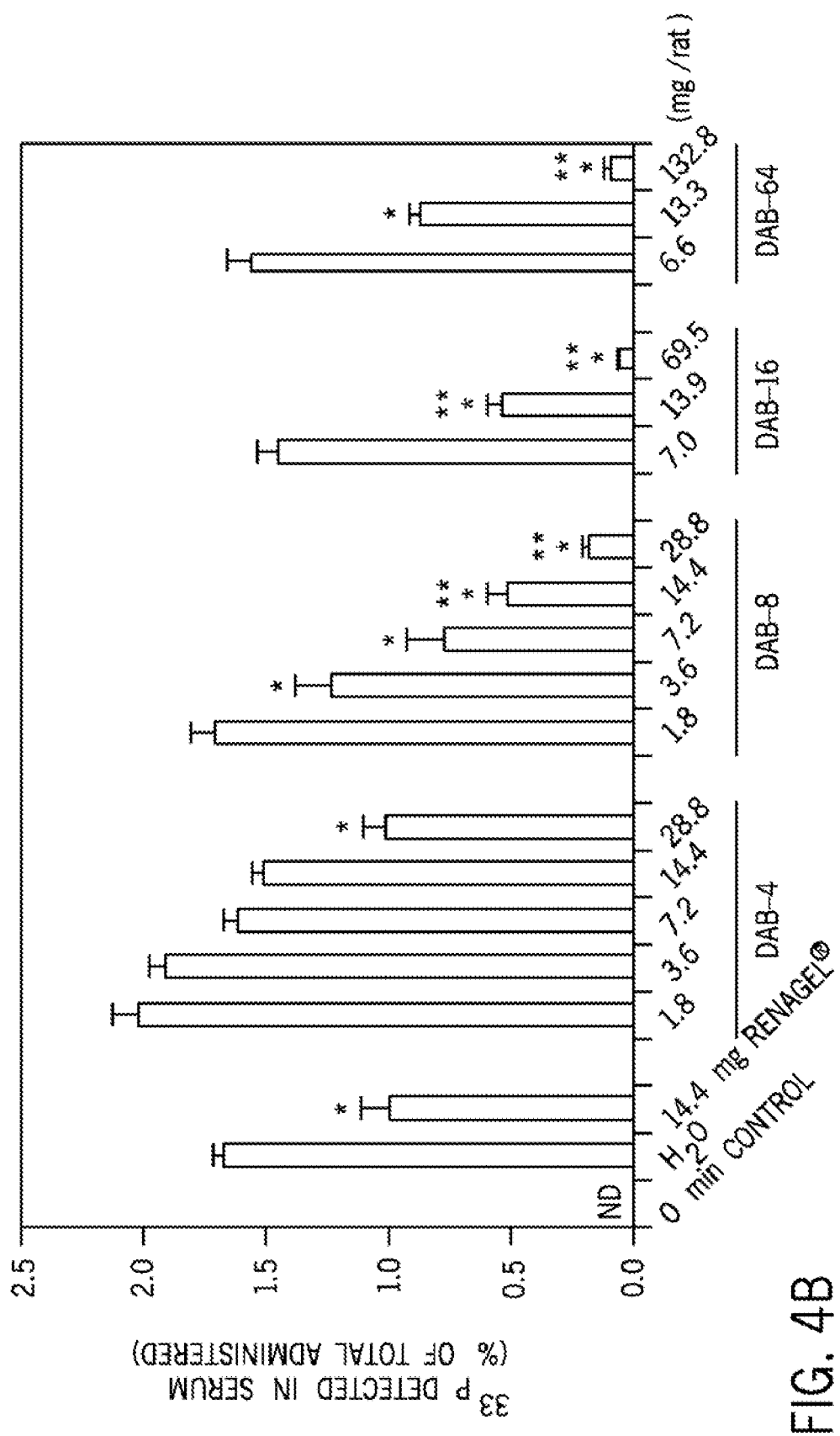
FIG. 4B) Percent of oral $^{33}$P dose detected in serum. *Significantly different from rats administered water prior to $^{33}$P ($p<0.05$). **Significantly different from rats administered Renagel® prior to $^{33}$P ($p<0.05$).

Comparison of novel oral phosphate binders. The binding ability of novel oral phosphate binders shown in FIG. 1 was compared to calcium and Renagel®. Table 1 lists the weight and molar amounts of all compounds used in this and subsequent experiments. Rats were first administered 0.5 mL water or 0.5 mL water containing 10 mg calcium (as calcium acetate), 14.4 mg Renagel®, or a novel phosphate binder. An oral dose of $^{33}$P in a 10 mM $KH_2PO_4$ buffer was immediately administered and rats were killed after 60 minutes. Both 10 mg calcium and 14.4 mg Renagel® significantly increased the amount of $^{33}$P remaining in the digestive tract (FIG. 4A), and significantly reduced serum $^{33}$P levels (FIG. 4B).

The novel binders KB-54 (Structure 2, FIG. 1B), DAB-4 (Structure 3, FIG. 1C), DAB-8 (Structure 4, FIG. 1D), DAB-16 (Structure 5, FIG. 1E) and DAB-64 (Structure 6, FIG. 1F) also significantly increased the amount of $^{33}$P remaining in the digestive tract and significantly reduced serum $^{33}$P levels. Furthermore, DAB-8-Cl (Structure 4, FIG. 1D) and DAB-16-Cl (Structure 5, FIG. 1E) significantly increased the amount of $^{33}$P remaining in the digestive tract and significantly reduced serum $^{33}$P levels compared to a comparable amount of Renagel®. FC (Structure 1, FIG. 1A) did not affect the amount of $^{33}$P that remained in the digestive tract, but caused a slight, but significant, decrease in serum $^{33}$P levels. Shown in Table 1 is a summary of solutions used to bind oral $^{33}$P dose. 0.5 mL of solution containing an oral phosphate binder was administered to rats prior to the oral $^{33}$P dose. NA=not available because structural information is proprietary.

TABLE 1

| Oral phosphate binder | mg/rat | moles/Liter (M) | Moles $NH_2$/Liter |
| --- | --- | --- | --- |
| Calcium acetate | 10 | 0.5 | 0 |
| Renagel ® | 14.4 | NA | NA |
| FC | 10.8 | 0.1 | 0.2 |
| KB-54 | 66 | 0.5 | 1.0 |
| DAB-4 | 1.8 | 0.00675 | 0.027 |
|  | 3.6 | 0.0135 | 0.054 |
|  | 7.2 | 0.027 | 0.108 |
|  | 10.7 | 0.04 | 0.160 |
|  | 14.4 | 0.054 | 0.216 |
|  | 28.8 | 0.108 | 0.432 |
| DAB-8 | 1.8 | 0.0028 | 0.0224 |
|  | 3.6 | 0.0056 | 0.0448 |
|  | 7.2 | 0.01 | 0.08 |
|  | 10.7 | 0.011 | 0.088 |
|  | 14.4 | 0.022 | 0.176 |
|  | 28.8 | 0.045 | 0.36 |
| DAB-16 | 6.95 | 0.005 | 0.08 |
|  | 13.9 | 0.01 | 0.16 |
|  | 69.5 | 0.05 | 0.8 |
| DAB-64 | 6.64 | 0.00115 | 0.0736 |
|  | 13.28 | 0.0023 | 0.1472 |
|  | 132.8 | 0.023 | 1.472 |

Dose response to dendrimer compound. The ability of DAB-4, DAB-8, DAB-16, and DAB-64 to bind phosphate was compared in a dose response study. Rats were first administered 0.5 mL water, 0.5 mL water containing 14.4 mg Renagel®, or a dendrimer. An oral dose of $^{33}$P in a 10 mM $KH_2PO_4$ buffer was immediately administered and rats were killed after 60 minutes. All dendrimer compounds increased $^{33}$P remaining in the digestive tract (FIG. 4A) and correspondingly decreased serum $^{33}$P (FIG. 4B) levels in a dose-dependent manner.

Nearly all the increases in $^{33}$P remaining in the digestive tract, and many of the decreases in serum $^{33}$P levels, were statistically significant. In addition, the two highest levels of DAB-8 and DAB-16, and the highest level of DAB-64, significantly increased $^{33}$P remaining in the intestine and significantly reduced serum $^{33}$P levels compared to Renagel®.

Mechanism underlying the dendrimer compound's ability to bind phosphate. To determine if the number of free amino groups in the dendrimer compound is responsible for its phosphate binding ability, rats were administered equal numbers of moles or free amino groups from DAB-4, DAB-8 and DAB-16. Rats were immediately administered an oral dose of $^{33}P$ in a 10 mM $KH_2PO_4$ buffer and killed after 60 minutes.

Figure 5A:
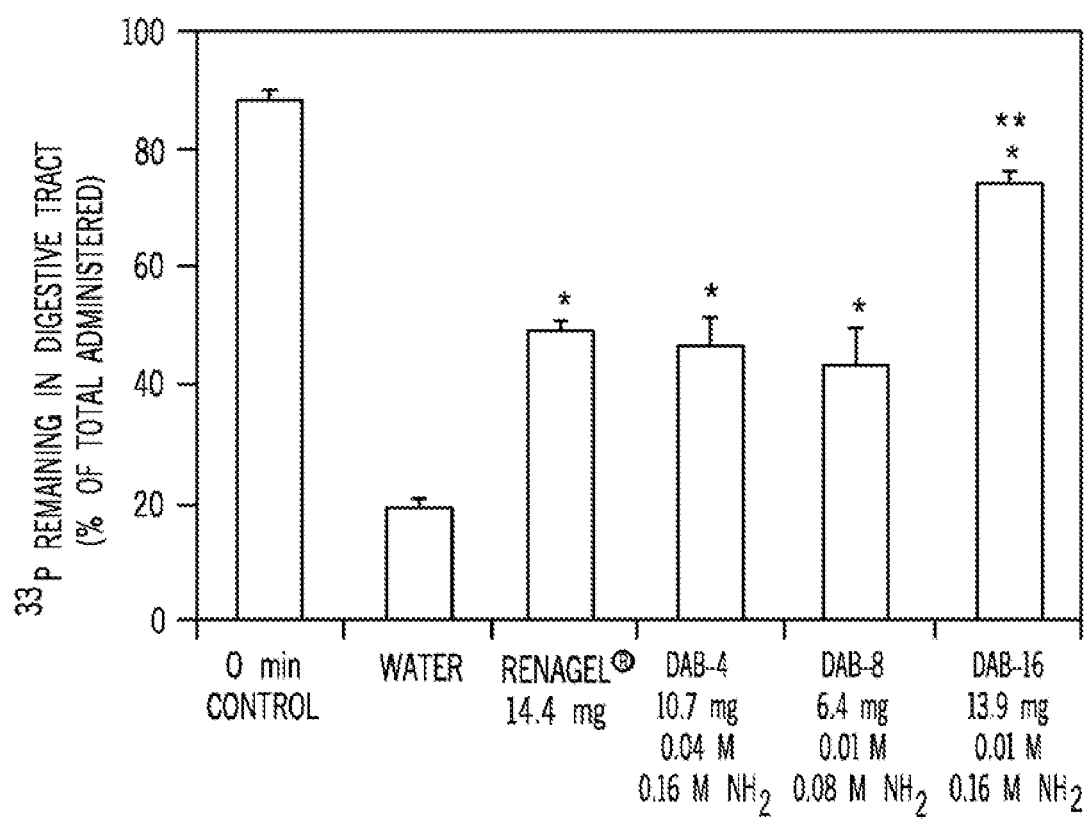
FIG. 5A) Percent of oral $^{33}$P dose remaining in the digestive tract.
Figure 5B:
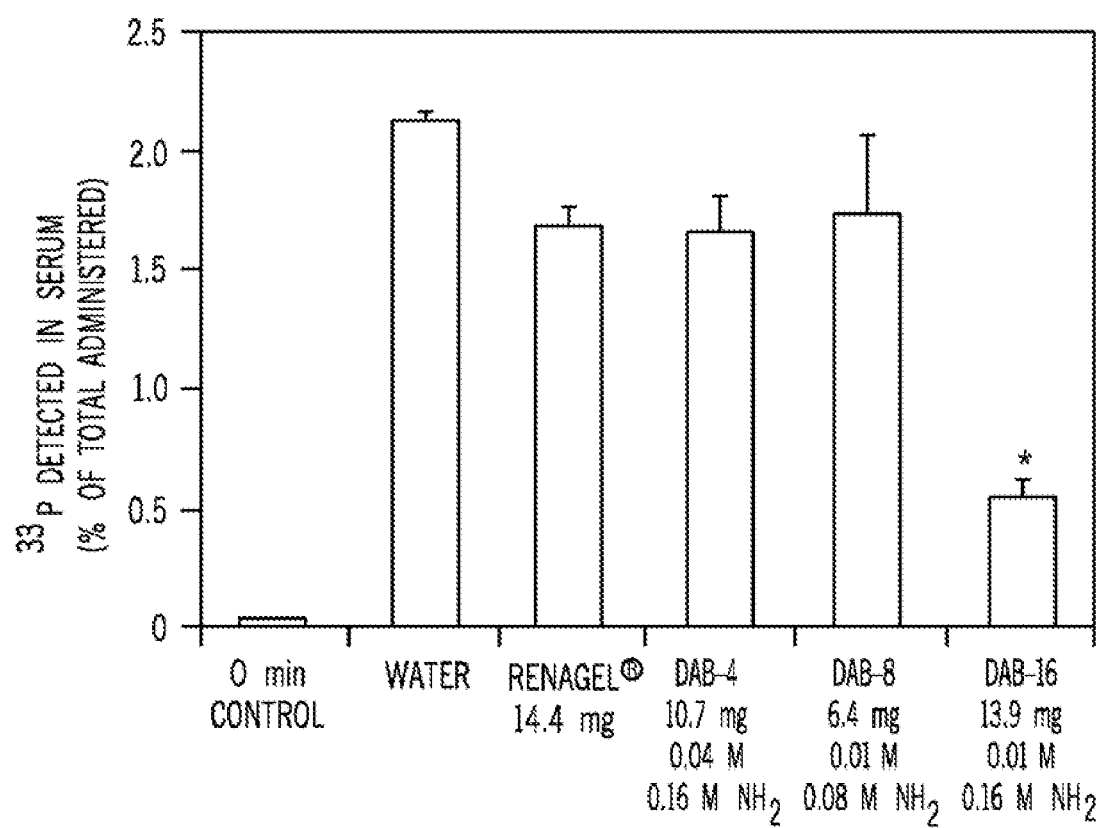
FIG. 5B) Percent of oral $^{33}$P dose detected in serum. *Significantly different from rats administered water prior to $^{33}$P ($p<0.05$). **Significantly different from rats administered Renagel® prior to $^{33}$P ($p<0.05$). ND=none detectable.

As seen in FIG. 5A, Renagel® and all levels of the dendrimers were able to increase the amount of $^{33}P$ remaining in the digestive tract to a significant degree. However, 13.9 mg DAB-16-Cl was the only level of binder able to significantly reduce serum $^{33}P$ levels (FIG. 5B). Interestingly, when an equivalent amount of free amino groups were added from DAB-4 and DAB-16, DAB-16 was able to retain significantly more $^{33}P$ in the digestive tract. In addition, when equimolar amounts of DAB-8-Cl and DAB-16-Cl were administered to rats, DAB-16-Cl retained significantly more $^{33}P$ in the digestive tract.

Rats were fed a purified control diet containing 0.47% calcium and 0.20% phosphorus or the same diet with added calcium, or 0.15% Renagel®, DAB-4, DAB-8, or DAB-16 for one week. Fecal samples were then collected for 48 hours, dried, and ashed. Ash was dissolved in acid to determine calcium and phosphorus levels. Fecal calcium levels were significantly increased in rats fed a 1.20% calcium diet, confirming that diets were mixed and administered correctly. Fecal phosphorus was increased, though not significantly, in rats fed a diet containing 1.20% calcium or 0.15% DAB-4. As shown in Table 2, rats fed 0.15% DAB-8 or DAB-16 had significantly increased fecal phosphorus levels compared to rats fed a control diet or a diet with 0.15% Renagel® according to Fisher's LSD test only.

Figure 13:
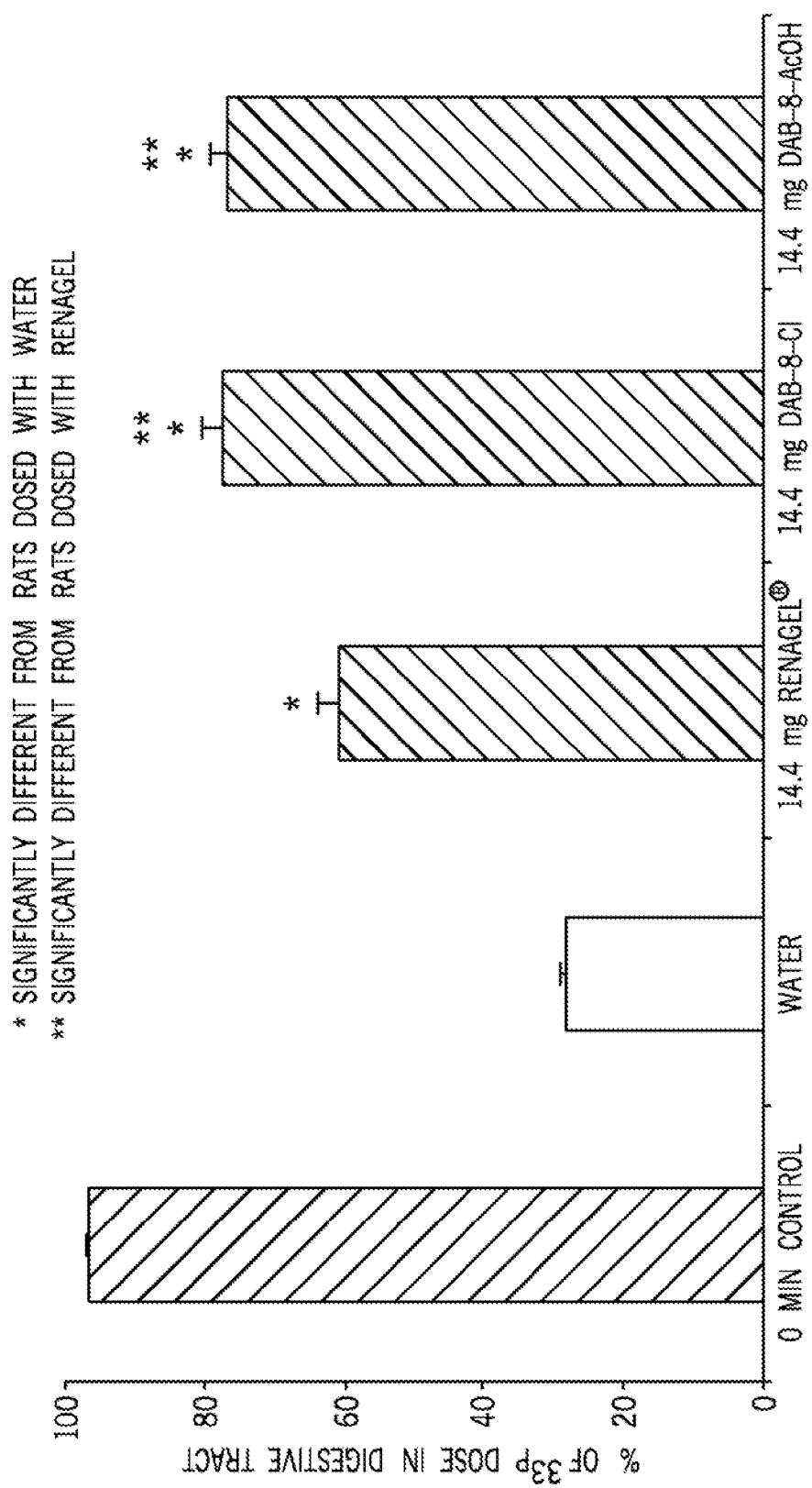
FIG. 13 illustrates the effect of hydroacetate dendrimers on intestinal $^{33}$P absorption.
Figure 14:
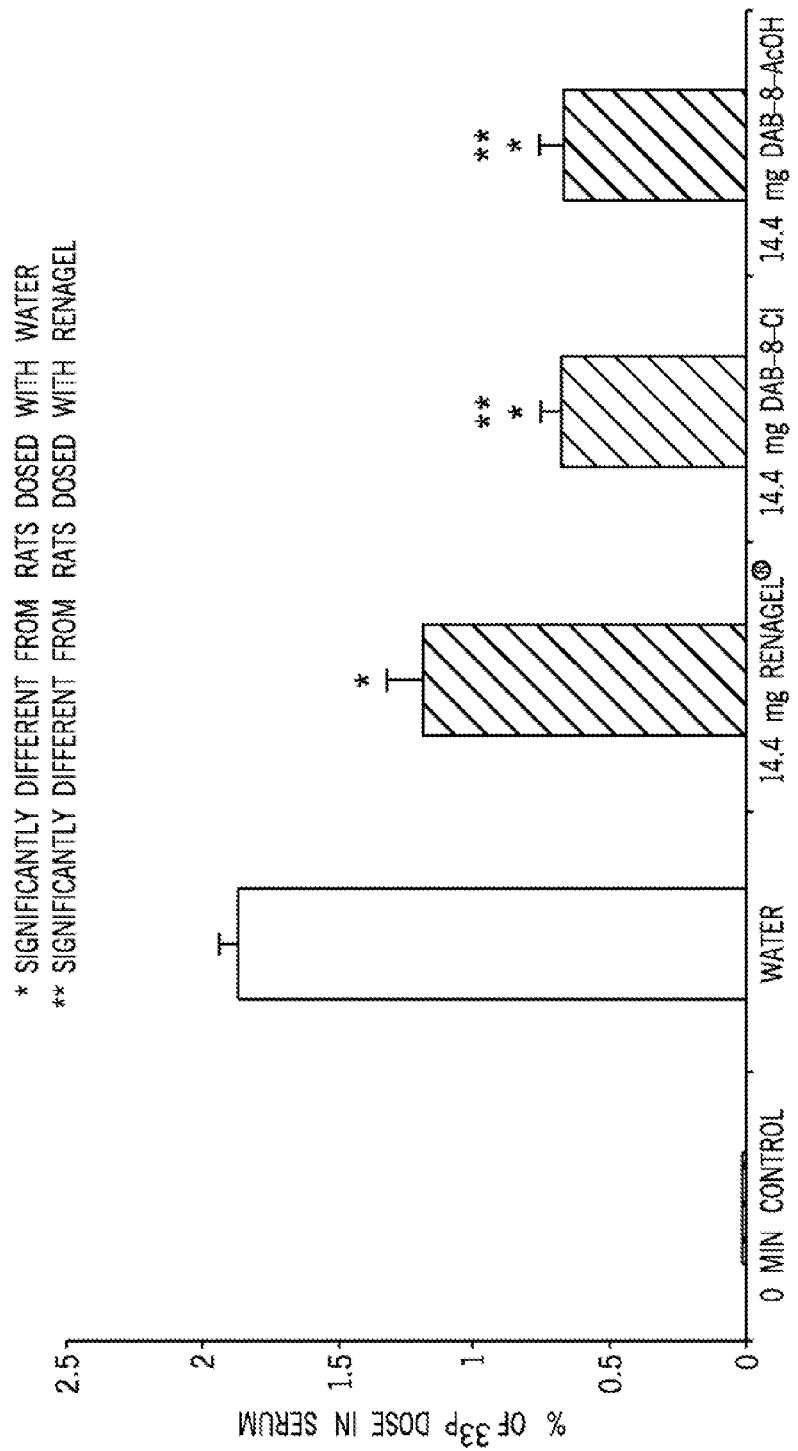
FIG. 14 illustrates the effect of hydroacetate dendrimers on absorption of $^{33}$P into serum.

As seen in FIGS. 13 and 14, hydroacetate dendrimers (such as structure 7, FIG. 1G) work just as effectively as the hydrochloride dendrimers. Shown in Table 2 is a demonstration of an increase in dendrimers in fecal phosphorus levels. Fecal calcium and phosphorus levels from rats fed a control diet containing 0.47% Ca and 0.2% P, or control diet with added calcium, Renagel®, DAB-4, DAB-8, or DAB-16. Data are presented as means±standard error of the means (SEM). *Significantly different from amount of calcium in feces from rats fed control diet (p<0.05). **Significantly different from amount of calcium in feces from rats fed control diet as detected by Fisher's LSD test only (p<0.05).

TABLE 2

| Group | mg Ca per gram feces | mg P per gram feces |
|---|---|---|
| Control | 11.23 ± 0.84 | 3.79 ± 0.18 |
| 1.20% Ca | 80.71 ± 4.60* | 4.39 ± 0.23 |
| 0.15% Renagel ® | 13.06 ± 1.08 | 3.69 ± 0.21 |
| 0.15% DAB-4 | 14.28 ± 2.01 | 4.30 ± 0.13 |
| 0.15% DAB-8 | 16.06 ± 1.44 | 4.71 ± 0.53** |
| 0.15% DAB-16 | 15.82 ± 1.52 | 4.78 ± 0.30** |

Figure 15:
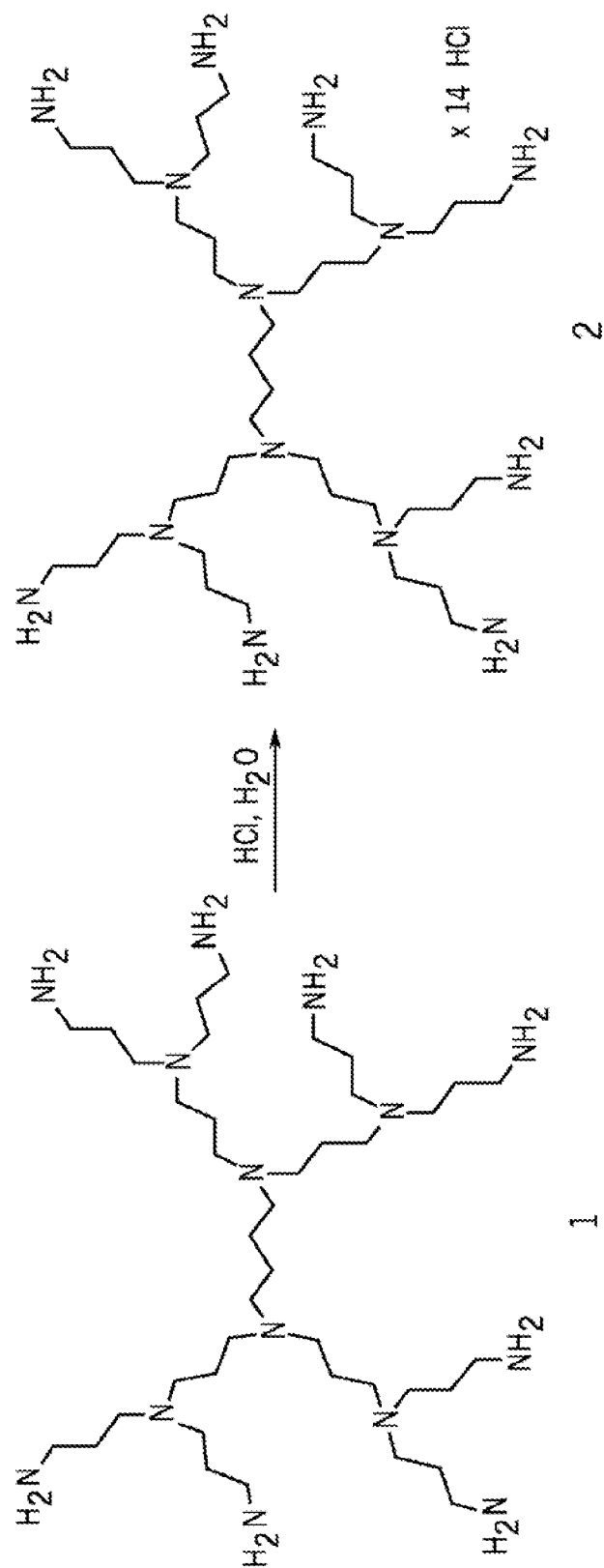
FIG. 15 illustrates the conversion of DAB-Am-8 Dendrimer (Generation 2.0) into polypropyleneimine octamine dendrimer perhydrochloride.

Shown in FIG. 15 is the conversion of DAB-Am-8 Dendrimer (Generation 2.0) into hydrochloride, which is also referred to as DAB-Am-8, Polypropylenimine octaamine Dendrimer perhydrochloride.

DAB-Am-8, Polypropylenimine octaamine Dendrimer (DSM product)(10 g, 12.93 mmol) was dissolved in deionized water (300 mL). Air was removed by purging with argon for 15 min. and solution of HCl (aqueous HCl—37.0%: 19.3 mL, 235.44 mmol; deionized water: 40 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (24 h) and finally in vacuum oven at 60° C. for 3 days to yield 16.44 g (12.81 mmol, 99%) of white crystalline compound (m.p. 153-155° C.).

$^1H$ NMR (400 MHz, $D_2O$): δ 1.94 (s, 4H), 2.18-2.23 (m, 16H), 2.26-2.34 (m, 8H), 3.16 (t, 16H, J=7.8 Hz), 3.41-3.43 (m, 36H); $^{13}C$ NMR (100 MHz, $D_2O$): δ 19.0, 20.6, 21.6, 36.4, 49.8, 49.9, 50.0, 52.6; Elemental analysis calculated for $C_{40}H_{110}N_{14}Cl_{14}$: C, 37.42%; H, 8.63%; N, 15.27%; Cl, 38.66%. found C, 35.81%; H, 9.22%; N, 14.52%; Cl, 37.66%. Ratio of elements indicates full conversion of amino groups into hydrochlorides: calculated Cl/C, 1.03; Cl/N, 2.53; C/N, 2.45. found Cl/C, 1.05; Cl/N, 2.59; C/N, 2.46.

Figure 16:
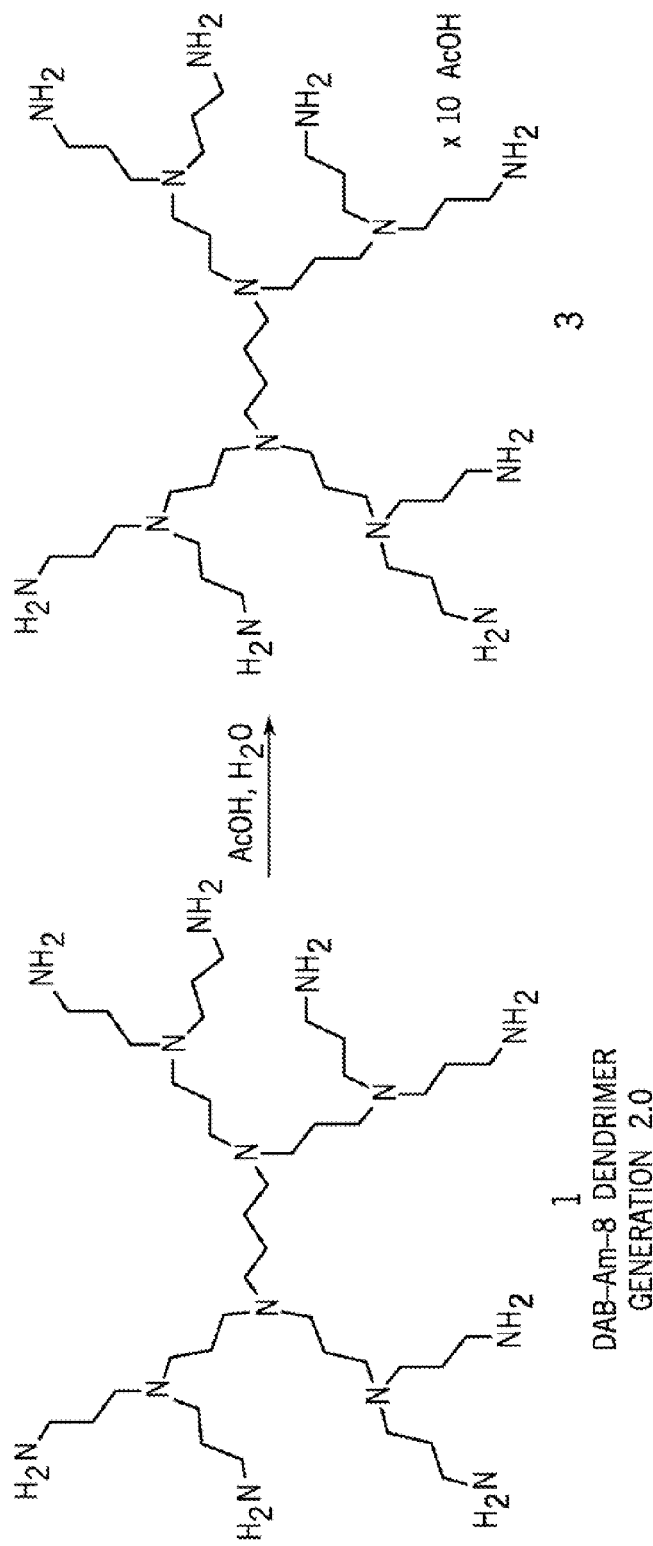
FIG. 16 illustrates the conversion of DAB-Am-8 Dendrimer (Generation 2.0) into polypropylenimine octaamine dendrimer decahydroacetate.

Shown in FIG. 16 is the conversion of DAB-Am-8 Dendrimer (Generation 2.0) into decahydroacetate, which is also referred to as DAB-Am-8, Polypropylenimine octaamine Dendrimer decahydroacetate.

DAB-Am-8, Polypropylenimine octaamine Dendrimer (DSM product)(6.92 g, 8.95 mmol) was dissolved in deionized water (260 mL). Air was removed by purging with argon for 15 min. and solution of AcOH (glacial AcOH: 8.0 mL, 137.86 mmol; deionized water: 160 mL) was added dropwise. Reaction mixture was stirred at room temperature for 12 h, and then solvents were removed under reduced pressure. Residue was dissolved in 250 mL of deionized water and evaporated (procedure was repeated sixteen times). Sample was dissolved in 100 mL of deionized water, frozen and lyophilized (48 h) to yield 11.78 g (8.57 mmol, 96%) of Polypropylenimine octaamine Dendrimer decahydroacetate as the very sticky pale orange oil.

$^1H$ NMR (400 MHz, $D_2O$): δ 1.63 (s, 4H), 1.74-1.85 (m, 24H), 1.88 (s, 30H), 2.52-2.62 (m, 24H), 2.86-3.02 (m, 28H); $^{13}C$ NMR (100 MHz, $D_2O$): δ 20.9, 21.7, 23.2, 23.4, 37.7, 49.7, 50.3, 50.8, 52.6, 181.3; Elemental analysis calculated for $C_{60}H_{136}N_{14}O_{20}$: C, 52.45%; H, 9.97%; N, 14.27%. found C, 52.05%; H, 10.28%; N, 14.43%.

Figure 17:
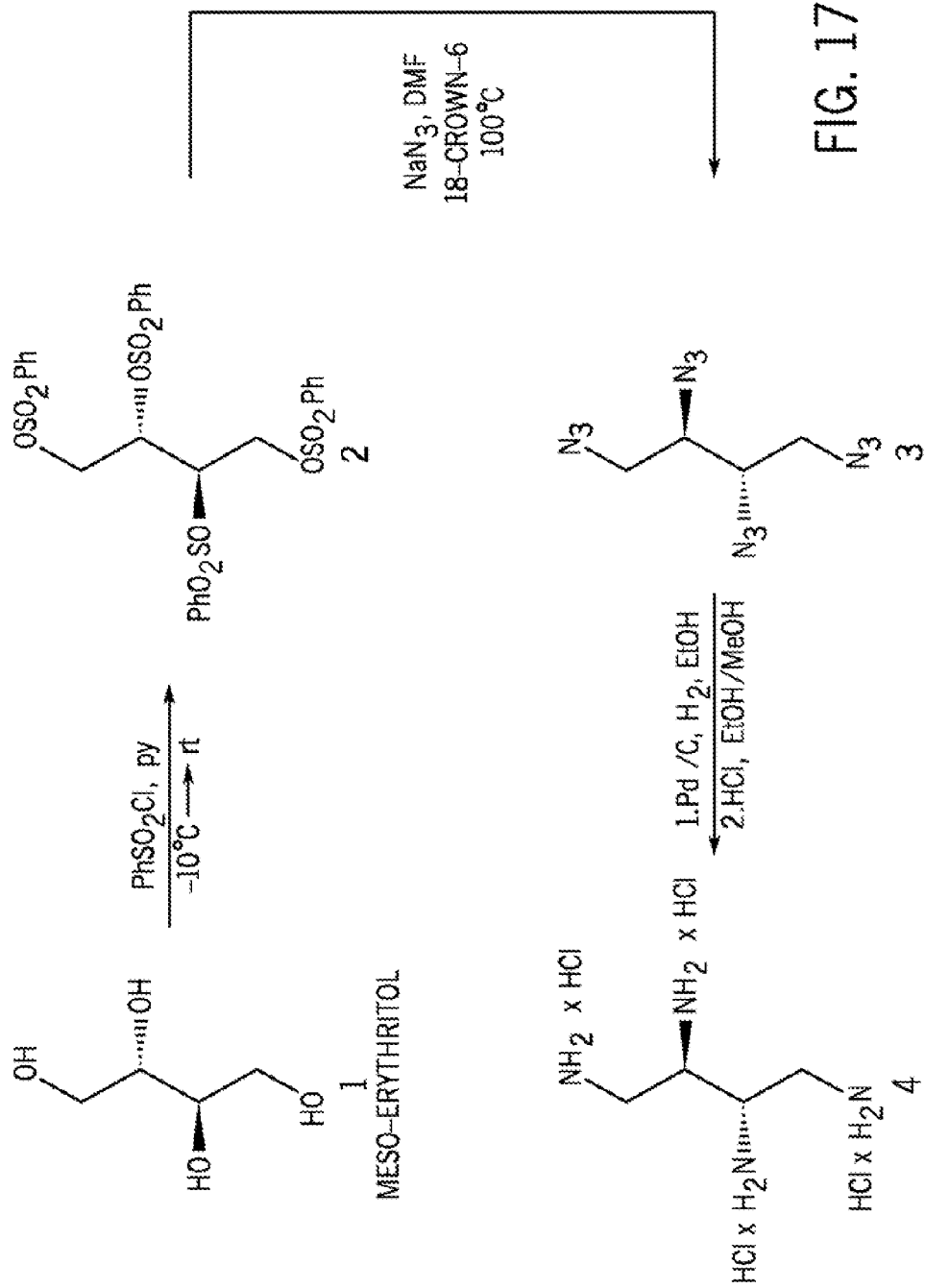
FIG. 17 illustrates the synthesis of erythro-1,2,3,4-tetraminobutane tetrahydrochloride.

Shown in FIG. 17 is the synthesis of erythro-1,2,3,4-tetraminobutane tetrahydrochloride. 1,2,3,4-Tetra-O-benzenesulfonyl-meso-erythritol is made from meso-Erythritol 1 (13 g, 106 mmol) which was dissolved in dry pyridine (400 mL). The solution was cooled down to −10° C. (salt-ice bath) and benzenesulfonyl chloride (81.5 mL, 640 mmol) was added dropwise over 1 h period. The cooling bath was removed and the mixture was stirred at room temperature for 5 h. The precipitate was collected and washed with ethyl acetate (250 mL), water (1 L) and again ethyl acetate (200 mL). After that the product was dried on air for 12 h and next in vacuum oven at 50° C. for 30 h to yield 27 g (39 mmol, 37% yield) of 1,2,3,4-Tetra-O-benzenesulfonyl-meso-erythritol as white crystals [m.p. 184-186° C., lit. m.p. 184-185.5° C. (See, R. L. Willer, *J. Org. Chem.*, 1984, 49:5150-5154). The organic filtrates were combined, concentrated to 200 mL and allowed to stand at room temperature to give next portion of crystalline product. Washing and drying procedures were repeated yielding in 30 g (44 mmol, 41% yield) of second portion of 1,2,3,4-Tetra-O-benzenesulfonyl-meso-erythritol (m.p. 183-185° C.). Total yield was 57 g (83 mmol, 78%). (See, R. L. Willer, *J. Org. Chem.*, 1984, 49, 5150-5154).

$^1H$ NMR (400 MHz, DMSO-d6): δ 4.03 (dd, 2H, J=6.6 Hz, J=11.5 Hz), 4.31 (d, 2H, J=11.5 Hz), 5.03 (d, 2H, J=6.7 Hz), 7.60-7.81 (m, 20H); $^{13}C$ NMR (100 MHz, DMSO-d6): δ 66.7, 76.7, 127.56, 129.7, 129.8, 134.3, 134.6, 134.7, 134.8; MS (ESI): exact mass calculated for $C_{28}H_{26}O_{12}S_4Na$ ([M+Na]$^+$) 705.0205. found 705.175.

Erythro-1,2,3,4-tetraazidobutane was made by providing 1,2,3,4-Tetra-O-benzenesulfonyl-meso-erythritol (27 g, 39 mmol), $NaN_3$ (17.17 g, 264 mmol), 18-crown-6 (0.5 g, 1.89 mmol) and dry DMF (220 mL) into a flask equipped with refluxing condenser. The reaction mixture was stirred at 100° C. for 48 h and then cooled down to room temperature, diluted with water (0.5 L) and washed with $CH_2Cl_2$ (7×200 mL).

Organic layers were combined, washed with water (8×100 mL) and saturated aqueous solution of NaCl (3×100 mL), dried over anhydrous $Na_2SO_4$, filtered and very carefully concentrated under reduced pressure. The dark brown residue, which contained still small amount of DMF, was purified by column chromatography (hexane, 5-10% ethyl acetate/hexane) to give 6.36 g (0.028 mmol, 72% yield) of erythro-1,2,3,4-tetraazidobutane as a colorless liquid. Because of well known hazards of polyazido compounds the product was partially concentrated under reduced pressure after chromatography and the residue of solvents was removed by purging a stream of argon for 2 h. (See, R. L. Willer, J. Org. Chem., 1984, 49, 5150-5154).

$^1$H NMR (400 MHz, $CDCl_3$): δ 3.52-3.58 (m, 4H), 3.67 (d, 2H, J=10.2 Hz); $^{13}$C NMR (100 MHz, $CDCl_3$): δ 52.0 and 61.5.

Erythro-1,2,3,4-tetraminobutane tetrahydrochloride was made by dissolving the erythro-1,2,3,4-tetraazidobutane (5.93 g, 26.7 mmol) was dissolved in 130 mL of ethanol and 1.5 g of 10% Pd/C was added. Air was removed by purging with argon for 15 min. The mixture was hydrogenated using a slow stream of hydrogen at room temperature for 5 h (TLC control, 10% ethyl acetate/hexane). After that mixture was filtered and celite. Flask and celite were washed with methanol (12 mL). Filtrate containing crude erythro-1,2,3,4-tetraminobutane was treated with solution of HCl (aqueous HCl-37.3%: 9.73 mL, 117.4 mmol; methanol: 34 mL) and stirred at room temperature for 12 h. Pale pink precipitate was then filtered off, washed with methanol (300 mL), dried on air for 12 h and next in vacuum oven at 60° C. for 48 h to give 4.84 g (18.3 mmol, after two steps 68% yield) of Erythro-1,2,3,4-tetraminobutane tetrahydrochloride (m.p. 255° C.; at 150° C. compound gets brown).

$^1$H NMR (400 MHz, $D_2O$): δ 3.20 (dd, 2H, J=8.6 Hz, J=14.0 Hz), 3.35 (dd, 2H, J=3.0 Hz, J=14.0 Hz), 3.75 (br d, 2H, J=9.3 Hz); $^1$H NMR (400 MHz, DMSO-d6): δ 3.31 (dd, 2H, J=7.2 Hz, J=14.2 Hz), 3.47 (dd, 2H, J=3.8 Hz, J=14.3 Hz), 4.08 (br d, 2H, J=8.9 Hz), 8.98 (br s, 12H); $^{13}$C NMR (100 MHz, $D_2O$): δ 39.0 and 50.3; $^{13}$C NMR (100 MHz, DMSO-d6): δ 38.2 and 49.9; Elemental analysis calculated for $C_4H_{18}N_4Cl_4$: C, 18.19%; H, 6.87%; N, 21.21%; Cl, 53.71%. found C, 18.37%; H, 7.01%; N, 21.29%; Cl, 53.46%.

Figure 18:
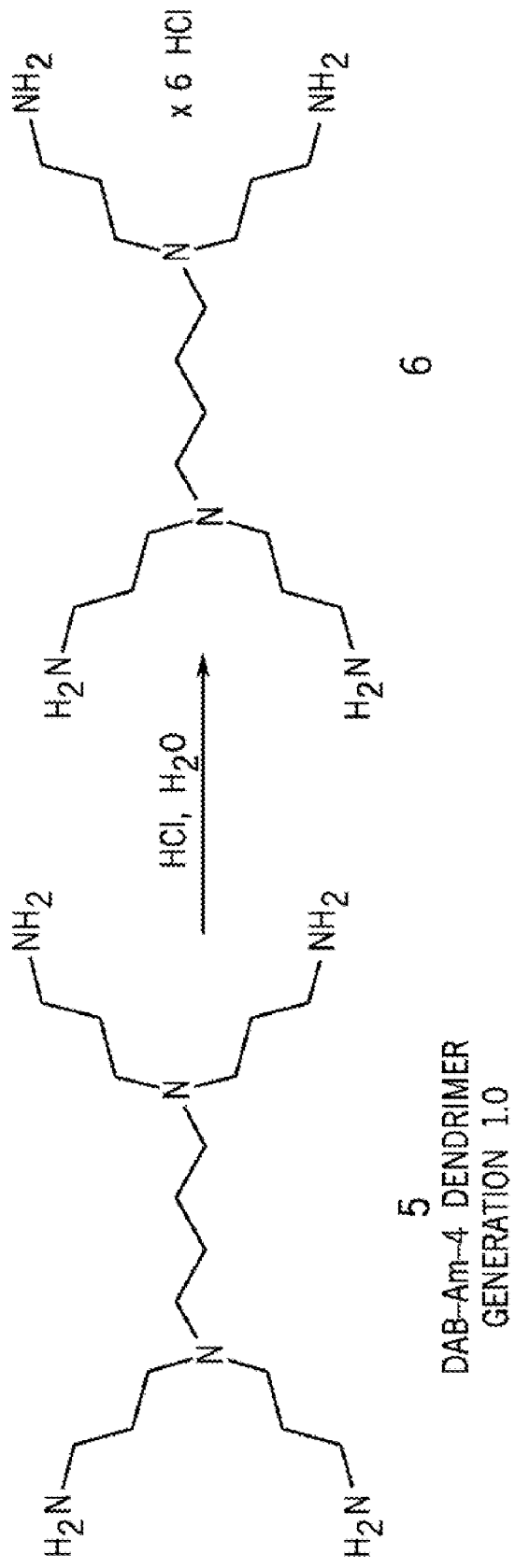
FIG. 18 illustrates the conversion of DAB-Am-4 Dendrimer (Generation 1.0) into polypropylenimine tetraamine dendrimer perhydrochloride.

Shown in FIG. 18 is the conversion of DAB-Am-4 Dendrimer (Generation 1.0) into polypropylenimine tetraamine Dendrimer perhydrochloride. DAB-Am-4, Polypropylenimine tetraamine Dendrimer (DSM product)(8.47 g, 26.76 mmol) was dissolved in deionized water (200 mL). Air was removed by purging with argon for 15 min and solution of HCl (aqueous HCl—37%: 15.85 mL, 193.02 mmol; deionized water: 30 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (48 h), then in vacuum oven at 60° C. for 2 days to yield 14.32 g (26.75 mmol, quantitative yield) of polypropylenimine tetraamine Dendrimer perhydrochloride as beige crystal (m.p. 242-245° C.).

$^1$H NMR (400 MHz, $D_2O$): δ 1.89 (s, 4H), 2.14-2.24 (m, 8H), 3.15 (t, 8H, J=7.5 Hz), 3.36-3.40 (m, 12H); $^{13}$C NMR (100 MHz, $D_2O$): δ 20.5, 21.6, 36.4, 49.9, 52.3; Elemental analysis calculated for $C_{16}H_{46}N_6Cl_6$: C, 35.90%; H, 8.66%; N, 15.69%; Cl, 39.73%. found C, 35.88%; H, 8.73%; N, 15.28%; Cl, 39.25%.

Figure 19:
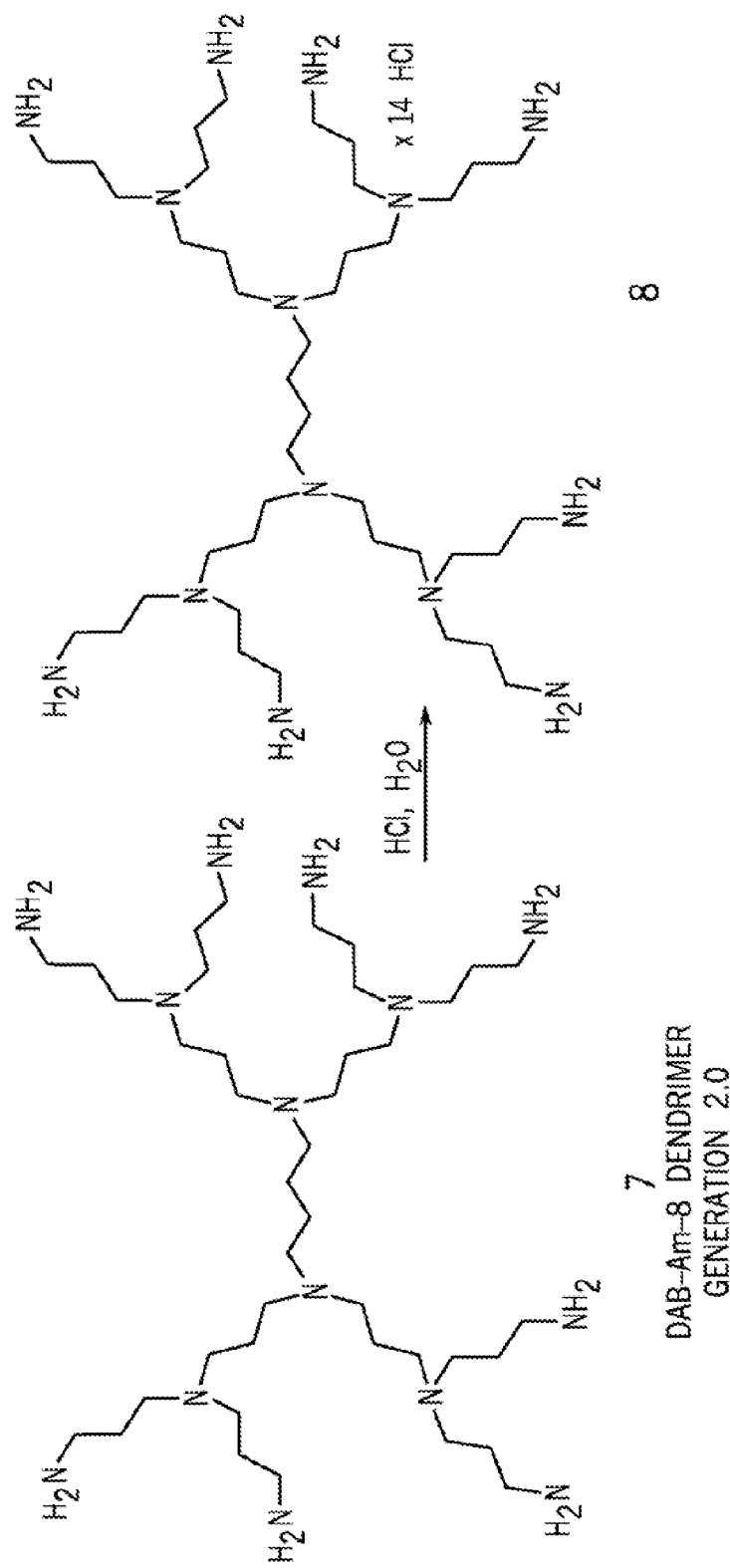
FIG. 19 illustrates the conversion of DAB-Am-8 Dendrimer (Generation 2.0) into polypropylenimine octaamine dendrimer perhydrochloride.

Shown in FIG. 19 is the conversion of DAB-Am-8 Dendrimer (Generation 2.0) into polypropylenimine octaamine Dendrimer perhydrochloride. DAB-Am-8, Polypropylenimine octaamine Dendrimer (DSM product) (10 g, 12.93 mmol) was dissolved in deionized water (300 mL). Air was removed by purging with argon for 15 min and solution of HCl (aqueous HCl—37.0%: 19.3 mL, 235.44 mmol; deionized water: 40 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (24 h) and finally in vacuum oven at 60° C. for 3 days to yield 16.44 g (12.81 mmol, 99%) of white crystalline polypropylenimine octaamine Dendrimer perhydrochloride (m.p. 153-155° C.).

$^1$H NMR (400 MHz, $D_2O$): δ 1.94 (s, 4H), 2.18-2.23 (m, 16H), 2.26-2.34 (m, 8H), 3.16 (t, 16H, J=7.8 Hz), 3.41-3.43 (m, 36H); $^{13}$C NMR (100 MHz, $D_2O$): δ 19.0, 20.6, 21.6, 36.4, 49.8, 49.9, 50.0, 52.6; Elemental analysis calculated for $C_{40}H_{110}N_{14}Cl_{14}$: C, 37.42%; H, 8.63%; N, 15.27%, $C_1$-38.66%. found C, 35.81%; H, 9.22%; N, 14.52%; Cl, 37.66%. Ratio of elements indicates full conversion of amino groups into hydrochlorides: calculated Cl/C, 1.03; Cl/N, 2.53; C/N, 2.45. found Cl/C, 1.05; Cl/N, 2.59; C/N, 2.46.

Figure 20:
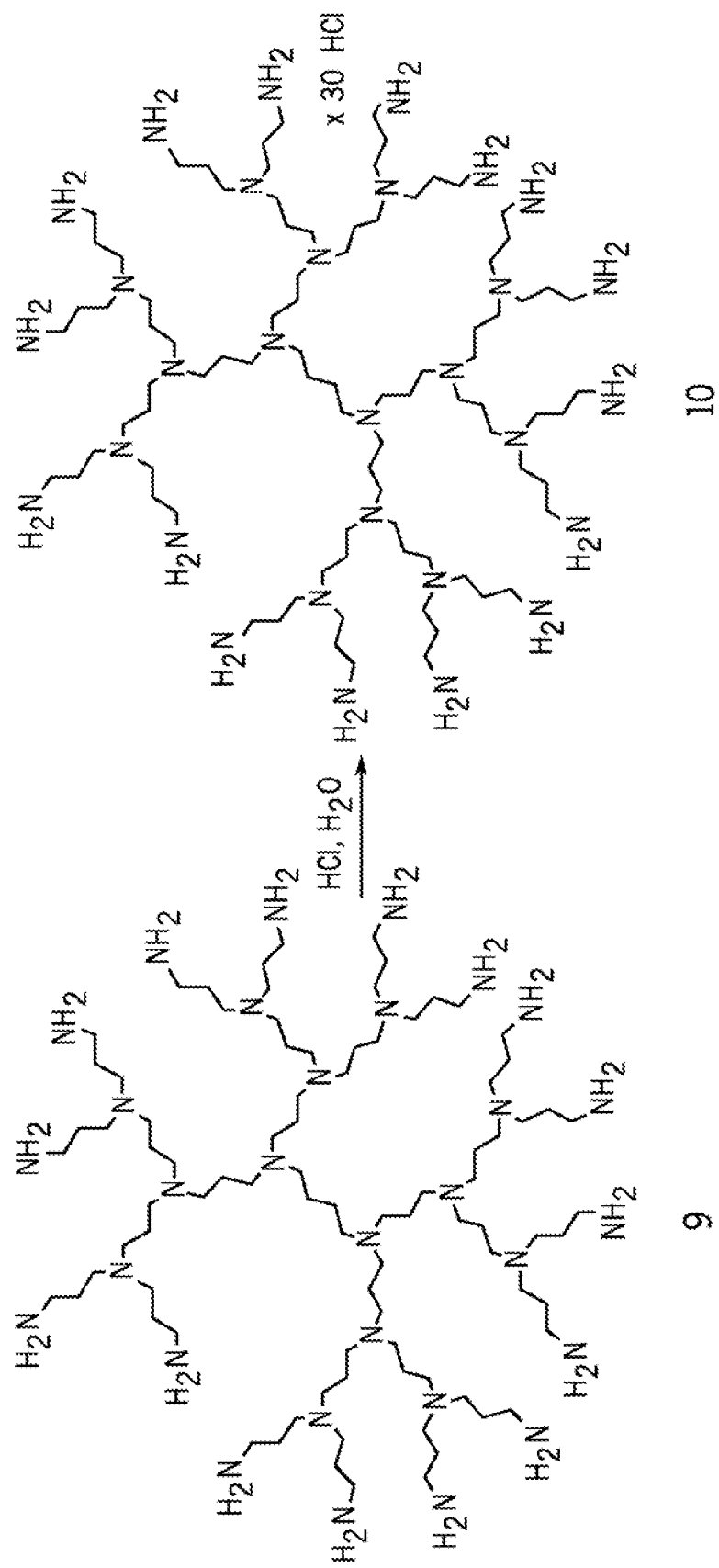
FIG. 20 illustrates the conversion of DAB-Am-16 Dendrimer (Generation 3.0) into polypropylenimine hexadecaamine dendrimer perhydrochloride.

Shown in FIG. 20 is the conversion of DAB-Am-16 Dendrimer (Generation 3.0) into Polypropylenimine hexadecaamine Dendrimer perhydrochloride. DAB-Am-16, Polypropylenimine hexadecaamine Dendrimer (DSM product)(5 g, 2.96 mmol) was dissolved in deionized water (150 mL). Air was removed by purging with argon for 15 min and solution of HCl (aqueous HCl—37%: 9.5 mL, 115.56 mmol; deionized water: 20 mL) was added dropwise. Reaction mixture was stirred at room temperature for 1 h and then solvents were removed under reduced pressure. Residue was dissolved in 150 mL of deionized water and evaporated (procedure was repeated five times), dried on vacuum pump (24 h) and finally in vacuum oven at 60° C. for 3 days to yield 8.24 g (2.96 mmol, quantitative yield) of creamy crystalline Polypropylenimine hexadecaamine Dendrimer perhydrochloride (m.p. 266° C.).

$^1$H NMR (600 MHz, $D_2O$): δ 1.81 (s, 4H), 2.07-2.10 (m, 32H), 2.14-2.19 (m, 24H), 3.06 (t, 32H, J=7.7 Hz), 3.28-2.37 (m, 84H); $^{13}$C NMR (100 MHz, $D_2O$): δ 19.0, 19.1, 20.7, 21.6, 36.4, 49.8, 49.9, 50.1, 50.3, 52.9; Elemental analysis calculated for $C_{88}H_{238}N_{30}Cl_{30}$: C, 38.01%; H, 8.63%; N, 15.11%; Cl, 38.25%. found C, 36.57%; H, 9.13%; N, 14.51%; Cl, 37.82%. Ratio of elements indicates full conversion of amino groups into hydrochlorides: calculated Cl/C, 1.01; Cl/N, 2.53; C/N, 2.51. found Cl/C, 1.03; Cl/N, 2.60; C/N, 2.52.

Figure 21:
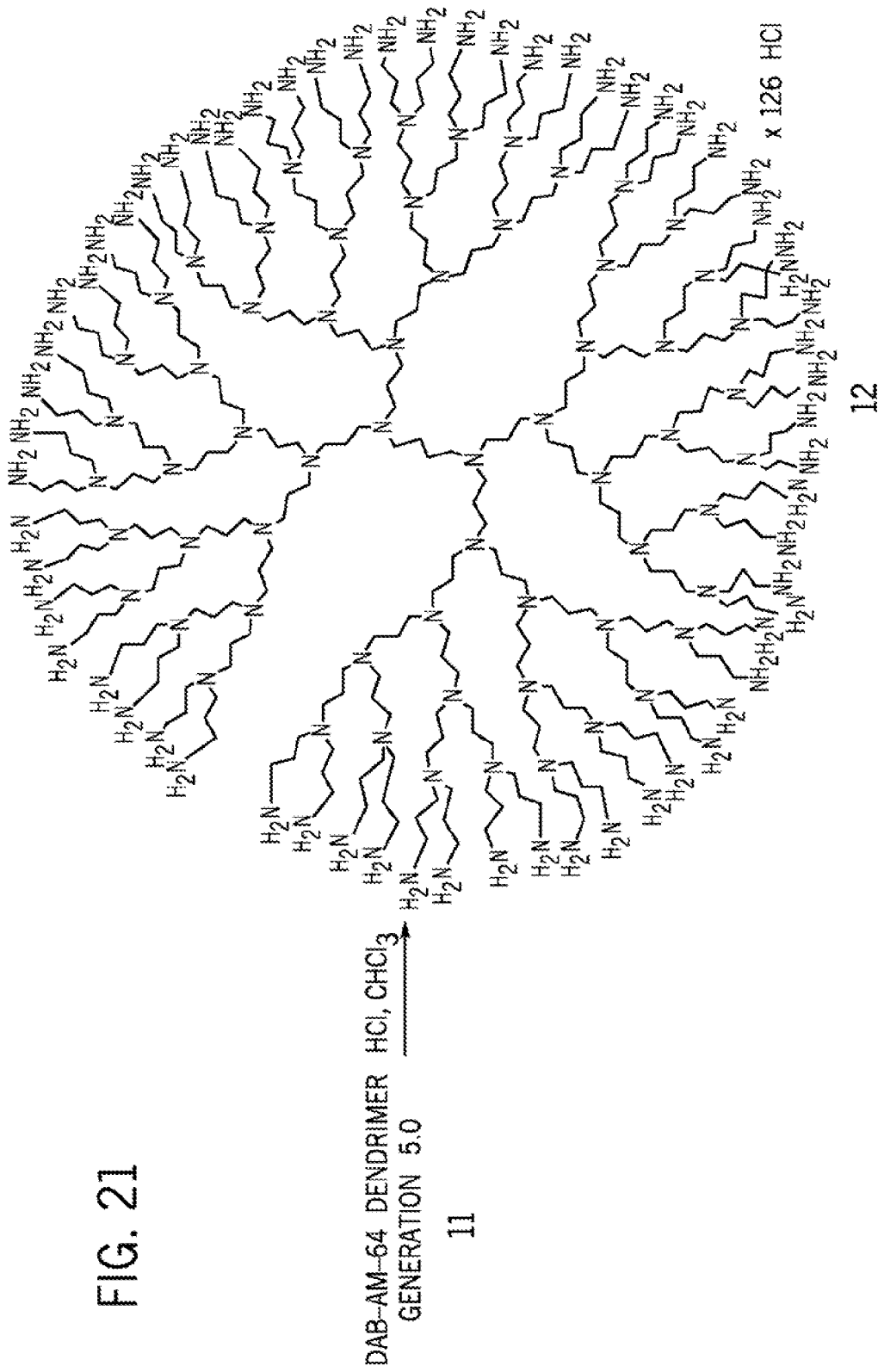
FIG. 21 illustrates the conversion of DAB-Am-64 (Generation 5.0) into polypropylenimine tetrahexacontaamine dendrimer perhydrochloride.

Shown in FIG. 21 is the conversion of DAB-Am-64 Dendrimer (Generation 5.0) into Polypropylenimine tetrahexacontaamine Dendrimer perhydrochloride. DAB-Am-64, Polypropylenimine tetrahexacontaamine Dendrimer (DSM product)(1.03 g, 0.14 mmol) was dissolved in $CH_3Cl$ (25 mL). Air was removed by purging with argon for 15 min and concentrated solution of HCl (aqueous HCl-37.3%: 1.66 mL, 19.99 mmol) was added dropwise. Reaction mixture was stirred at room temperature for 1 h and then solvents were removed under reduced pressure. The residue was dissolved in 20 mL of deionized water and evaporated (procedure was repeated five times), dried on vacuum pump (5 h) and finally in vacuum oven at 60° C. for 3 days to yield 1.525 g (0.13 mmol, 95% yield) of yellow crystalline Polypropylenimine tetrahexacontaamine Dendrimer perhydrochloride (m.p. 274-276° C.).

$^1$H NMR (600 MHz, $D_2O$): δ 1.79 (s, 4H), 2.11-2.19 and 2.23-2.34 (2×m, 248H), 3.09 (t, 128H, J=7.6 Hz), 2.32-2.47 (m, 372H); $^{13}$C NMR (100 MHz, $D_2O$)—only easy visible signals: δ 19.2, 19.3, 20.9, 21.8, 36.7, 49.3, 49.7, 49.9, 50.3, 51.0; Elemental analysis calculated for $C_{376}H_{1006}N_{126}Cl_{126}$: C, 38.39%; H, 8.62%; N, 15.00%; Cl, 37.97%. found C, 38.43%; H, 9.15%; N, 15.05%; Cl, 38.35%. Ratio of elements indicates full conversion of amino groups into hydrochlorides: calculated Cl/C, 0.99; Cl/N, 2.53, C/N, 2.55. found Cl/C, 0.99; Cl/N, 2.54; C/N, 2.55.

Figure 22:
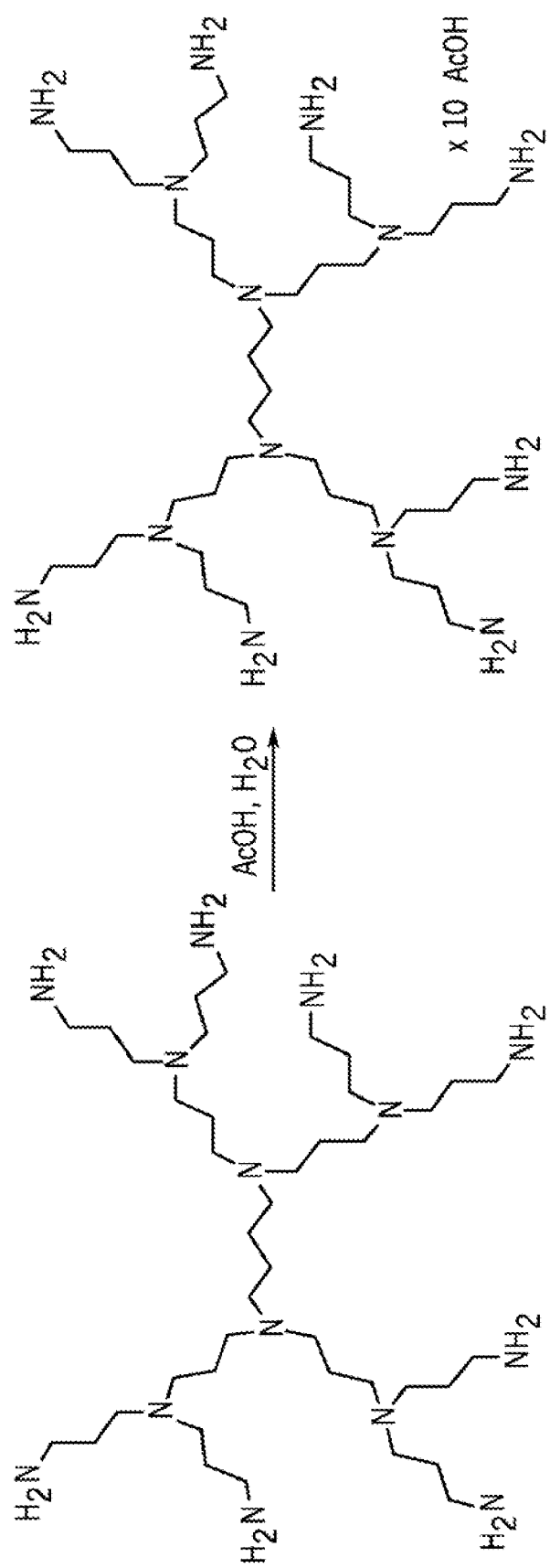
FIG. 22 illustrates the conversion of DAB-Am-8 Dendrimer (Generation 2.0) into polypropylenimine octaamine dendrimer decahydroacetate.

Shown in FIG. 22 is the conversion of DAB-Am-8 Dendrimer (Generation 2.0) into Polypropylenimine octaamine Dendrimer decahydroacetate. DAB-Am-8, Polypropylenimine octaamine Dendrimer (DSM product)(6.92 g, 8.95 mmol) was dissolved in deionized water (260 mL). Air was removed by purging with argon for 15 min and solution of AcOH (glacial AcOH: 8.0 mL, 137.86 mmol; deionized water: 160 mL) was added dropwise. Reaction mixture was stirred at room temperature for 12 h and then solvents were removed under reduced pressure. Residue was dissolved in 250 mL of deionized water and evaporated (procedure was repeated sixteen times). Finally, sample was dissolved in 100 mL of deionized water, frozen and lyophilized (48 h) to yield 11.78 g (8.57 mmol, 96%) of Polypropylenimine octaamine Dendrimer decahydroacetate as the very sticky pale orange oil.

$^1$H NMR (400 MHz, D$_2$O): δ 1.63 (s, 4H), 1.74-1.85 (m, 24H), 1.88 (s, 30H), 2.52-2.62 (m, 24H), 2.86-3.02 (m, 28H); $^{13}$C NMR (100 MHz, D$_2$O): δ 20.9, 21.7, 23.2, 23.4, 37.7, 49.7, 50.3, 50.8, 52.6, 181.3; Elemental analysis calculated for $C_{60}H_{136}N_{14}O_{20}$: C, 52.45%; H, 9.97%; N, 14.27%. found C, 52.05%; H, 10.28%; N, 14.43%.

Figure 23:
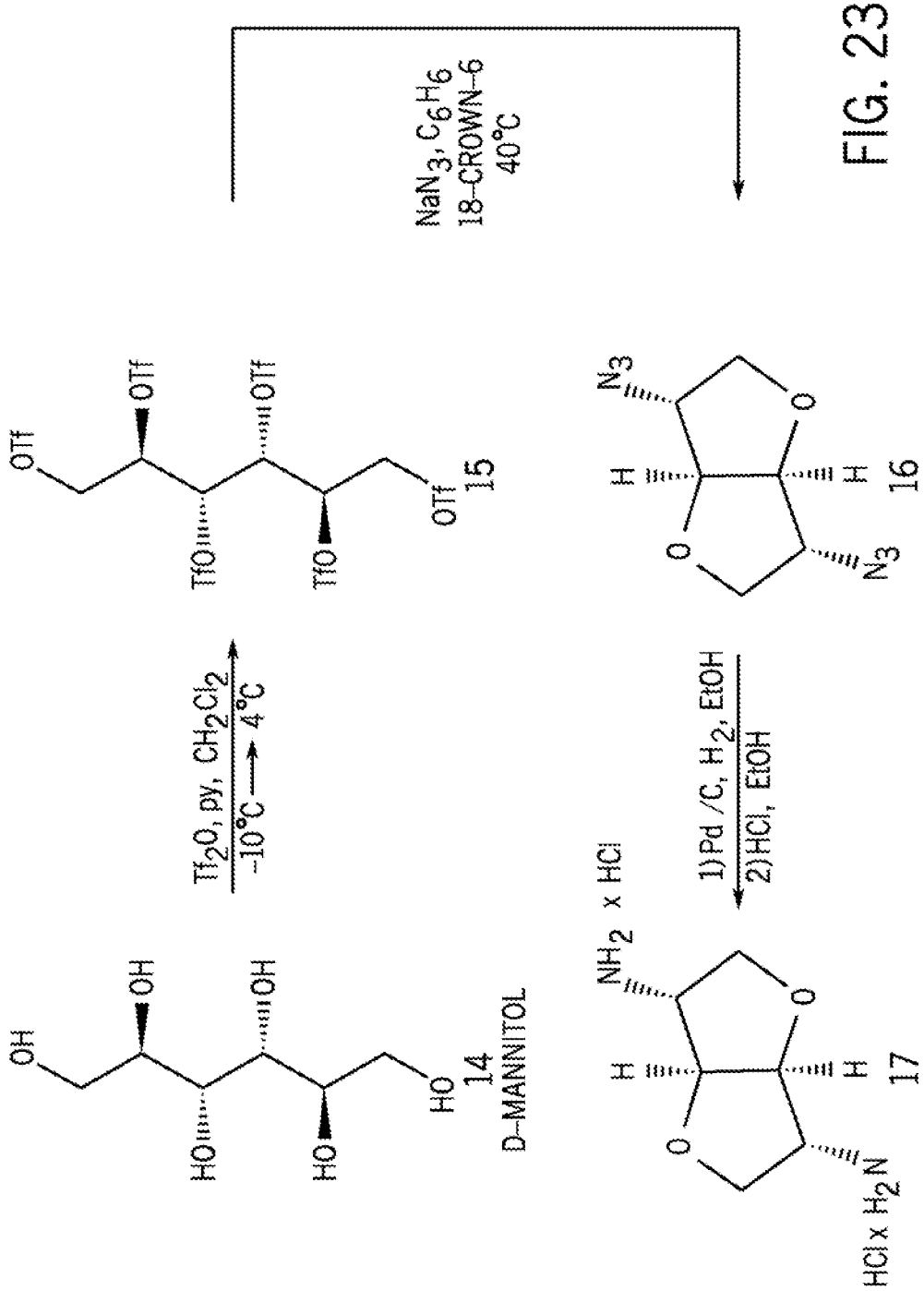
FIG. 23 illustrates the synthesis of 1,4:3,6-dianhydro-2,5-diamino-2,5-dideoxy-D-iditol dihydrochloride.

Shown in FIG. 23 is the synthesis of 1,4:3,6-Dianhydro-2,5-diamino-2,5-dideoxy-D-iditol dihydrochloride. To make 1,2,3,4,5,6-Hexa-O-trifluoromethanesulfonyl-D-mannitol, a suspension of D-Mannitol (174 mg, 0.95 mmol) in dry pyridine (4 mL, 49.4 mmol) was stirred under argon at room temperature 0.5 h. Then dry dichloromethane (14 mL) was added, a mixture was cooled down to −10° C. (salt-ice bath) and triflic anhydride (1.15 mL, 6.86 mmol) was added dropwise over 0.5 h period. Stirring was continued at 4° C. (cold room) for 12 h. The solution was diluted with dichloromethane (20 mL) and washed with water (6×7 mL), saturated aqueous solution of CuSO$_4$ (7 mL), again water (3×7 mL) and dried over anhydrous Na$_2$SO$_4$, filtered. Evaporation of the solvents, then very fast column chromatography (30% hexane/ethyl acetate) afforded an unstable, creamy semisolid product of 1,2,3,4,5,6-Hexa-O-trifluoromethanesulfonyl-D-mannitol (139 mg, 0.14 mmol, 15% yield).

[α]$_D$+97.9 (c 1.0, CHCl$_3$); $^1$H NMR (400 MHz, CDCl$_3$): δ 4.15 (m, 4H), 4.77 (dd, 2H, J=4.1 Hz, J=8.1 Hz), 5.21 (dd, 2H, J=4.3 Hz, J=9.3 Hz); $^{13}$C NMR (100 MHz, CDCl$_3$): δ 70.9, 80.4, 80.45, 118.5 (q, J$_{C,F}$=318.9 Hz).

1,4:3,6-Dianhydro-2,5-diazido-2,5-dideoxy-D-iditol was made by dissolving 1,2,3,4,5,6-Hexa-O-trifluoromethanesulfonyl-D-mannitol (120 mg, 0.123 mmol) and NaN3 (72 mg, 1.107 mmol) in dry benzene (2 mL). The 18-crown-6 (0.95 g, 0.36 mmol) was added and the reaction mixture was stirred under argon at 40° C. for 3 h, then cooled down to room temperature, diluted with CH$_2$Cl$_2$ (10 mL) and washed with water (6×4 mL). Organic layer was dried over anhydrous Na$_2$SO$_4$, filtered and very carefully concentrated under reduced pressure. The residue was purified by column chromatography (20% ethyl acetate/hexane). After chromatography solvents were removed under reduced pressure and finally by purging a stream of argon for 1 h to give 1,4:3,6-Dianhydro-2,5-diazido-2,5-dideoxy-D-iditol as colorless oil (20 mg, 0.102 mmol, 83% yield).

$^1$H NMR (400 MHz, CDCl$_3$): δ 3.89 (dd, 2H, J=4.0 Hz, J=10.2 Hz), 3.93 (dd, 2H, J=1.5 Hz, J=10.1 Hz), 4.06 (dd, 2H, J=1.2 Hz, J=3.8 Hz); $^{13}$C NMR (100 MHz, CDCl$_3$): δ 65.7, 71.9, 86.0.

1,4:3,6-Dianhydro-2,5-diamino-2,5-dideoxy-D-iditol dihydrochloride was made by dissolving 1,4:3,6-Dianhydro-2,5-diazido-2,5-dideoxy-D-iditol (20 mg, 0.102 mmol) in 2 mL of ethanol and 10 mg of 10% Pd/C was added. Air was removed by purging with argon for 15 min. The mixture was hydrogenated using a slow stream of hydrogen at room temperature for 3 h (TLC control, 20% ethyl acetate/hexane). After that, the mixture was filtered through celite. Flask and celite were washed with ethanol (10 mL). Filtrate containing crude 1,4:3,6-dianhydro-2,5-diamino-2,5-dideoxy-D-iditol was treated with solution of HCl (aqueous HCl—37.3%: 35 μL, 0.432 mmol; ethanol: 1.2 mL) and stirred at room temperature for 2 h. Precipitate was then filtered off, washed with ethanol (15 mL), dried on air for 12 h and next in vacuum oven at 60° C. for 48 h to give 13 mg (0.06 mmol, after two steps 59% yield) of 1,4:3,6-Dianhydro-2,5-diamino-2,5-dideoxy-D-iditol dihydrochloride as a white crystal (m.p. above 270° C.; at 250° C. compound gets dark grey).

[α]$_D$+55.2 (c 1.1, H$_2$O); $^1$H NMR (400 MHz, D$_2$O): δ 4.01-4.07 (m, 4H), 4.22 (dd, 2H, J=5.1 Hz, J=10.9 Hz), 5.01 (s, 2H); $^1$H NMR (400 MHz, DMSO-d6): δ 3.68 (br s, 2H), 3.88 (dd, 2H, J=2.6 Hz, J=10.3 Hz), 3.98 (dd, 2H, J=5.2 Hz, J=10.4 Hz), 4.85 (s, 2H), 8.71 (br s, 6H); $^{13}$C NMR (100 MHz, D$_2$O): δ 55.9, 70.1 and 84.6; $^{13}$C NMR (100 MHz, DMSO-d6): δ 55.5, 70.2 and 84.7; Elemental analysis calculated for $C_6H_{14}O_2N_2Cl_2$: C, 33.50%; H, 6.56%; N, 13.03%; Cl, 32.03%. found C, 33.24%; H, 6.43%; N, 12.72%; Cl, 33.98%.

Shown in FIG. 24 is a scheme for the conversion of DAB-Am-8 Dendrimer (Generation 2.0) into a salt form.

Shown in Table 3 are various salts of DAB-Am-8 Dendrimer (Generation 2.0).

TABLE 3

| Salt of DAB-Am-8 | HB | n × HB | MW of salt (g/mol) |
| --- | --- | --- | --- |
| DAB-Glycolate | 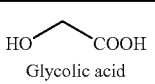 Glycolic acid | 14 × C$_2$H$_4$O$_3$ | 1837.99 |
| DAB-L-Lactate | 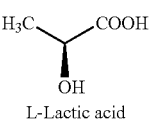 L-Lactic acid | 14 × C$_3$H$_6$O$_3$ | 2034.36 |

TABLE 3-continued

| Salt of DAB-Am-8 | HB | n × HB | MW of salt (g/mol) |
|---|---|---|---|
| DAB-L-Malate | 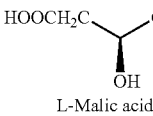 L-Malic acid | 7 × $C_4H_6O_5$ | 1711.88 |
| DAB-D-(−)-Tartrate | 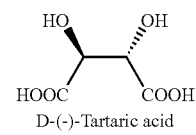 D-(−)-Tartaric acid | 7 × $C_4H_6O_6$ | 1823.88 |
| DAB-Succinate | 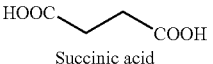 Succinic acid | 7 × $C_4H_6O_4$ | 1599.89 |
| DAB-Citrate | 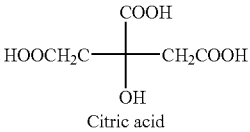 Citric acid | 4.666 × $C_6H_8O_7$ | 1669.72 |

Following is a general procedure for the conversion of DAB-Am-8, Polypropylenimine octaamine Dendrimer (Generation 2.0) into salt forms under highly diluted conditions.

DAB-Am-8, Polypropylenimine octaamine Dendrimer (Generation 2.0)(DSM product) 0.243 g (0.314 mmol) was dissolved in deionized water (56 mL). The solution was vigorously stirred for 30 min and at the same time air was removed by purging with argon. Then pH was measured (pH=11.4) and acid was added slowly. Reaction mixture was stirred at room temperature for next 3 h and then pH was measured again. The sample was frozen and lyophilized for 48 h. The resulted product was ground (when hard foam was formed) and dried in vacuum oven at 40° C. for 48 h. Results are shown in Table 4.

TABLE 4

| Salt of DAB-Am-8 | Acid | g (mmol of acid) | pH of reaction mixture | Form of dried salt | Yield (%) |
|---|---|---|---|---|---|
| DAB-Glycolate | Glycolic acid | 0.335 g (4.408 mmol) | 4.5 | oil | 98 |
| DAB-L-Lactate | L-Lactic acid | 0.397 g (4.408 mmol) | 4.6 | oil | 97 |
| DAB-L-Malate | L-Malic acid | 0.295 g (2.204 mmol) | 5.2 | powder | 99 |
| DAB-D-(−)-Tartrate | D-(−)-Tartaric acid | 0.333 g (2.204 mmol) | 5.6 | powder | 97 |
| DAB-Succinate | Succinic acid | 0.260 g (2.204 mmol) | 5.5 | powder | 97 |
| DAB-Citrate | Citric acid monohydrate | 0.308 g (1.466 mmol) | 5.8 | powder | 97 |

Following is the procedure that was used for the preparation of DAB-Am-8, Polypropylenimine octaamine Dendrimer citrate (Generation 2.0) under concentrated conditions.

DAB-Am-8, Polypropylenimine octaamine Dendrimer (Generation 2.0)(DSM product) 15.468 g (20.003 mmol) was dissolved in deionized water (60 mL). The solution was vigorously stirred for 1 h and at the same time air was removed by purging with argon. Then pH was measured (pH=12.5) and anhydrous citric acid was added slowly (for about 20 min). Reaction mixture became orange and was stirred at room temperature for next 3 h. Then pH was measured again (pH=5.8). The sample was frozen and lyophilized for 48 h. The resulted pale orange hard foam was dried in vacuum oven at 55° C. for 48 h, ground and dried again as long as constant weight was achieved to give 33.065 g (19.803 mmol, 99%) of DAB-Am-8, Polypropylenimine octaamine Dendrimer citrate (Generation 2.0)(DAB-Am-8×4.666 molecules of citric acid) as a pale orange powder.

NMR and Elemental Analysis Data.

All NMR samples contained 20-21 mg of each salt in 0.6 mL of deuterium oxide. The residual peak of $H_2O$ (δ 4.80 ppm) was treated as a reference in $^1H$ NMR.

DAB-Am-8, Polypropylenimine octaamine Dendrimer glycolate (Generation 2.0) (DAB-Am-8×14 molecules of glycolic acid). $^1H$ NMR (400 MHz, $D_2O$): δ 1.77 (bs, 4H), 2.05-2.16 (m, 24H), 3.09 (t, 16H, J=7.6 Hz), 3.15-3.22 (m, 36H), 3.97 (s, 28H); $^{13}C$ NMR (100 MHz, $D_2O$): δ 19.2, 20.8, 21.8, 36.6, 49.6, 49.8, 50.1, 52.5, 61.1, 179.6; Elemental analysis calculated for $C_{68}H_{152}N_{14}O_{42}$ ($C_{40}H_{96}N_{14}$+14× $C_2H_4O_3$): C, 44.44%; H, 8.33%; N, 10.67% with ratio C/N, 4.16; C/H, 5.33; N/H, 1.28. found C, 42.14%; H, 8.36%; N, 10.12% with ratio C/N, 4.16; C/H, 5.04; N/H, 1.21.

DAB-Am-8, Polypropylenimine octaamine Dendrimer L-lactate (Generation 2.0)(DAB-Am-8×14 molecules of L-lactic acid). $^1H$ NMR (400 MHz, $D_2O$): δ 1.33 (d, 42H, J=6.9 Hz), 1.76 (bs, 4H), 2.06-2.12 (m, 24H), 3.08 (t, 16H, J=7.7 Hz), 3.14-3.19 (m, 36H), 4.12 (q, 14H); $^{13}C$ NMR (100 MHz, $D_2O$): δ 19.4, 20.1, 20.8, 21.9, 36.6, 49.6, 49.8, 50.1, 52.5, 68.2, 182.2; Elemental analysis calculated for $C_{82}H_{180}N_{14}O_{42}$ ($C_{40}H_{96}N_{14}$+14×$C_3H_6O_3$): C, 48.41%; H, 8.92%; N, 9.64% with ratio C/N, 5.02; C/H, 5.43; N/H, 1.08. found C, 48.26%; H, 9.10%; N, 9.53% with ratio C/N, 5.06; C/H, 5.30; N/H, 1.05.

DAB-Am-8, Polypropylenimine octaamine Dendrimer L-malate (Generation 2.0) (DAB-Am-8×7 molecules of L-malic acid). $^1H$ NMR (500 MHz, $D_2O$): δ 1.79 (bs, 4H), 2.10-2.18 (m, 24H), 2.43 (dd, 7H, J=9.1 and J=15.3 Hz), 2.67 (dd, 7H, J=3.5 Hz), 3.08 (t, 16H, J=7.6 Hz), 3.16-3.25 (m, 36H), 4.29 (dd, 7H, J=6.9 Hz); $^{13}C$ NMR (125 MHz, $D_2O$): δ 19.1, 20.6, 21.6, 36.5, 42.3, 49.6, 49.7, 49.9, 52.2, 70.0, 179.2, 180.6; Elemental analysis calculated for $C_{68}H_{138}N_{14}O_{35}$ ($C_{40}H_{96}N_{14}$+7×$C_4H_6O_5$): C, 47.71%; H, 8.12%; N, 11.45% with ratio C/N, 4.17; C/H, 5.87; N/H, 1.41. found C, 46.61%; H, 8.16%; N, 11.06% with ratio C/N, 4.21; C/H, 5.71; N/H, 1.35.

DAB-Am-8, Polypropylenimine octaamine Dendrimer D-(−)-tartrate (Generation 2.0)(DAB-Am-8×7 molecules of D-(−)-tartaric acid). $^1$H NMR (400 MHz, D$_2$O): δ 1.78 (bs, 4H), 2.13-2.20 (m, 24H), 3.09 (t, 16H, J=7.6 Hz), 3.24-3.29 (m, 36H), 4.34 (s, 14H); $^{13}$C NMR (100 MHz, D$_2$O): δ 19.0, 20.5, 21.5, 36.5, 49.7, 49.8, 49.9, 52.1, 73.9, 178.4; Elemental analysis calculated for $C_{68}H_{138}N_{14}O_{42}$ ($C_{40}H_{96}N_{14}$+7× $C_4H_6O_6$): C, 44.78%; H, 7.63%; N, 10.75% with ratio C/N, 4.16; C/H, 5.87; N/H, 1.41. found C, 44.44%; H, 7.84%; N, 10.73% with ratio C/N, 4.14; C/H, 5.67; N/H, 1.37.

DAB-Am-8, Polypropylenimine octaamine Dendrimer succinate (Generation 2.0)(DAB-Am-8×7 molecules of succinic acid). $^1$H NMR (400 MHz, D$_2$O): δ 1.77 (bs, 4H), 2.01-2.15 (m, 24H), 2.41 (s, 28H), 3.07-3.20 (m, 52H); $^{13}$C NMR (100 MHz, D$_2$O): δ 19.4, 20.8, 22.0, 33.5, 36.8, 49.6, 2×50.0, 52.3, 181.8; Elemental analysis calculated for $C_{68}H_{138}N_{14}O_{28}$ ($C_{40}H_{96}N_{14}$+7×$C_4H_6O_6$): C, 51.05%; H, 8.69%; N, 12.25% with ratio C/N, 4.16; C/H, 5.87; N/H, 1.41. found C, 50.03%; H, 8.95%; N, 12.07% with ratio C/N, 4.14; C/H, 5.58; N/H, 1.35.

DAB-Am-8, Polypropylenimine octaamine Dendrimer citrate (Generation 2.0)(DAB-Am-8×4.666 molecules of citric acid). $^1$H NMR (400 MHz, D$_2$O): δ 1.78 (bs, 4H), 2.07-2.19 (m, 24H), 2.50 and 2.65 (2×d, J=15.0 Hz, 2×9.33H), 3.07 (t, 16H, J=7.3 Hz), 3.10-3.25 (m, 36H); $^{13}$C NMR (100 MHz, D$_2$O): δ 19.2, 20.5, 21.7, 36.7, 45.9, 49.6, 49.7, 49.9, 52.0, 75.1, 178.8, 181.5; Elemental analysis calculated for ($C_{40}H_{96}N_{14}$+4.666×$C_6H_8O_7$): C, 48.91%; H, 8.05%; N, 11.74% with ratio C/N, 4.16; C/H, 6.07; N/H, 1.46. found C, 47.47%; H, 7.95%; N, 11.14% with ratio C/N, 4.16; C/H, 5.97; N/H, 1.44.

Biological Screening of Novel Oral Phosphate Binders.

Figure 25:
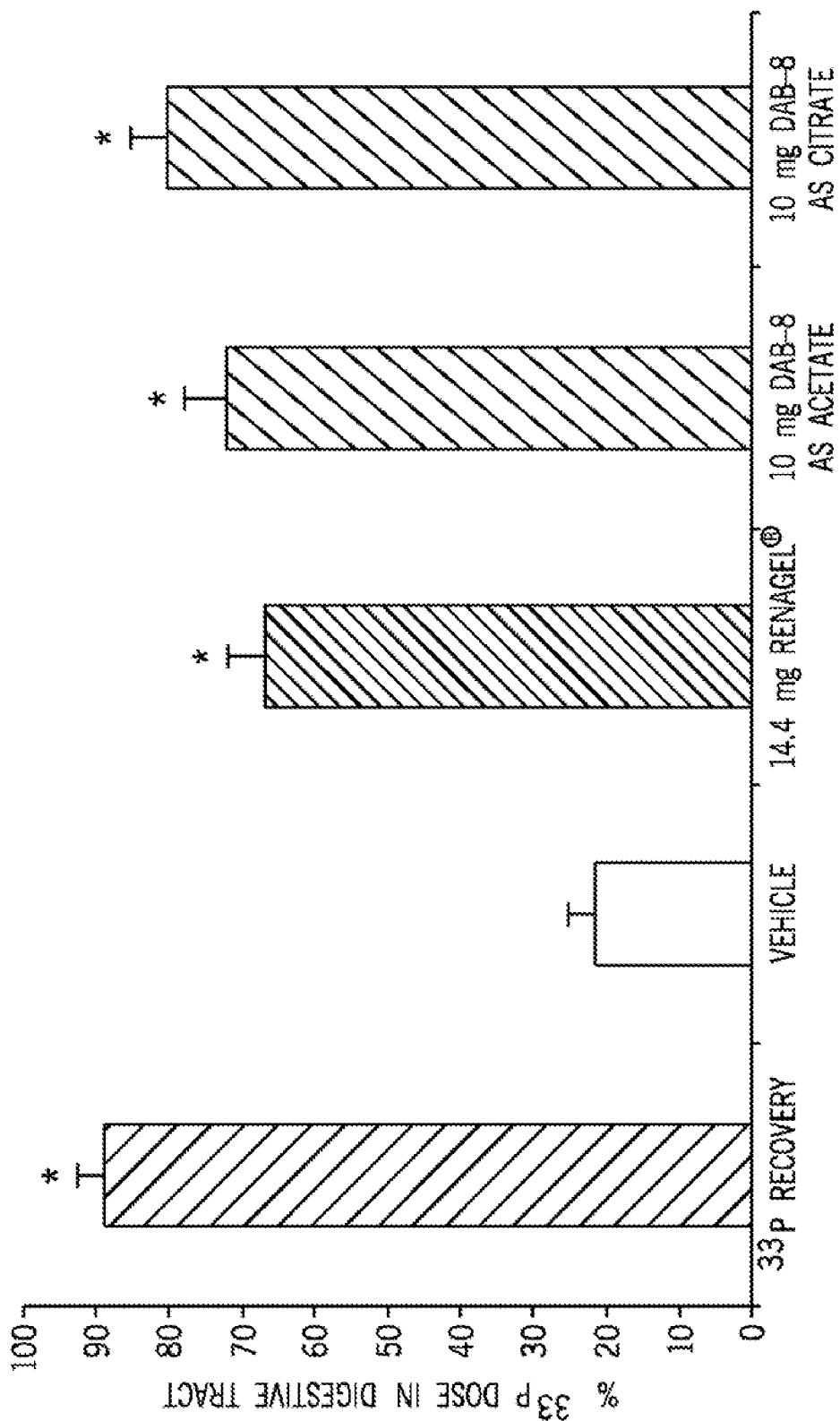
FIG. 25 is a bar graph showing intestinal $^{33}$P absorption.
Figure 26:
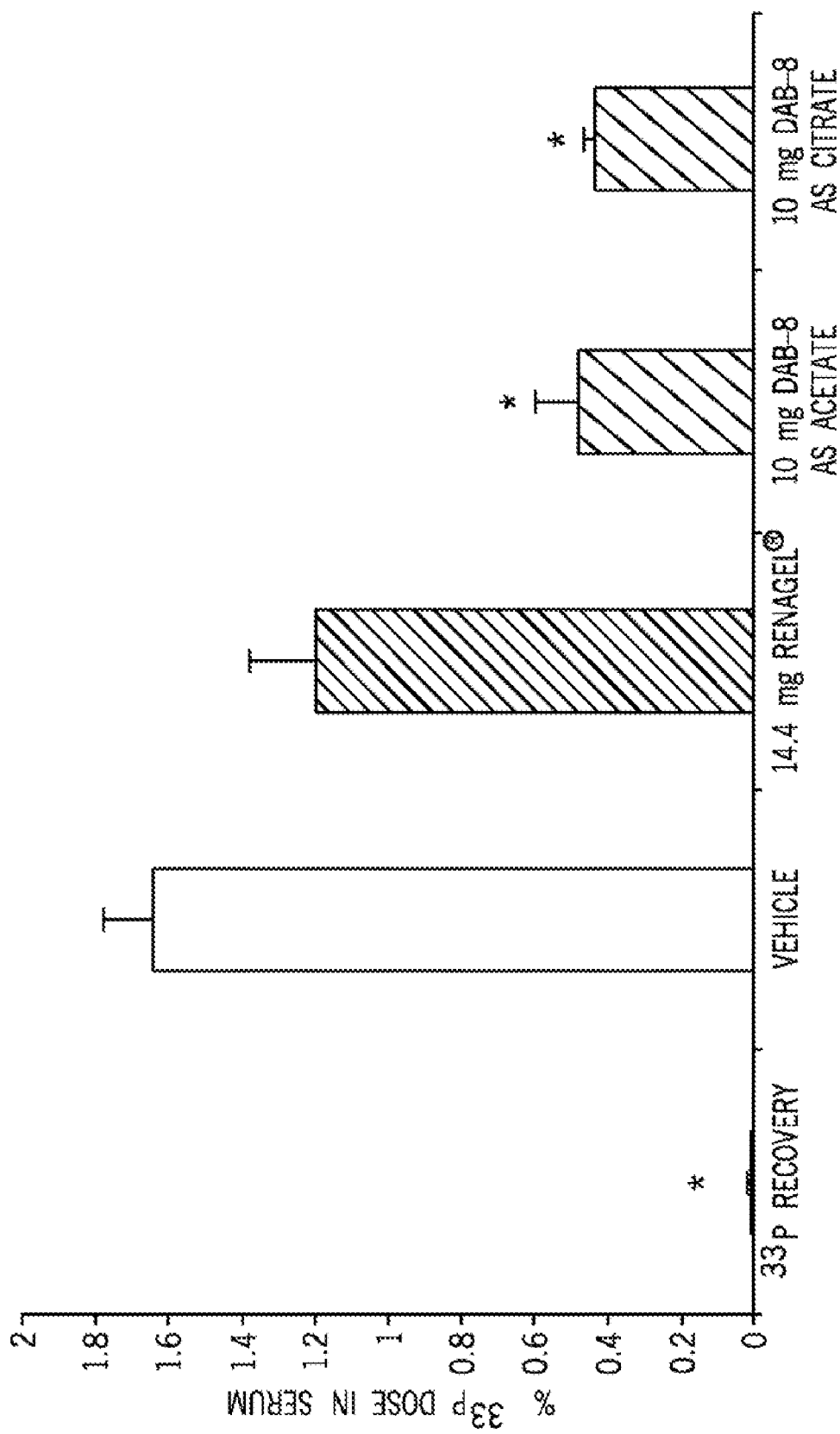
FIG. 26 is a bar graph showing absorption of $^{33}$P into serum.

FIGS. 25 and 26 demonstrate a direct comparison of the phosphate binding potential of the hydroacetate and hydrocitrate forms of DAB-8 in vivo.

Materials and Methods. The relevant materials and methods were the same as set forth above except that instead of using "0.5 mL of water or 39.5 mg calcium acetate, 14.4 mg RENAGEL, or up to 132.8 mg of test dendrimer," the following was used "0.5 mL of water, 14.4 mg RENAGEL or 10 mg DAB-8 as the hydroacetate or hydrocitrate form dissolved in water."

Results. The absence of $^{33}$P in the serum and the presence of (89.0±3.5) % of the $^{33}$P dose in the gut immediately after the dose indicates that the radioactivity was administered properly. Rats given 14.4 mg Renagel™, 10 mg of DAB-8 as acetate or 10 mg DAB-8 as citrate all retained significantly more $^{33}$P in the gut than those pretreated with vehicle. Additionally, there was significantly less $^{33}$P in the serum of rats dosed with either form of DAB-8, but not with Renagel™.

FIG. 25 shows the intestinal $^{33}$P Absorption. Fasted rats were dosed with 0.5 mL water, Renagel™ or a test phosphate binder vial gastric gavage. A second 0.5 mL dose containing 3 μCi $^{33}$P in a 10 mM KH$_2$PO$_4$-containing buffer was immediately administered after the initial dose via gastric gavage. Data represent the mean percentage of the $^{33}$P dose remaining in the digestive tract after 60 minutes. *Indicates significant difference from vehicle pretreatment with a p-value of ±0.05.

FIG. 26 shows the absorption of $^{33}$P into serum. Fasted rats were dosed with 0.5 mL water, Renagel™ or a test phosphate binder vial gastric gavage. A second 0.5 μL dose containing 3 μCi $^{33}$P in a 10 mM KH$_2$PO$_4$-containing buffer was immediately administered after the initial dose via gastric gavage. Data represent the mean percentage of the $^{33}$P dose remaining in the blood serum after 60 minutes. *Indicates significant difference from vehicle pretreatment with a p-value of +0.05.

Thus, DAB-8, in both the hydroacetate and hydrocitrate forms, significantly increased retention of phosphate in the gut and reduced absorption of phosphate into serum. Both salts produced the same effect at equal doses of the dendrimer (DAB-8) suggesting both forms are biologically equivalent on phosphate binding in vivo.

Figure 27:
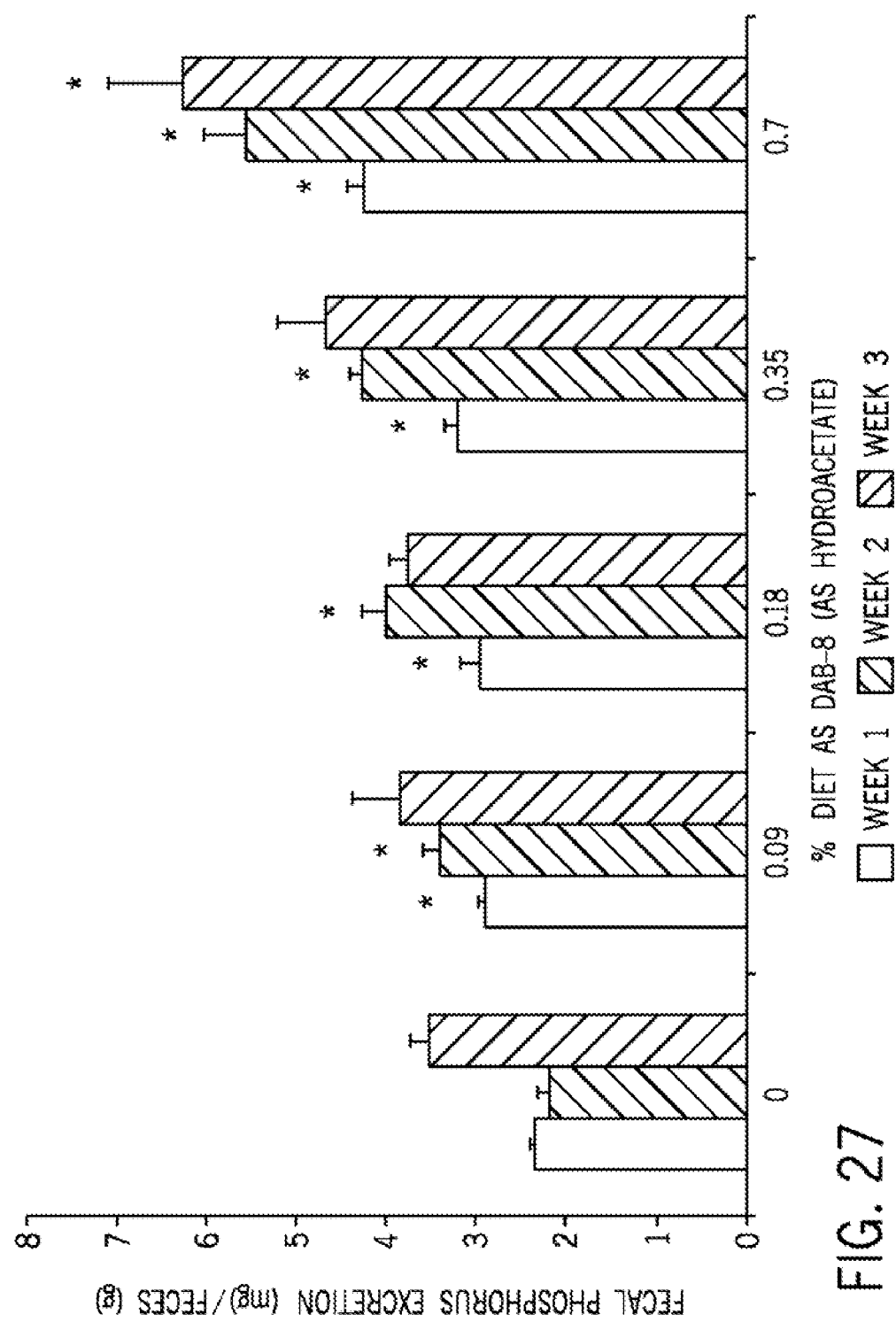
FIG. 27 is a bar graph showing fecal phosphorus content.

FIG. 27 demonstrates the dose-related phosphate binding ability of DAB-8 as the hydroacetate form in vivo.

Materials and Methods. Young male Sprague-Dawley rats weighing approximately 90 g were fed a purified diet containing 0.47% calcium and 0.2% inorganic phosphorus, solidified with molten agar, for 5 days. After this acclimation period, the rats were divided into 5 groups by body weight. One group remained on the control diet while the other 4 groups were fed diets containing increasing levels of DAB-8 in the hydroacetate salt form (0.09 to 0.7%). After 1, 2 and 3 weeks on the diets, the rats were moved to metabolic caging and 24 to 48 hour fecal collections were obtained. The feces were dried then ashed in a muffle oven at 700° C. for 24 hours. The resulting ash was dissolved in 6N HCl and the phosphorus content was measured using an in-house colorimetric assay.

Data are expressed as means±SEM. Data were subjected to analysis of variance (ANOVA), and group means compared using Tukey, Scheffe and Fisher's LSD test. Means were considered significantly different if a p-value ±0.5 was calculated for at least 2 of the comparison tests.

Results. The daily consumption of DAB-8 as the hydroacetate causes a dose-dependent increase in fecal phosphorus output, a measurement that is inversely related to intestinal phosphorus absorption. There is a significant increase in fecal phosphorus content at all four levels of the phosphate binder during the first 2 weeks on the diet. Only the highest dietary level of dendrimer retains significance during week 3. This is caused by an increase in fecal phosphorus output in the control animals, which is likely due to the decreased demand for phosphorus as the rats approach adulthood.

FIG. 27 shows the Fecal Phosphorus Content. Young rats were either control diet ("0"), or the same diet containing one of four levels of DAB-8 as the hydroacetate for three weeks. Feces were collected from the rats using metabolic housing for 24 to 48 hours at the end of the first (week 1), second (week 2) or third (week 3) weeks. Feces was dried, then ashed in a muffle oven. Resulting ash was dissolved in 6N HCl. Phosphorus content was determined using an in-house colorimetric assay. *Indicates significant difference from control diet with a p-value of ±0.05.

The data demonstrates that consumption of DAB-8 as the hydroacetate form causes a dose-dependent reduction in dietary phosphorus absorption in vivo.

Managing blood phosphate is a challenging, but essential, element in the treatment of secondary hyperparathyroidism in chronic kidney disease patients. In addition to dialysis treatment, patients are often administered vitamin D analogs to suppress PTH levels and oral phosphate binders to reduce the absorption of phosphate from foods. Although several types of oral phosphate binders have been developed, all have limited effectiveness due to potential toxicity, low binding ability, or high cost.

The present document compares a variety of novel compounds containing free amino groups for the potential to bind phosphate when administered orally in rats. One of these compounds, FC, does not appear to bind an oral $^{33}$P dose. However, KB-54 and the first, second, third and fifth generations of a DAB dendrimer reduced the absorption of an oral $^{33}$P dose. Each generation of the dendrimer compound bound oral $^{33}$P in a dose dependent manner, and DAB-8 and DAB-16 bound significantly more $^{33}$P than did an equivalent amount of Renagel®.

The mechanism by which dendrimer compounds bind phosphate was investigated by measuring the ability of equal number of moles and equal number of free amino groups from DAB-4, DAB-8, and DAB-16 to reduce the absorption of $^{33}$P. When an equivalent number of free amino groups was administered in the form of DAB-4 and DAB-16, DAB-16 bound significantly more $^{33}$P, suggesting free amino groups are not exclusively responsible for the dendrimer's ability to bind phosphate. However, when an equimolar amount of DAB-8 and DAB-16 were administered to rats, DAB-16 retained significantly more $^{33}$P in the digestive tract, implying that the number of free amino groups may be, in part, responsible for the dendrimer compound's ability to bind phosphate.

Tolerable levels of the DAB-4, DAB-8, and DAB-16 dendrimers were then fed to rats and were found to increase fecal phosphorus levels. Although the differences were significant by the Fisher's LSD test only, the increase in fecal phosphorus by DAB-8 and DAB-16 was significantly higher then the increase from excess calcium or an equivalent amount of Renagel®.

Unfortunately, little is known regarding the toxicity of DAB dendrimers when administered orally. Previous research has shown DAB dendrimers to be cytotoxic in vitro (Duncan R et al., Dendrimer biocompatibility and toxicity, *Adv Drug Deliv Rev* 2005, 57:2215-2237) and when administered intravenously, the DAB dendrimers are lethal. (Schatzlein A G et al., Preferential liver gene expression with polypropylenimine dendrimers, *J Control Release* 2005, 101: 247-258). In our experiments, however, the DAB dendrimers were well tolerated by rats when administered orally. DAB-4, DAB-8, and DAB-16 as hydrochlorides were tolerated at 0.15% of the diet, but when fed at levels as high as 0.3% or 0.6%, only softened stool was observed after 5 days (data not shown).

We claim:
1. A compound comprising the dendrimer having the formula $C_{16}H_{40}N_6$,

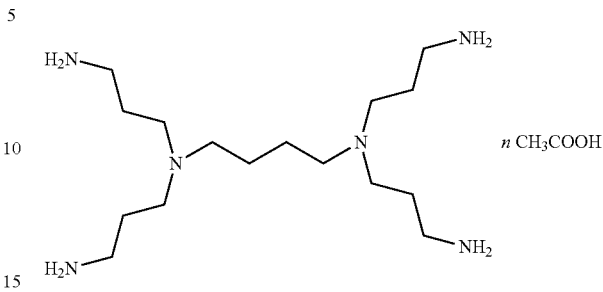

where n=1-6 hydroacetates, and,
a quantity of a pharmaceutically suitable salt in the range of 1-126.

2. A compound comprising the dendrimer having the formula $C_{40}H_{96}N_{14}$,

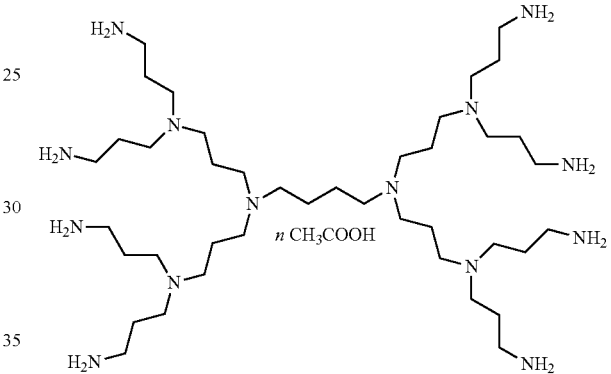

where n=1-14 hydroacetates, and,
a quantity of a pharmaceutically suitable salt in the range of 1-126.

3. A compound comprising the dendrimer having the formula $C_{88}H_{208}N_{30}$,

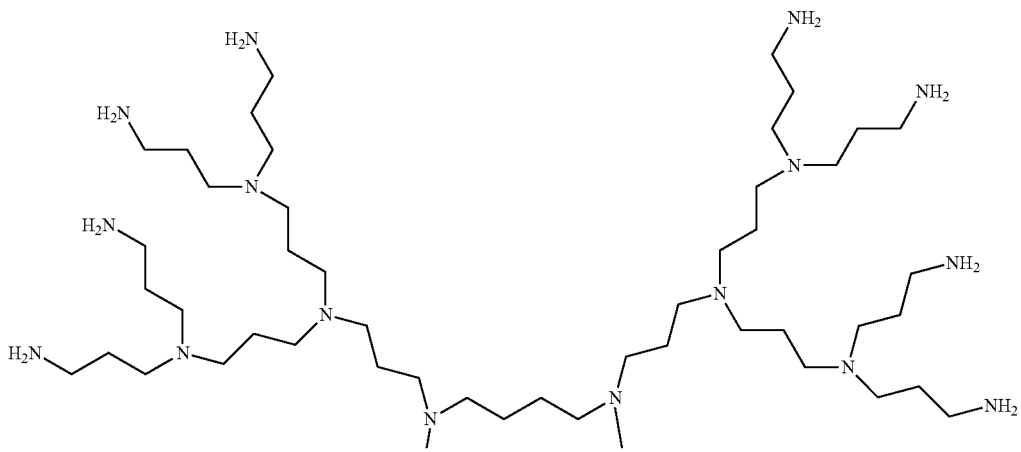

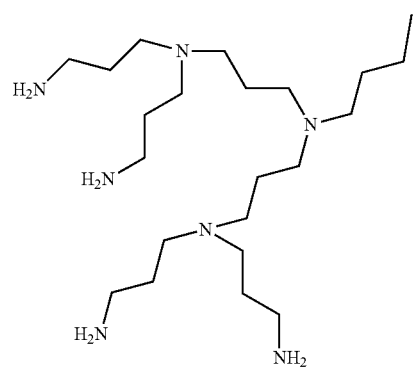
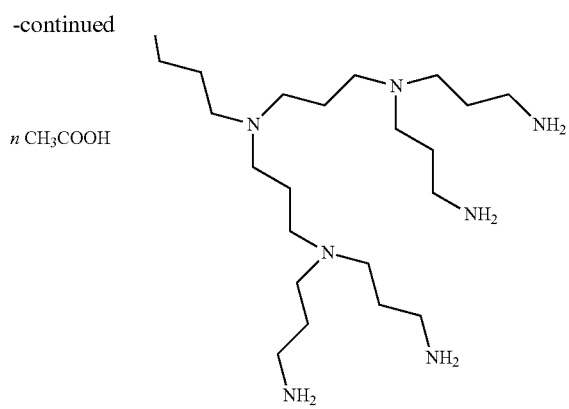
where n=1-30 hydroacetates, and
a quantity of a pharmaceutically suitable salt in the range of 1-126.
4. A compound comprising the dendrimer having the formula $C_{376}H_{880}N_{126}$,
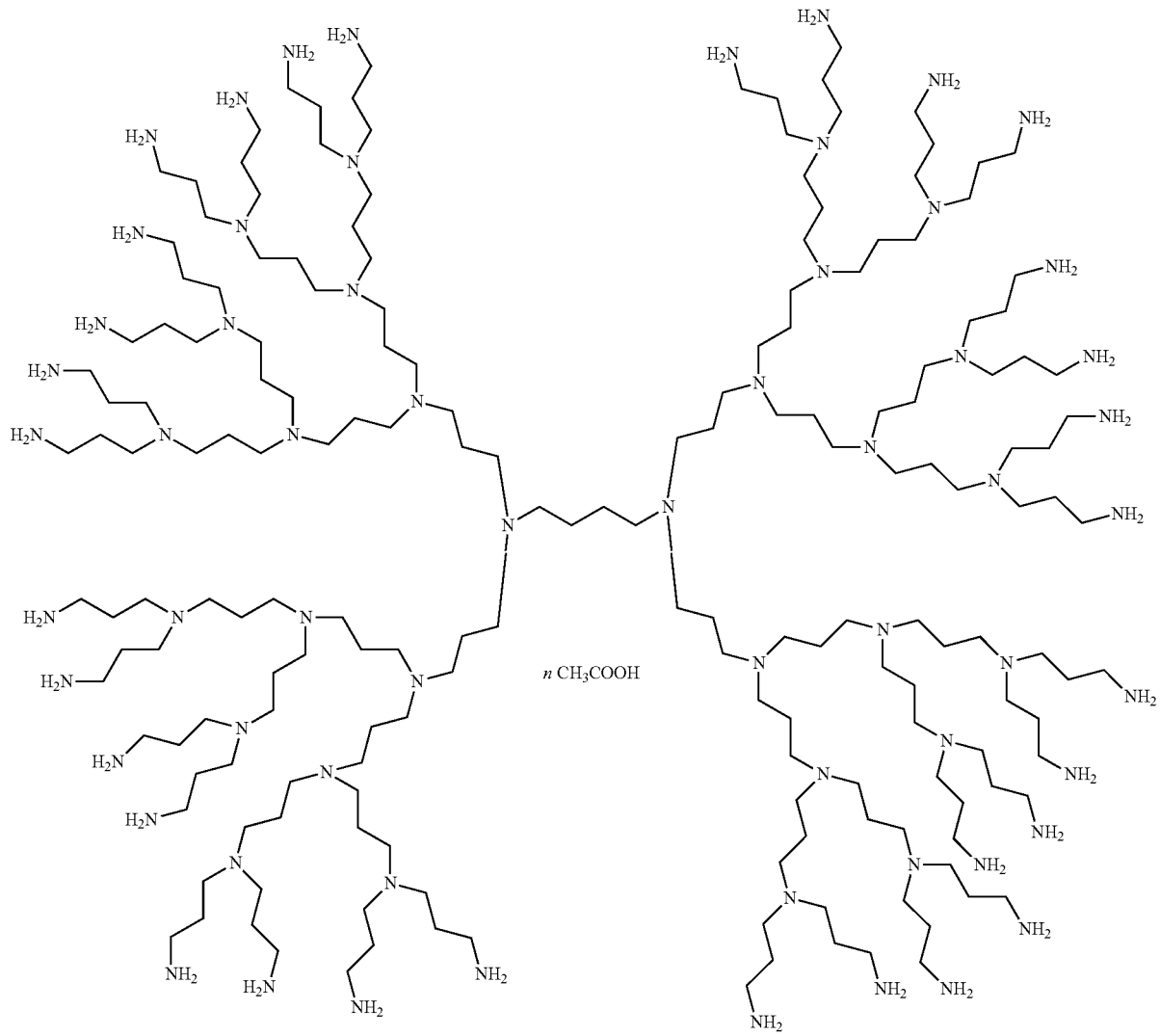

where n=1-126 hydroacetates, and
a quantity of a pharmaceutically suitable salt in the range of 1-126.

5. A compound comprising the dendrimer having the formula $C_{16}H_{40}N_6$,

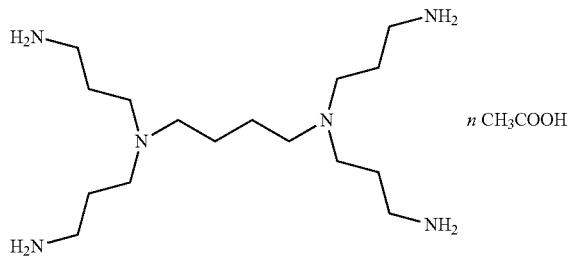

$n\ CH_3COOH$ wherein n=5-6 hydroacetates, and
a quantity of a pharmaceutically suitable salt in the range of 1-126.

6. A compound comprising the dendrimer having the formula $C_{40}H_{96}N_{14}$,

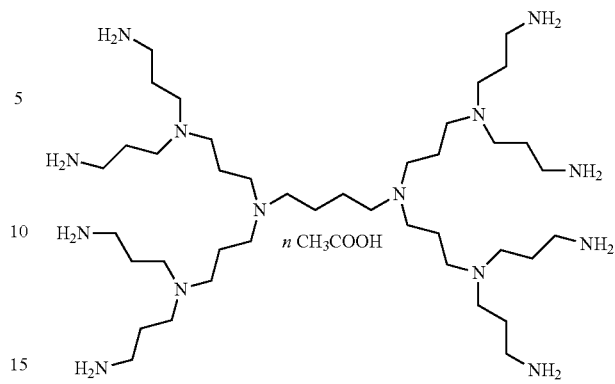

$n\ CH_3COOH$ wherein n=12-14 hydroacetates, and
a quantity of a pharmaceutically suitable salt in the range of 1-126.

7. A compound comprising the dendrimer having the formula $C_{88}H_{208}N_{30}$,

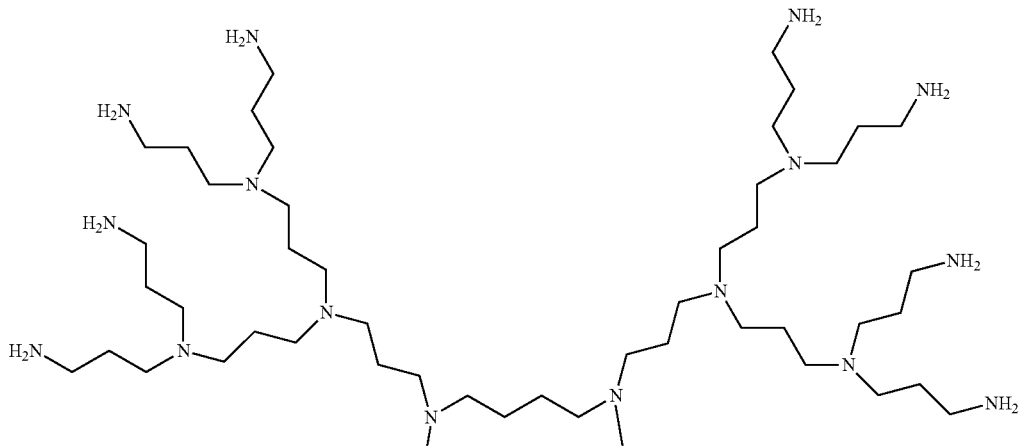

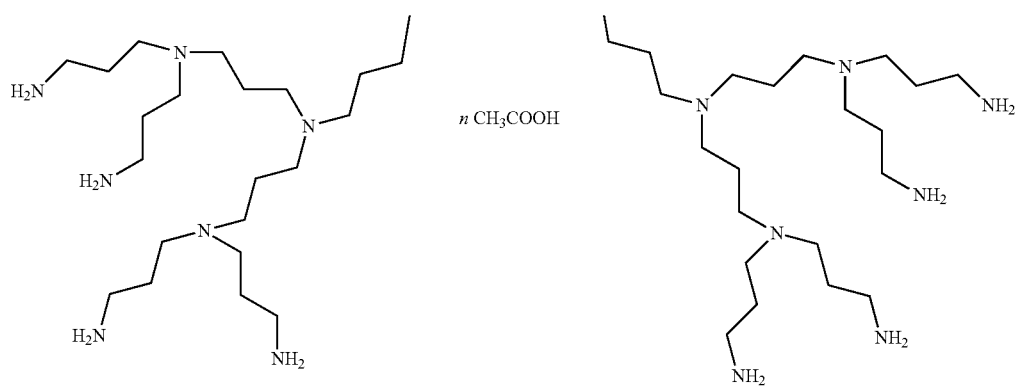

$n\ CH_3COOH$ wherein n=27-30 hydroacetates, and
a quantity of a pharmaceutically suitable salt in the range of 1-126.
8. A compound comprising the dendrimer having the formula $C_{376}H_{880}N_{126}$,
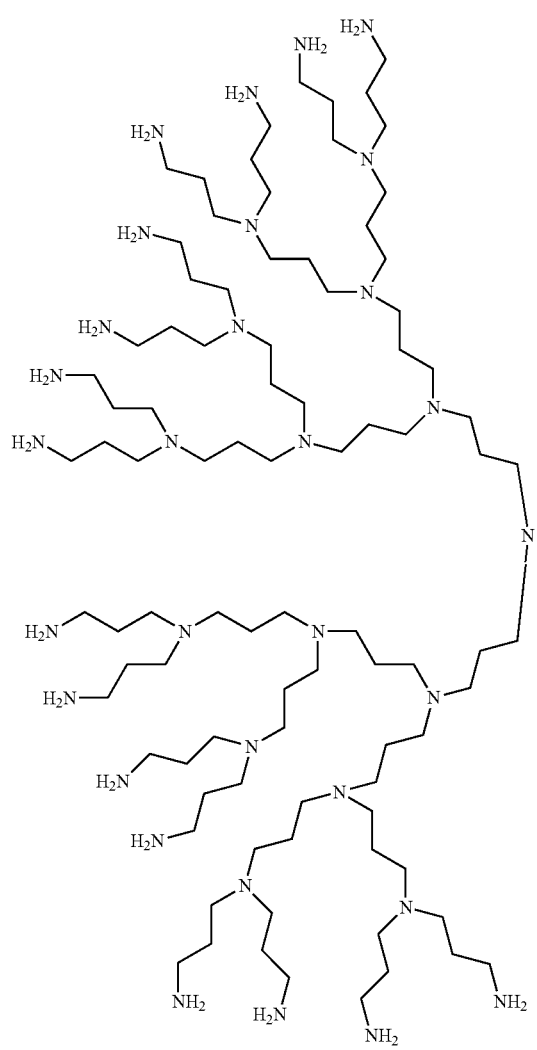
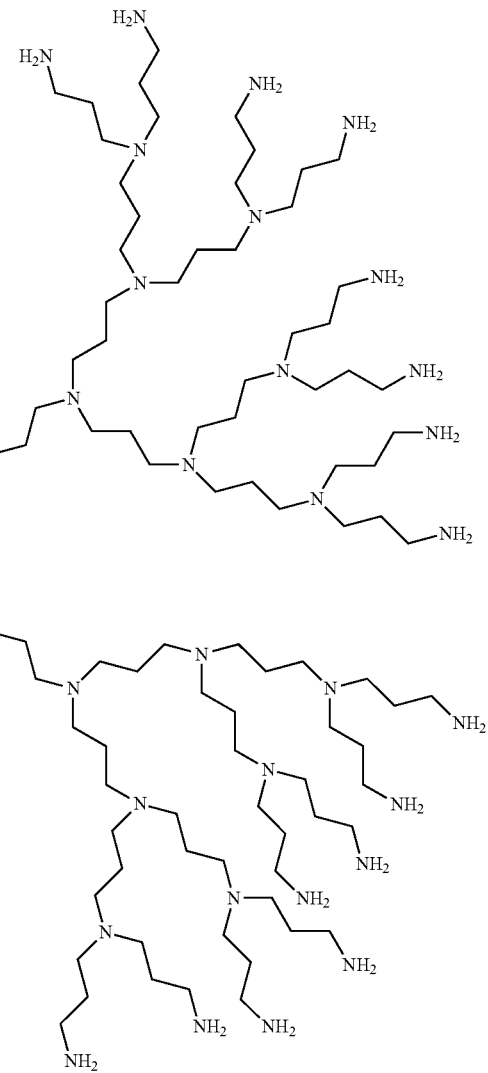
wherein n=113-126 hydroacetates, and
a quantity of a pharmaceutically suitable salt in the range of 1-126.
* * * * *

UNITED STATES PATENT AND TRADEMARK OFFICE
CERTIFICATE OF CORRECTION

PATENT NO. : 8,114,393 B2
APPLICATION NO. : 11/974254
DATED : February 14, 2012
INVENTOR(S) : DeLuca et al.

It is certified that error appears in the above-identified patent and that said Letters Patent is hereby corrected as shown below:

Column 3, line 26 "tetraminobutane" should be --tetraaminobutane--

Column 11, line 37 "tetraminobutane" should be --tetraaminobutane--

Column 12, line 63 "octamine" should be --octaamine--

Column 13, lines 1-2 "tetraminobutane" should be --tetraaminobutane--

Column 14, line 23 "dinitrile" should be --dinatrile--

Column 17, line 37 "tetraminobutane" should be --tetraaminobutane--

Column 22, line 33-34 "tetraminobutane" should be --tetraaminobutane--

Column 23, line 17 "tetraminobutane" should be --tetraaminobutane--

Signed and Sealed this
Twenty-ninth Day of May, 2012

David J. Kappos
*Director of the United States Patent and Trademark Office*